US006791007B1

(12) United States Patent
Schulze-Lefert et al.

(10) Patent No.: US 6,791,007 B1
(45) Date of Patent: Sep. 14, 2004

(54) POLYNUCLEOTIDE AND ITS USE FOR MODULATING A DEFENCE RESPONSE IN PLANTS

(75) Inventors: Paul M. J. Schulze-Lefert, Norwich (GB); Ralph Panstruga, Aachen (DE); Rainer Büschges, Aachen (DE); Augustinus F. M. Simons, Ede (NL); Johannes S. Groenendijk, Wageningen (NL); Theodoor A. J. Van Der Lee, Gorinchem (NL)

(73) Assignees: Plant Bioscience Limited, Norfolk (GB); Keygene N.V., Wageningen (NL)

( * ) Notice: Subject to any disclaimer, the term of this patent is extended or adjusted under 35 U.S.C. 154(b) by 0 days.

(21) Appl. No.: 09/722,377

(22) Filed: Nov. 28, 2000

Related U.S. Application Data

(63) Continuation of application No. 09/230,728, filed as application No. PCT/GB97/02046 on Jul. 29, 1997, now abandoned.

(30) Foreign Application Priority Data

| | | |
|---|---|---|
| Jul. 29, 1996 | (GB) | 9615879 |
| Oct. 30, 1996 | (GB) | 9622626 |
| Mar. 7, 1997 | (GB) | 9704789 |

(51) Int. Cl.[7] ........................ C12N 15/09; C12N 15/29; C12N 15/82; A01H 5/00

(52) U.S. Cl. ....................... 800/279; 800/278; 800/298; 800/295; 435/320.1; 435/419; 435/468; 526/23.6; 526/24.1

(58) Field of Search ................................ 800/279, 298, 800/295, 278, 320.2; 435/419, 468, 320.1; 536/23.6, 24.1

(56) References Cited

U.S. PATENT DOCUMENTS

| | | | | |
|---|---|---|---|---|
| 5,629,470 | A | 5/1997 | Lam et al. | 800/279 |
| 5,689,045 | A | 11/1997 | Logemann et al. | 800/279 |

FOREIGN PATENT DOCUMENTS

| | | |
|---|---|---|
| WO | 95 31564 | 11/1995 |

OTHER PUBLICATIONS

Hinze K et al: "Restriction Fragment Length Polymorphism-Mediated Targeting of the ML–O Resistance Locus in Barley (Hordeum Vulgare)" Proceedings of the National Academy of Sciences of USA, vol. 88, May 1991, Washington US, pp. 3691–3695, XP002035298 cited in the application see abstract.

Tanksley S D et al: Chromosome Landing: A Paradigm for Map–Based Gene Cloning in Trends in Genetics., vol. 11, No. 2, Feb. 1995, Amsterdam NL, pp. 63–68, XP002006911 cited in the whole document.

Becker J et al.: "Combined Mapping of AFLP and RFLP Markers in Barley" Molecule and General Genetics., vol. 249, No. 1, 1995, Berlin DE, pp. 65–73, XP002049470 cited in the application see whole document.

(List continued on next page.)

*Primary Examiner*—Elizabeth F. McElwain
*Assistant Examiner*—Medina A. Ibrahim
(74) *Attorney, Agent, or Firm*—Nixon & Vanderhye PC

(57) ABSTRACT

The present invention relates to stimulating a defense response in plants, with a view to providing the plants with enhance pathogen resistance.

9 Claims, 30 Drawing Sheets

OTHER PUBLICATIONS

Wolter M et al: "The MLO Resistance Alleles to Powdery Mildew Infection in Barley Trigger a Developmentally Controlled Defence Mimic Phenotype" Molecule and General Genetics., vol. 239, 1993, Berlin DE, pp. 122–128, XP002035300 cited in the application see abstract.

Joegensen J H: "Discovery, Characterization and Exploitation of MLO Powdery Mildew Resistance in Barley" Euphytica, col. 63, 1992, Dordrecht NL, pp. 141–152, XP002035755 cited in the application see whole document.

EMBL Sequence Database, Heidleberg, DE Jun. 27, 1994, Accession No. T22145, Arabidopsis Thaliana CDNZ Clone 97N8T7 XP002049473 see abstract.

Bueschges R et al: "The Barley MLO Gene: A Novel Conrol Element of Plant Pathogen Resistance" Cell, vol. 88, No. 5, Mar. 7, 1997, NA US, pp. 695–705, XP002035301 see the whole document.

Simons G et al.: AFLP–Based Fine Mapping of the MLO Gene to a 30–KB DNA Segment of the Barley Genome Genomics, vol. 44, No. 1, Jan. 1997, San Diego US, pp. 64–70, XP002049472 see the whole document.

Sambrooke et al, A laboratory manual, 2$^{nd}$ edition, Chapters 3, 16 and 17 (1989).

Linthorst et al, The Plant Cell 1:285–291 (1989).

Bennetzen et al, Genetic Engineering 14:99–124 (1992).

Figure 2A

M S D K K G V P A R E L P E T P S W A V
ATGTCGGACAAAAAGGGGGTGCCGGCGCGGGAGCTGCCGGAGACGCCGTCGTGGGCGGTG 60

A V V F A A M V L V S V L M E H G L H K
GCGGTGGTCTTCGCCGCCATGGTGCTCGTGTCCGTCCTCATGGAACACGGCCTCCACAAG 120

L G H W F Q H R H K K A L W E A L E K M
CTCGGCCATTGGTTCCAGCACCGGCACAAGAAGGCCCTGTGGGAGGCGCTGGAGAAGATG 180

K A E L M L V G F I S L L L I V T Q D P
AAGGCGGAGCTCATGCTGGTGGGCTTCATATCCCTGCTCCTCATCGTCACGCAGGACCCC 240

I I A K I C I S E D A A D V M W P C K R
ATCATCGCCAAGATATGCATCTCCGAGGATGCCGCCGACGTCATGTGGCCCTGCAAGCGC 300

G T E G R K P S K Y V D Y C P E G K V A
GGCACCGAGGGCCGCAAGCCCAGCAAGTACGTTGACTACTGCCCGGAGGGCAAGGTGGCG 360

L M S T G S L H Q L H V F I F V L A V F
CTCATGTCCACGGGCAGCTTGCACCAGCTGCACGTCTTCATCTTCGTGCTCGCGGTCTTC 420

H V T Y S V I T I A L S R L K M R T W K
CATGTCACCTACAGCGTCATCACCATAGCTCTAAGCCGTCTCAAAATGAGAACATGGAAG 480

K W E T E T T S L E Y Q F A N D P A R F
AAATGGGAGACAGAGACCACCTCCTTGGAATACCAGTTCGCAAATGATCCTGCACGGTTC 540

R F T H Q T S F V K R H L G L S S T P G
CGGTTCACGCACCAGACGTCGTTCGTGAAGCGCCACCTGGGCCTCTCCAGCACCCCTGGC 600

I R W V V A F F R Q F F R S V T K V D Y
ATCAGATGGGTGGTGGCCTTCTTCAGGCAGTTCTTCAGGTCAGTCACCAAGGTGGACTAC 660

L T L R A G F I N A H L S Q N S K F D F
CTGACCTTGAGGGCAGGCTTCATCAACGCGCATTTGTCGCAAAACAGCAAGTTCGACTTC 720

H K Y I K R S M E D D F K V V V G I S L
CACAAGTACATCAAGAGGTCGATGGAGGACGACTTCAAGGTCGTCGTCGGCATCAGCCTC 780

P L W G V A I L T L F L D I N G V G T L
CCGCTGTGGGGTGTGGCGATCCTCACCCTCTTCCTTGACATCAATGGGGTTGGCACGCTC 840

I W I S F I P L V I L L C V G T K L E M
ATCTGGATTTCTTTCATCCCTCTCGTGATCCTCTTGTGTGTTGGAACCAAGCTGGAGATG 900

I I M E M A L E I Q D R A S V I K G A P
ATCATCATGGAGATGGCCCTGGAGATCCAGGACCGGGCGAGCGTCATCAAGGGGGCCCCC 960

V V E P S N K F F W F H R P D W V L F F
GTGGTCGAGCCCAGCAACAAGTTCTTCTGGTTCCACCGCCCCGACTGGGTCCTCTTCTTC 1020

I H L T L F Q N A F Q M A H F V W T V A
ATACACCTGACGTTGTTCCAGAACGCGTTTCAGATGGCGCATTTTGTGTGGACAGTGGCC 1080

T P G L K K C Y H T Q I G L S I M K V V
ACGCCCGGCTTGAAGAAATGCTACCACACGCAGATCGGGCTGAGCATCATGAAGGTGGTG 1140

V G L A L Q F L C S Y M T F P L Y A L V
GTGGGGCTAGCTCTCCAGTTCCTCTGCAGCTATATGACCTTCCCCCTCTACGCGCTCGTC 1200

T Q M G S N M K R S I F D E Q T S K A L
ACACAGATGGGATCAAACATGAAGAGGTCCATCTTCGACGAGCAGACGTCCAAGGCGCTC 1260

Figure 2B

```
 T  N  W  R  N  T  A  K  E  K  K  K  V  R  D  T  D  M  L  M
ACCAACTGGCGGAACACGGCCAAGGAGAAGAAGAAAGTCCGAGACACGGACATGCTGATG    1320

 A  Q  M  I  G  D  A  T  P  S  R  G  S  S  P  M  P  S  R  G
GCTCAGATGATCGGCGACGCAACACCGAGCCGAGGCTCGTCGCCGATGCCGAGCCGGGGC    1380

 S  S  P  V  H  L  L  H  K  G  M  G  R  S  D  D  P  Q  S  A
TCATCACCCGTGCACCTGCTTCACAAGGGCATGGGGCGGTCGGACGACCCCCAGAGCGCG    1440

 P  T  S  P  R  T  Q  Q  E  A  R  D  M  Y  P  V  V  V  A  H
CCCACCTCGCCAAGGACCCAGCAGGAGGCTAGGGACATGTACCCGGTTGTGGTGGCGCAC    1500

 P  V  H  R  L  N  P  N  D  R  R  R  S  A  S  S  S  A  L  E
CCGGTGCACAGACTAAATCCTAACGACAGGAGGAGGTCCGCCTCGTCGTCGGCCCTCGAA    1560

 A  D  I  P  S  A  D  F  S  F  S  Q  G  *
GCCGACATCCCCAGTGCAGATTTTTCCTTCAGCCAGGGATGA    1602
```

Carlsberg II mlo-8 x Haisa mlo-1
mlo-8
mlo-1
1
2
S
R
CO
CO
WG114
ABG366

Haisa mlo-1 x Carlsberg II mlo-5
mlo-1
mlo-5
1
2
3
4
5
6
7
8*
9*
S
R
kb
12
3.8
0.29
0.28
CO
NCO

Figure 5A

```
292 GCGGAGCTCATGCTGGTGGGCTTCATATCCCTGCTCCTCATCGTCACGCA 341
    || :|||| |||||| |||||||||||:|||||||| |||| ||| | ||
 80 GCANAGCTGATGCTGCTGGGCTTCATNTCCCTGCTTCTCACCGTGGCACA 129

342 GGACCCCATCATCGCCAAGATATGCATCTCCGAGGATGCCGCCGACGTCA 391
    || ||   |||| ||||:|| |||||| || ||   || ||| || ||
130 GGCGCC...CATCTCCAANATCTGCATCCCCAAGTCGGCTGCCAACATCT 176

392 TGTGGCCCTGCAAGCGCGGCACCGAGGGCCGC.AAGCCAGCAAGTACGT 440
    ||| ||| ||||||   ||| : || | |  | |||  :|   || | ||
177 TGTTGCCGTGCAAGGCAGGCCNAGATGCCATCGAAGAANAAGCAGCAAGT 226

441 TGACTACTGCCCGGAGGTGAGCAGCAGAGCCCGGACCAGCAGCTTCACGA 490
    | |: |:| || || || | | | | ||  | | ||| :|
227 GGTCNCCNGTCC.TTGGCCGGCGCCGGCGGCGGGGACTACTGCTCNAAAT 275

491 TGATGAAGAAATCAATACC............GAACTTTTTCTTGTTTTCT 528
    |   || | || :||          | ||    ||   : :   :
276 TCGATGTGAGAATAACNCCAGCTGCCGGCAAGCACAACCTCGATNCNATN 325

529 TCTGATTGTCGTCTTGGCTTGGCTTAATTGGTGTGTGTGTGTGTTTGC 578
    ||:|||              |       |||||| | | | | | | |||
326 ACTNATT...........TAACTATAATTGATTTTTCTTGGGTTTTCTGC 364

579 AGGGCAAGGTGGCGCTCATGTCCACGGGCAGCTTGCACCAGCTGCACGTC 628
    |||||||||||||||| |||||   |   ||.| |||||||||||||| |
365 AGGGCAAGGTGGCGCTGATGTCGGCAAAGAGCATGCACCAGCTGCACATT 414

629 TTCATCTTCGTGCTCGCGGTCTTCCATGTCACCTACAGCGTCATCACCAT 678
    |||||||||||||||||  || ||||||||| |||||| || ||||||||
415 TTCATCTTCGTGCTCGCCGTGTTCCATGTTACCTACTGCATCATCACCAT 464

679 AGCTCTAAGCCGTCTCAAAGTGAGCCTTTGCTTCT.....TCTTCTTCTT 723
    | | || | || ||||||||||| | |||| |||      ||| | | ||
465 GGGTTTAGGGCGCCTCAAAGTGAGTTTGTCGTTCTGTCCCTCATGCACAT 514

724 CTTTTACC........GCACGTCTGTCTGTCAGGCGTACCTACCTGTTCA 765
    ||||  |         ||| : |||| |||  |  |  |   |||
515 GTTTTCTCTAGTTCTAGCAANATTGTCAGTCCTTCAAATGGATTGTTTCG 564

766 TCAGGCTTGAGTAAAACTGTTCCATAATCTGC........TCCGGCATAA 807
    ||      || ||  |..||  |||| |||        |      ||||
565 ACA......AGAAACCCAATTTATTAATTTGCCAGTTAAATATATAATAA 608

808 TCCTCTCCTCCTG....CAGATGAAACATGGAAGAAATGGGAGACAGAG 853
    |   || ||       |||||| | ||||||||| |||||| || ||
609 TTGATCTTTCTTGGTTTTAGATGAAGAAATGGAAGAAGTGGGAGTCACAG.658

854 ACCACCTCCTTGGAATACCAGTTCGCAAATGGTCAGGATCCCCCACTCTG 903
    |||| ||| ||||| || ||||||||||| |||   |  | |
659 ACCAACTCATTGGAGTATCAGTTCGCAATCGGTAGTG.......AATTAA 701

904 CAATCTCCC...CTTCTTCGAAACCAAACC....TGATGATCCATTTAAA 946
    |||||||||   | |  ||   | ||||     |||| || || || |||
702 GAATCTCCCTAACTATTTCATTTCAGAACCTTTATGATAATGTCTTGAAA 751

947 GACGCAGGCACGATCAGAGTGAGTGAACTGATGTATGTTCATTTTTTGTG 996
    || | |   ||||| |||   | ||||  |
752 GAGGAGGAGCAAATCAG.CTGAAAAATATGATCGA.............. 785

997 TCCTTTCAGATCCTGCACGGTTCCGGTTCACGCACCAGACGTCGTTCGTG 1046
    ||| | |||||||||| |||| ||| |||||||||||||||||||||||
786 TCCATGCAGATCCTTCACGATTCAGGTTCACGCATCAGACGTCGTTCGTG 835
```

Figure 5B

```
1047 AAGCGCCACCTGGG...CCTCTCCAGCACCCCTGGCATCAGATGGGTGGT 1093
 836 AAGCGGCATCTGGGATCATTCTCAAGCACCCCTGGGCTCAGATGGATCGT 885

1094 GAGTTTTTAGCTTCTTATCTGCCCCTCATCTGTGTGTAATGTT...... 1137
 886 GAGTTATCAATCTCCGAAT........ACATGCTTGTTTTTATTCTTGCA 928

1138 ..TGGCGTA...........TGGAGTCAGGTGATTT.........ACCTT 1165
 929 ACTGGCCTAGCTGTTCCAATTCAATCCATATTTTTGAAAAAAAAAATAT 978

1166 GCCTGTGATGTTTGTTGCCTTGTCAGGTGGCCTTCTTCAGGCAGTTCTTC 1215
 979 TCATGCCGTGTTTG.....TTGTTAGGTAGCATTCTTCAGGCAGTTCTTT 1023

1216 AGGTCAGTCACCAAGGTGGACTACCTGACCTTGAGGGCAGGCTTCATCAA 1265
1024 GGGTCCGTCACCAAGGTGGACTACCTGACCATGCGGCAAGGCTTCATCAA 1073

1266 CGTACGTGC....CTCCCCTTCTAGCTCCGCCATTGCTGCCGCGATGTAG 1311
1074 TGTATATACTAATCAAACCTGACCAATTCAACATTGATGATGC.AAACAG 1122

1312 CAGCAAAGCTTCT.......CAAGTTATCCTTCTGACGCTAAAGTTCCCA 1354
1123 AAGACCAGGTTTTTTTTTTCCGAGTTGTGCAT.TGAAGTTAATG...... 1165

1355 TGTTTTTTCCTCAAATTATTCTGCGCAGGCG.CATTTGTCGCAAAACAGC 1403
1166 .GTTTTAGCTTC...TTCTCTTTTGCAGGCGCCATTTGTCGCAGAATAGC 1211

1404 AAGTTCGACTTCCACAAGTACATCAAGAGGTCGATGGAGGACGACTTCAA 1453
1212 AAGTTCGACTTCCACAAATACATCAAGAGGTCTTTGGAGGACGACTTCAA 1261

1454 GGTCGTCGTCGGCATCAGGTACGTTCCATTCCTTCCTCTGCACCAGACCA 1503
1262 AGTTGTCGTTGGCATCAGGTCCG......TCCTCGCTTT........... 1294

1504 CACCCCATGGATAGATTTTAACAATTGCTGTCAGGTTCCACATGATAACA 1553
1295 ..........ATTAATTATAGGA....CTCTTATATTCAACATTTTTTTT 1330

1554 ATATACTATGA.ACTTGGTCTTTGCTCCTTGTCCTTG.....CACGATCA 1597
1331 ATAAAGAAACATATTTAGTCT...CCAGTTGTGTATGTGTATGTGGATCT 1377

1598 TGACACATTTGGCCTGTTTTCGCAGCCTCCCGCTGTGGGGTGTGGCGATC 1647
1378 TGACACATTTGG.CTGGTTTTGCAGCCTCCCTCTGTGGTTCGTCGGAATC 1426

1648 CTCACCCTCTTCCTTGACATCAATGGTATGGACCTTCTCCTCTCCGGTTT 1697
1427 CTTGTACTCTTCCTCGATATCCACGGTA..ATCCTTGTCCT.....ATTT 1469

1698 CTCTATTGCTTTGCAGCTAAATAAAACACTTGCAATTCGTCTCGTGATCA 1747
1470 CATTCTTTTTTTTACTCTCAAAACCTTGTTCTGAATTGGTCTTATAATCA 1519

1748 CCGCTCATTTTTCAACCATTTCTTTTTCTACTCATAGGGGTTGGCACGCT 1797
1520 CCATCGATTTTTTTTCAACTT.TTTCCCCGCGTGTAGGTCTTGGCACACT 1568

1798 CATCTGGATTTCTTTCATCCCTCTCGTGGTAAGTGC.AGATTTCTCC.AT 1845
1569 TATTTGGATCTCTTTTGTTCCTCTCATCGTAAGAGCGAAATTTCCCCTGT 1618
```

Figure 5C

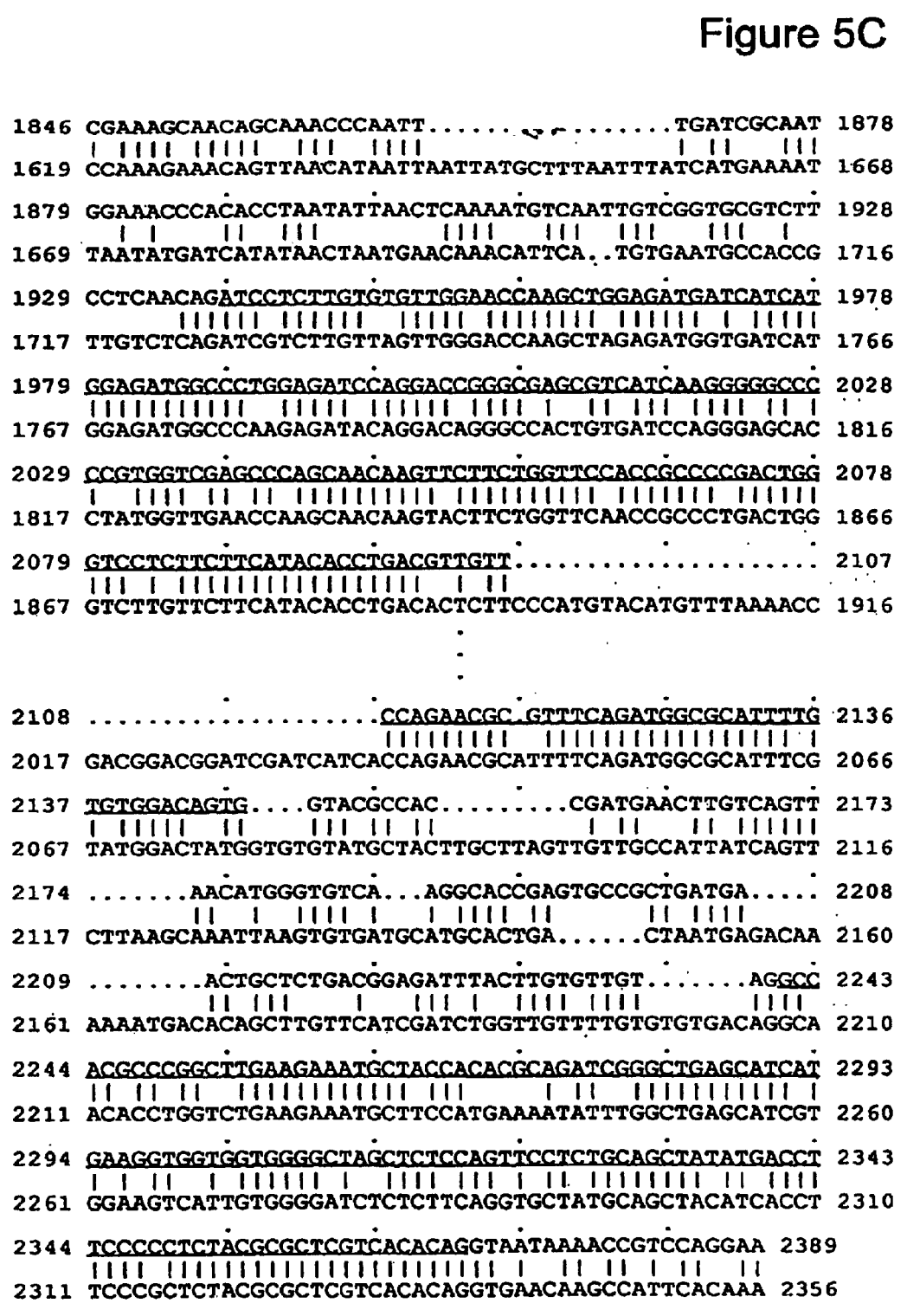

```
1846 CGAAAGCAACAGCAAACCCAATT.....................TGATCGCAAT 1878
1619 CCAAAGAAACAGTTAACATAATTAATTATGCTTTAATTTATCATGAAAAT 1668

1879 GGAAACCCACACCTAATATTAACTCAAAATGTCAATTGTCGGTGCGTCTT 1928
1669 TAATATGATCATATAACTAATGAACAAACATTCA..TGTGAATGCCACCG 1716

1929 CCTCAACAGATCCTCTTGTGTGTTGGAACCAAGCTGGAGATGATCATCAT 1978
1717 TTGTCTCAGATCGTCTTGTTAGTTGGGACCAAGCTAGAGATGGTGATCAT 1766

1979 GGAGATGGCCCTGGAGATCCAGGACCGGGCGAGCGTCATCAAGGGGGCCC 2028
1767 GGAGATGGCCCAAGAGATACAGGACAGGGCCACTGTGATCCAGGGAGCAC 1816

2029 CCGTGGTCGAGCCCAGCAACAAGTTCTTCTGGTTCCACCGCCCCGACTGG 2078
1817 CTATGGTTGAACCAAGCAACAAGTACTTCTGGTTCAACCGCCCTGACTGG 1866

2079 GTCCTCTTCTTCATACACCTGACGTTGTT..................... 2107
1867 GTCTTGTTCTTCATACACCTGACACTCTTCCCATGTACATGTTTAAAACC 1916

.
.
.

2108 .....................CCAGAACGC.GTTTCAGATGGCGCATTTTG 2136
2017 GACGGACGGATCGATCATCACCAGAACGCATTTCAGATGGCGCATTTCG 2066

2137 TGTGGACAGTG....GTACGCCAC.........CGATGAACTTGTCAGTT 2173
2067 TATGGACTATGGTGTGTATGCTACTTGCTTAGTTGTTGCCATTATCAGTT 2116

2174 .......AACATGGGTGTCA...AGGCACCGAGTGCCGCTGATGA..... 2208
2117 CTTAAGCAAATTAAGTGTGATGCATGCACTGA......CTAATGAGACAA 2160

2209 ........ACTGCTCTGACGGAGATTTACTTGTGTTGT.......AGGCC 2243
2161 AAAATGACACAGCTTGTTCATCGATCTGGTTGTTTGTGTGTGACAGGCA 2210

2244 ACGCCCGGCTTGAAGAAATGCTACCACACGCAGATCGGGCTGAGCATCAT 2293
2211 ACACCTGGTCTGAAGAAATGCTTCCATGAAAATATTTGGCTGAGCATCGT 2260

2294 GAAGGTGGTGGTGGGGCTAGCTCTCCAGTTCCTCTGCAGCTATATGACCT 2343
2261 GGAAGTCATTGTGGGGATCTCTCTTCAGGTGCTATGCAGCTACATCACCT 2310

2344 TCCCCCTCTACGCGCTCGTCACACAGGTAATAAAACCGTCCAGGAA 2389
2311 TCCCGCTCTACGCGCTCGTCACACAGGTGAACAAGCCATTCACAAA 2356
```

Figure 6A

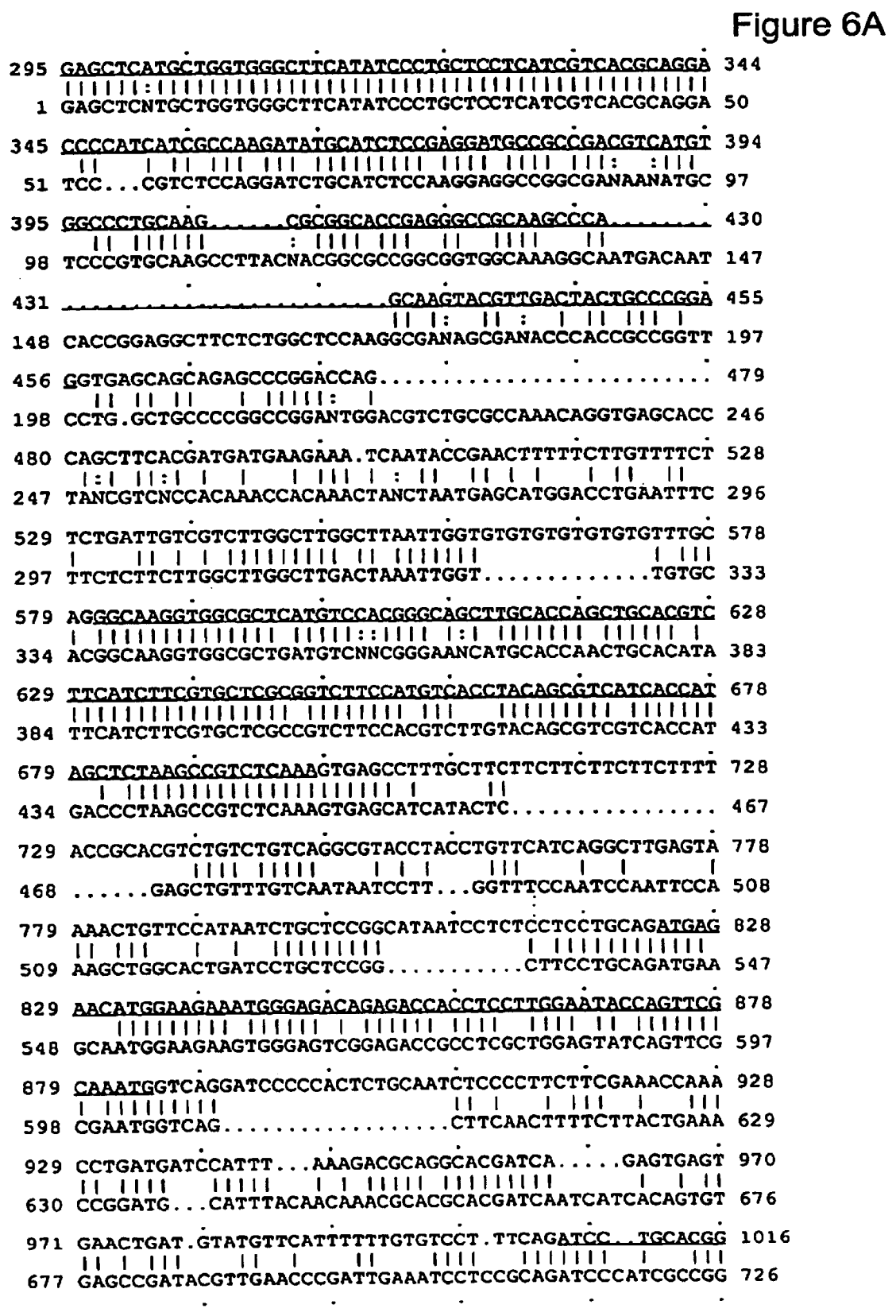

```
295 GAGCTCATGCTGGTGGGCTTCATATCCCTGCTCCTCATCGTCACGCAGGA 344
    ||||||:||||||||||||||||||||||||||||||||||||||||||
  1 GAGCTCNTGCTGGTGGGCTTCATATCCCTGCTCCTCATCGTCACGCAGGA 50

345 CCCCATCATCGCCAAGATATGCATCTCCGAGGATGCCGCCGACGTCATGT 394
    ||  | || ||| ||| ||| ||||||||| |||| |||:  :||| 
 51 TCC...CGTCTCCAGGATCTGCATCTCCAAGGAGGCCGGCGANAANATGC 97

395 GGCCCTGCAAG.....CGCGGCACCGAGGGCCGCAAGCCCA......... 430
    || |||||||    :|||| ||| || |||| ||
 98 TCCCGTGCAAGCCTTACNACGGCGCCGGCGGTGGCAAAGGCAATGACAAT 147

431 ...........................GCAAGTACGTTGACTACTGCCCGGA 455
                               || |:  ||  : |  ||  |
148 CACCGGAGGCTTCTCTGGCTCCAAGGCGANAGCGANACCCACCGCCGGTT 197

456 GGTGAGCAGCAGAGCCCGGACCAG.................... 479
    || || ||   | |||||:   |
198 CCTG.GCTGCCCCGGCCGGANTGGACGTCTGCGCCAAACAGGTGAGCACC 246

480 CAGCTTCACGATGATGAAGAAA.TCAATACCGAACTTTTTCTTGTTTTCT 528
    |:| ||:| |   |    | ||| | :|| || | |  | || ||
247 TANCGTCNCCACAAACCACAAACTANCTAATGAGCATGGACCTGAATTTC 296

529 TCTGATTGTCGTCTTGGCTTGGCTTAATTGGTGTGTGTGTGTGTTTGC 578
    |   || | | ||||||||| || |||||||                | |||
297 TTCTCTTCTTGGCTTGGCTTGACTAAATTGGT............TGTGC 333

579 AGGGCAAGGTGGCGCTCATGTCCACGGGCAGCTTGCACCAGCTGCACGTC 628
    | |||||||||||||| ||||||::|||| |:| |||||||| |||||| |
334 ACGGCAAGGTGGCGCTGATGTCNNCGGGAANCATGCACCAACTGCACATA 383

629 TTCATCTTCGTGCTCGCGGTCTTCCATGTCACCTACAGCGTCATCACCAT 678
    ||||||||||||||||| |||||||||| |||  ||||||||| |||||||
384 TTCATCTTCGTGCTCGCCGTCTTCCACGTCTTGTACAGCGTCGTCACCAT 433

679 AGCTCTAAGCCGTCTCAAAGTGAGCCTTTGCTTCTTCTTCTTCTTCTTTT 728
    | |||||||||||||||||||||||||| ||        ||
434 GACCCTAAGCCGTCTCAAAGTGAGCATCATACTC................ 467

729 ACCGCACGTCTGTCTGTCAGGCGTACCTACCTGTTCATCAGGCTTGAGTA 778
    ||||  ||||||       | | |       |||      |   |      |
468 ......GAGCTGTTTGTCAATAATCCTT...GGTTTCCAATCCAATTCCA 508

779 AAACTGTTCCATAATCTGCTCCGGCATAATCCTCTCCTCCTGCAGATGAG 828
    || |||   |  |  |||||||||            | ||||||||||||
509 AAGCTGGCACTGATCCTGCTCCGG...........CTTCCTGCAGATGAA 547

829 AACATGGAAGAAATGGGAGACAGAGACCACCTCCTTGGAATACCAGTTCG 878
    ||||||||| |||||| | |||||| |||| |||| || ||||||||
548 GCAATGGAAGAAGTGGGAGTCGGAGACCGCCTCGCTGGAGTATCAGTTCG 597

879 CAAATGGTCAGGATCCCCCACTCTGCAATCTCCCCTTCTTCGAAACCAAA 928
    | |||||||||                  || |   | |||  |   |||
598 CGAATGGTCAG..................CTTCAACTTTTCTTACTGAAA 629

929 CCTGATGATCCATTT...AAAGACGCAGGCACGATCA.....GAGTGAGT 970
    || ||||   |||||    | | ||||| ||||||||||    |  | ||
630 CCGGATG...CATTTACAACAAACGCACGCACGATCAATCATCACAGTGT 676

971 GAACTGAT.GTATGTTCATTTTTTGTGTCCT.TTCAGATCC..TGCACGG 1016
    || | |||   || |    ||    ||||  ||||||| |   |||
677 GAGCCGATACGTTGAACCCGATTGAAATCCTCCGCAGATCCCATCGCCGG 726
```

Figure 6B

```
1017 TTCCGGTTCACGCACCAGACGTCGTT.CGTGAAGCGCCACCTGGGCCTCT 1065
     ||||||||||||||||||||||| ||||  |||| ||| |||||||||||||
 727 TGCCGGTTCACGCACCAGACGACGTTGGGTGAGGCGGCACCTGGGCCTCT 776

1066 CCAGCACCCCTGGCATCAGATGGGTGGTGAGTTTTTTAGCTTCTTATCTG 1115
     |||||||||| ||| |||||||||||
 777 CCAGCACCCCGGCGTCAGATGGGT........................ 801

1166 GCCTGTGATGTTTGTTGCCTTGTCAGGTGGCCTTCTTCAGGCAGTTCTTC 1215
                              ||||||||||||||||||||||||||
 802 ........................GGTGGCCTTCTTCAGGCAGTTCTTC 826

1216 AGGTCAGTCACCAAGGTGGACTACCTGACCTTGAGGGCAGGCTTCATCAA 1265
     | ||| || ||||||||||||||||||||||||||| ||   |||||||||.
 827 ACGTCGGTGACCAAGGTGGACTACCTGACCTTGCGGCAGGGCTTCATCAA 876

1266 CGTACGTGCCTCCCCTTCTAGCTCCGCCATTGCTGCCGCGATGTAGCAGC 1315
     |
 877 C................................................ 877

1366 CAAATTATTCTGCGCAGGCGCATTTGTCGCAAAACAGCAAGTTCGACTTC 1415
                       |||||| | |||||  || || |||||||||||
 878 .................GCGCATCTCTCGCAGGGCAACAGGTTCGACTTC 910

1416 CACAAGTACATCAAGAGGTCGATGGAGGACGACTTCAAGGTCGTCGTCGG 1465
     ||||||||||||||||||||||| ||||||||||||||| |||||||| |
 911 CACAAGTACATCAAGAGGTCGTTGGAGGACGACTTCAAAGTCGTCGTCCG 960

1466 CATCAGGTACGTTCCATTCCTTCCTCTGCAC.........CACACCACAC 1506
     ||||||||||||  ||||||||| |||||||         ||  |  |||
 961 CATCAGGTACGCGCCATTCCTTTCTCTGCACAAATTAATACATCCACCAC 1010

1507 CCCATGGATAGATTTTAACAATTGCTGTCAGGTTCCACATGATAACAATA 1556
     | ||| : ||||| || ||                    || : |:| ||
1011 CACATANGTAGATAGATAGA...............TCGATANATANATTA 1045

1557 TACTATGAACTTGGTCTTTGCTCCTTGTCCTTGCACGATCATGACACATT 1606
     ||| | |  |  |  || |  | || || |   | |||| ||||||||
1046 TAC.AAGTGCCGGTACGTACGTACGTCTCAT...ATGATCTTGACACATC 1091

1607 TGGCCTGTTTTCGCAGCCTCCCGCTGTGGGGTGTGGCGATCCTCACCCTC 1656
     || ||| ||  ||||  ||| |||  ||| ||||||  |||||| ||||
1092 TGTCCTCTTGCCGCAATCTCAAGCTCTGGTTCGTGGCGGTCCTCATCCTC 1141

1657 TTCCTTGACATCAATGGTATGGACCTTCTCC.TCTCCGGTTTCTCTATTG 1705
     |||||||| || | ||||    |||| ||| |  || || | |  |   |
1142 TTCCTTGATTTCGACGGTAGCCGCCTTGTCCATGCCCTGCTCGCCCTCTC 1191

1706 CTTTGCAGCTAAATAAAACACTTGCAATTCGTCTCGTGATCACCGCTCAT 1755
     ||  ||  ||   | ||   ||  ||    | ||| |||           ||
1192 CTCCGCTTCTCTCCATAATTTGTG.AACTTGTCCCGT............AT 1229

1756 TTTTCAACCATTTCTTTTTCTACTCATAGGGG.TTGGCACGCTCATCTGG 1804
     |  | ||     ||  ||| |||  |||||| | ||||| ||  |||||
1230 ATAACCACACCACCGTCGTCTTCTCGCAGGGGATCGGCACTCTTCTCTGG 1279

1805 ATTTCTTTCATCCCTCTCGTGGTAAGTGCAGATTTCTCCATCGAAAGCAA 1854
     || ||  ||     | ||||||||||||| ||       | ||   ||  |
1280 ATGTCCGTGGTTCCTCTCGTGGTAAGTCCA.......CAATTTGAATAGA 1322

1855 CAGCAAACCCAATTTGATCGCAATGGAAACCCACACCTAATATTAACTCA 1904
     || |  |||||| |  | || || ||| || |||                 | |
1323 CAACCTGTCCAATTGTGATGTACAGTACCTCCAAACTTAA.......TTA 1365
```

Figure 6C

```
1905 AAATGTCAATTGTCGGTGCGTCTTCC.....TCAACAGATCCTCTTGTGT 1949
     | |||||| ||| | | ||||| |      ||  ||||||||||||
1366 ACATGTCATTTGCTGAT..GTCTTGCGTGTAACATTAGATCCTCTTGTGG 1413

1950 GTTGGAACCAAGCTGGAGATGATCATCATGGAGATGGCCCTGGAGATCCA 1999
     ||||| |||||||||||||||| | |||||||||||||||| |||||||
1414 GTTGGGACCAAGCTGGAGATGGTGATCATGGAGATGGCCCAGGANATCCA 1463

2000 GGACCGGGCGAGCGTCATCAAGGGGGCCCCCGTGGTCGAGCCCAGCAACA 2049
     ||||||| ||||||| |||||| || ||||  |||||||||||||||||
1464 TGACCGGGAGAGCGTCGTCAAGGGTGCTCCCGCCGTCGAGCCCAGCAACA 1513

2050 AGTTCTTCTGGTTCCACCGCCCCGACTGGGTCCTCTTCTTCATACACCTG 2099
     ||| ||||||||||| |||| || |||||||||||||||||||| |||||
1514 AGTACTTCTGGTTCAACCGGCCTGACTGGGTCCTCTTCCTCATGCACCTC 1563

2100 ACGTTGTTCCAGAACGCGTTTCAGATGGCGCATTTTGTGTGGACAGTGGT 2149
     || | |||||||||||||||||||||||| ||||| |||||||||||||
1564 ACACTCTTCCAGAACGCGTTTCAGATGGCTCATTTCGTGTGGACAGTGGT 1613

2150 ACGCCACCGATGAACTTGTCAGTTAACATGGG..................2181
     |   |:  | | |||||||| || || | :|
1614 A...CNTACAAGTACTTGTCACTTCACTTANGCTAACTCCAACAAACGAA 1660

2182 ........TGTCAAGGCACCGAGTGCCGCTGATGAACTGCTCTGACGGAG 2223
             |||| || || | |      |  | | | ||
1711 GACACAAAACTCAATCCAACGCGCGGTAGCAAACGAACGTTTTTCCGTAC 1760

2224 ATTTAC.........................................TTG 2232
     ||| |                                           |||
1761 GTTTTCGTCCGCTTTCGCCCCATCCCAGCCCAAATTCGTTGACGTTGTTG 1810

2233 TGTTGTAGGCCACGCCCGGCTTGAAGAAATGCTACCACACGCAGATCGGG 2282
     | | ||||||||||||||||||||||||||||||||||| | || |
1811 CATCGCAGGCCACGCCCGGCTTGAAGAAATGCTACCACGAGAAAATGGCA 1860

2283 CTGAGCATCATGAAGGTGGTGGTGGGGCTAGCTCTCCAGTTCCTCTGCAG 2332
     |||||||  ||||| ||| |||||| ||||   |||| |||| |  |||||
1861 ATGAGCATCGCCAAGGTCGTGCTGGGGGTAGCCGCCCAGATCTTGTGCAG 1910

2333 CTATATGACCTTCCCCCTCTACGCGCTCGTCACACAGGTAATAAAACCGT 2382
     :|| ||  ||||||||| ||:||||||||||||||
1911 NTACATCACCTTCCCGCTNTACGCGCTCGTCAC.................1943

2433 AATCATCTGTGTGTGCTGGCTTTGTATGCAGATGGGATCAAACATGAAGA 2482
                                 |||||||| ||| |||||||||
1944 ..........................GCAGATGGGCTCACACATGAAGA 1966

2483 GGTCCATCTTCGACGAGCAGACGTCCAAGGC.GCTCACCAACTGGCGGAA 2531
     |   ||:|||||||||||||||| |||||||  ||| |||||||||||| ||
1967 GAAGCANCTTCGACGAGCAGACGGCCAAGGCGGCTGACCAACTGGCGAAA 2016

2532 CACGGCCAAGGAGAAGAAGAAAGTCCGAGACACGGACATGCTGATGGCTC 2581
     | |||||||||||||||||||| | |||||| ||| ||||||||||||| |
2017 GATGGCCAAGGAGAAGAAGAAGGCCCGAGACGCGGCCATGCTGATGGCGC 2066

2582 AGATGATCGGCGACGCAACACCGAGCCGAGGCTCGTCGCCGATGCCGAGC 2631
     |||||  |||||  ||| ||  ||||||   ||||:|||||||
2067 AGATGGGCGGCGGCGCGACGCCGAGCGTCGGCTNGTCGCCG......... 2107
```

Figure 6D

```
2632 CGGGGCTCATCACCCGTGCACCTGCTTCACAAGGGCATGGGGCGGTCGGA 2681
                    ||||||||||| ||||||| |  || |||||| ||
2108 ...............GTGCACCTGCTCCACAAGGCCGGGGCGCGGTCCGA 2142

2682 CGACCCCCAGAGCGCGCCCACCTCGCCAAGGACCCAGCAGGAGGCTAGGG 2731
     |||||||||||||| |||  | || || ||| || || |||| |   | |
2143 CGACCCCCAGAGCGTGCCGGCGTCCCCGAGGGCCGAGAAGGAAGGCGGCG 2192

2732 ACATGTACCCGGTTGTGGTGGCGCACCCGGTGCACAGACTAAATCCTAAC 2781
     |                 |||  ||| |||| || ||    ||  ||||
2193 GC................GTGCAGCATCCGGCGCGCAAGGTACCTCCTTGT 2227

2782 GACAGGAGGAGGTCCGCCTCGTCGTCGGCCCTCGAAGCCGACATCCCCAG 2831
     ||| || ||||||| ||||||||| |||| ||||| ||  |||||||| |
2228 GACGGGTGGAGGTCGGCCTCGTCGCCGGCGCTCGACGCTCACATCCCCGG 2277

2832 TGCAGATTTTTCCTTCAGC..........CAGGGATGAGACAAGTTTCTG 2871
     |||||||||| |||||||           | ||| ||||||||| ||
2278 TGCAGATTTTGGCTTCAGCACGCAACGTTGACCGATCAGACAAGTTCCTT 2327

2872 TATT 2875
     | ||
2328 TTTT 2331
```

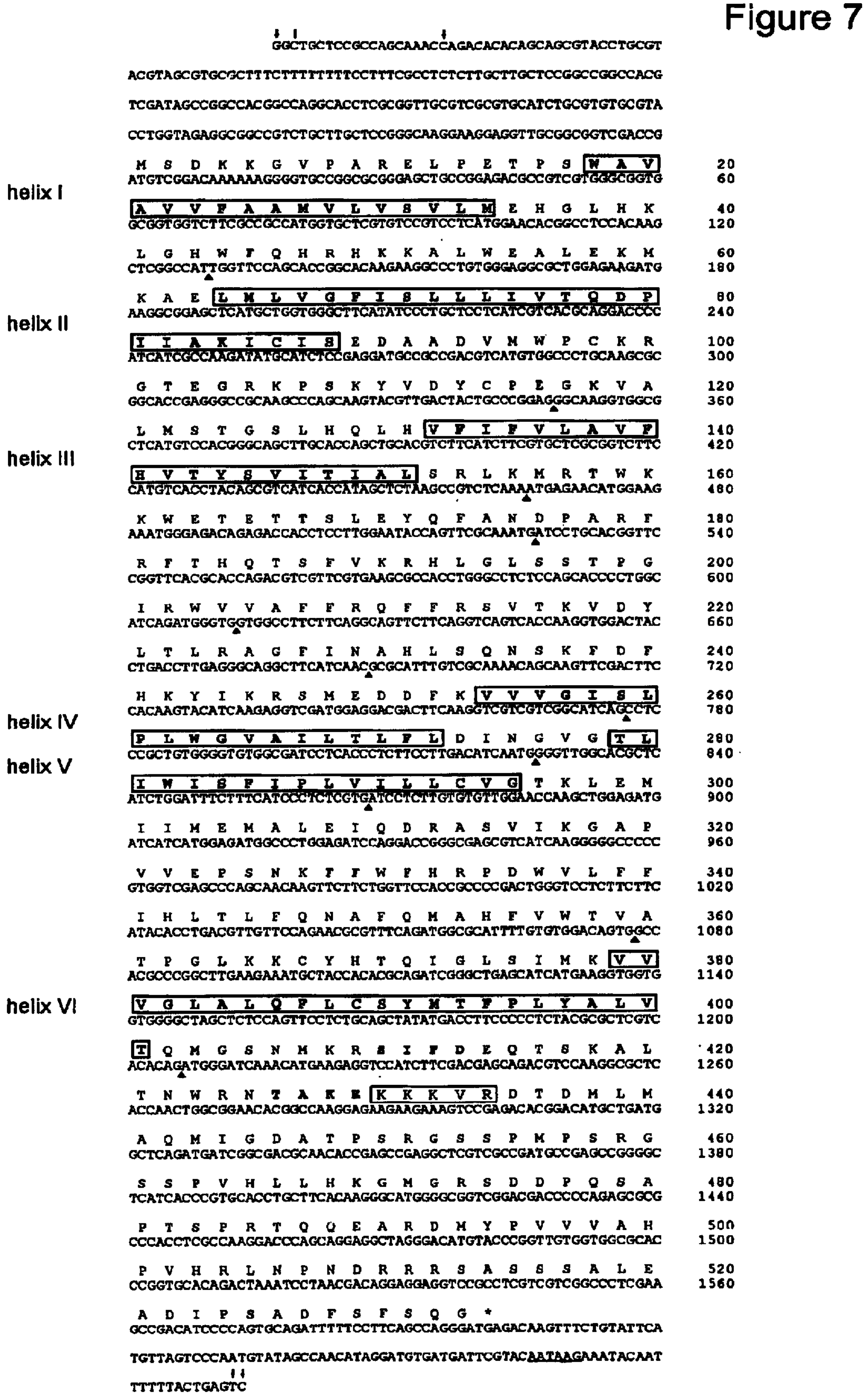

Figure 7

```
                    ↓ ↓                    ↓
                    GGCTGCTCCGCCAGCAAACCAGACACACAGCAGCGTACCTGCGT
           ACGTAGCGTGCGCTTTCTTTTTTTTCCTTTCGCCTCTCTTGCTTGCTCCGGCCGGCCACG
           TCGATAGCCGGCCACGGCCAGGCACCTCGCGGTTGCGTCGCGTGCATCTGCGTGTGCGTA
           CCTGGTAGAGGCGGCCGTCTGCTTGCTCCGGGCAAGGAAGGAGGTTGCGGCGGTCGACCG

                  M  S  D  K  K  G  V  P  A  R  E  L  P  E  T  P  S [W  A  V]    20
                  ATGTCGGACAAAAAAGGGGTGCCGGCGCGGGAGCTGCCGGAGACGCCGTCGTGGGCGGTG    60
helix I
                 [A  V  V  F  A  A  M  V  L  V  S  V  L  M] E  H  G  L  H  K     40
                  GCGGTGGTCTTCGCCGCCATGGTGCTCGTGTCCGTCCTCATGGAACACGGCCTCCACAAG    120

                  L  G  H  W  F  Q  H  R  H  K  K  A  L  W  E  A  L  E  K  M     60
                  CTCGGCCATTGGTTCCAGCACCGGCACAAGAAGGCCCTGTGGGAGGCGCTGGAGAAGATG    180

                  K  A  E [L  M  L  V  G  F  I  S  L  L  L  I  V  T  Q  D  P]    80
                  AAGGCGGAGCTCATGCTGGTGGGCTTCATATCCCTGCTCCTCATCGTCACGCAGGACCCC    240
helix II
                 [I  I  A  K  I  C  I  S] E  D  A  A  D  V  N  W  P  C  K  R    100
                  ATCATCGCCAAGATATGCATCTCCGAGGATGCCGCCGACGTCATGTGGCCCTGCAAGCGC    300

                  G  T  E  G  R  K  P  S  K  Y  V  D  Y  C  P  E  G  K  V  A    120
                  GGCACCGAGGGCCGCAAGCCCAGCAAGTACGTTGACTACTGCCCGGAGGGCAAGGTGGCG    360

                  L  M  S  T  G  S  L  H  Q  L  H [V  F  I  F  V  L  A  V  F]   140
                  CTCATGTCCACGGGCAGCTTGCACCAGCTGCACGTCTTCATCTTCGTGCTCGCGGTCTTC    420
helix III
                 [H  V  T  Y  S  V  I  T  I  A  L] S  R  L  K  M  R  T  W  K    160
                  CATGTCACCTACAGCGTCATCACCATAGCTCTAAGCCGTCTCAAAATGAGAACATGGAAG    480

                  K  W  E  T  E  T  T  S  L  E  Y  Q  F  A  N  D  P  A  R  F    180
                  AAATGGGAGACAGAGACCACCTCCTTGGAATACCAGTTCGCAAATGATCCTGCACGGTTC    540

                  R  F  T  H  Q  T  S  F  V  K  R  H  L  G  L  S  S  T  P  G    200
                  CGGTTCACGCACCAGACGTCGTTCGTGAAGCGCCACCTGGGCCTCTCCAGCACCCCTGGC    600

                  I  R  W  V  V  A  F  F  R  Q  F  F  R  S  V  T  K  V  D  Y    220
                  ATCAGATGGGTGGTGGCCTTCTTCAGGCAGTTCTTCAGGTCAGTCACCAAGGTGGACTAC    660

                  L  T  L  R  A  G  F  I  N  A  H  L  S  Q  N  S  K  F  D  F    240
                  CTGACCTTGAGGGCAGGCTTCATCAACGCGCATTTGTCGCAAAACAGCAAGTTCGACTTC    720

                  H  K  Y  I  K  R  S  M  E  D  D  F  K [V  V  V  G  I  S  L]   260
                  CACAAGTACATCAAGAGGTCGATGGAGGACGACTTCAAGGTCGTCGTCGGCATCAGCCTC    780
helix IV
                 [P  L  W  G  V  A  I  L  T  L  F  L] D  I  N  G  V  G [T  L]   280
                  CCGCTGTGGGGTGTGGCCGATCCTCACCCTCTTCCTTGACATCAATGGGGTTGGCACGCTC    840
helix V
                 [I  W  I  S  F  I  P  L  V  I  L  L  C  V  G] T  K  L  E  M    300
                  ATCTGGATTTCTTTCATCCCTCTCGTGATCCTCTTGTGTGTTGGAACCAAGCTGGAGATG    900

                  I  I  M  E  M  A  L  E  I  Q  D  R  A  S  V  I  K  G  A  P    320
                  ATCATCATGGAGATGGCCCTGGAGATCCAGGACCGGGCGAGCGTCATCAAGGGGGCCCCC    960

                  V  V  E  P  S  N  K  F  F  W  F  H  R  P  D  W  V  L  F  F    340
                  GTGGTCGAGCCCAGCAACAAGTTCTTCTGGTTCCACCGCCCCGACTGGGTCCTCTTCTTC    1020

                  I  H  L  T  L  F  Q  N  A  F  Q  M  A  H  F  V  W  T  V  A    360
                  ATACACCTGACGTTGTTCCAGAACGCGTTTCAGATGGCGCATTTTGTGTGGACAGTGGCC    1080

                  T  P  G  L  K  K  C  Y  H  T  Q  I  G  L  S  I  M  K [V  V]   380
                  ACGCCCGGCTTGAAGAAATGCTACCACACGCAGATCGGGCTGAGCATCATGAAGGTGGTG    1140
helix VI
                 [V  G  L  A  L  Q  F  L  C  S  Y  M  T  F  P  L  Y  A  L  V]   400
                  GTGGGGCTAGCTCTCCAGTTCCTCTGCAGCTATATGACCTTCCCCCTCTACGCGCTCGTC    1200

                 [T] Q  M  G  S  N  H  K  R  S  I  F  D  E  Q  T  S  K  A  L    420
                  ACACAGATGGGATCAAACATGAAGAGGTCCATCTTCGACGAGCAGACGTCCAAGGCGCTC    1260

                  T  N  W  R  N  T  A  K  E [K  K  K  V  R] D  T  D  M  L  M    440
                  ACCAACTGGCGGAACACGGCCAAGGAGAAGAAGAAAGTCCGAGACACGGACATGCTGATG    1320

                  A  Q  M  I  G  D  A  T  P  S  R  G  S  S  P  M  F  S  R  G    460
                  GCTCAGATGATCGGCGACGCAACACCGAGCCGAGGCTCGTCGCCGATGCCGAGCCGGGGC    1380

                  S  S  P  V  H  L  L  H  K  G  M  G  R  S  D  D  P  Q  S  A    480
                  TCATCACCCGTGCACCTGCTTCACAAGGGCATGGGGCGGTCGGACGACCCCCAGAGCGCG    1440

                  P  T  S  P  R  T  Q  Q  E  A  R  D  M  Y  P  V  V  V  A  H    500
                  CCCACCTCGCCAAGGACCCAGCAGGAGGCTAGGGACATGTACCCGGTTGTGGTGGCGCAC    1500

                  P  V  H  R  L  N  P  N  D  R  R  R  S  A  S  S  S  A  L  E    520
                  CCGGTGCACAGACTAAATCCTAACGACAGGAGGAGGTCCGCCTCGTCGTCGGCCCTCGAA    1560

                  A  D  I  P  S  A  D  F  S  F  S  Q  G  *
                  GCCGACATCCCCAGTGCAGATTTTTCCTTCAGCCAGGGATGAGACAAGTTTCTGTATTCA

           TGTTAGTCCCAATGTATAGCCAACATAGGATGTGATGATTCGTACAATAAGAAATACAAT
                                    ↓ ↓
           TTTTTACTGAGTC
```

Figure 8A

```
1    GAATTCAATT AAGGACAACA ACGGATGATA GGCTTAAGCT AGAGAGGATT
51   CATATGGATT AATTAACTGT ACTTAAGTTG AGGTAAAACT CTATCGATTG
101  CTTTGGACAC CGGCTCTCCC ATGATCTGCC AAGTTGAGCC GGCCTACCTA
151  ATTTTCTTCG AAAGCACACA ACAAACGAAG GTAACCACTA ATCTAGACAC
201  CACGCCTAAG TTATCAATTA CTACTCTAGT CTCGCGTAGA AACTTCATTC
251  TTTATGGAGA GTGCTAGTAC TAGAGTACTT AATATAATAG TAAGCGACAA
301  ACCCACGACG ATGAGAATGT ACCTCACTTA CGTAAGTCAA TTAAGTCGAA
351  AAGGAAATCT TGAACACTTA CTTTATTAAA GAAGTATTCC CCGAGGTACA
401  GGAGAGGAGA GCACGCCAAT AACTCCAGCA CTCCTCCGAA ACCTTTCTCA
451  CTCTCTACCC TTTTTCTCCA CACAACTAAA ATGATGTCTA ATGTATGAAA
501  GTGAGTTGTA CTCTATTTTG TTGTGTGTTT GGAAGTGAAA TTAGCTCATC
551  CTTTTATAGC AGCTTAATGG TCGGTTGTAG GTTGGTAGTT AAGTCGGTAA
601  ACACTCACAA CCACCATCGT CAACCAATAG GAGATCGCCA CATGATCGAA
651  AGCTGACAGT TAGGGGTGCC AACCCTGTTT TGTCCGAACC AAGCAAACAA
701  CCTCTAGCTA GGACCTCTCT TCTATGTCTG ACAAGTCGGC CCATATGGCG
751  GTGCACTATG GATTAGGTCA ATTTCAGTCG TTTTGGACTG TCATGTGGGC
801  CCTTCCAATC CTTGTGCTCC CATATGATTG GTCGAAGGTA CATTTAATTC
851  CTGGGTGAGT GCTAGAACTA ATATGATAGA TGTGCTCGGG CTCCTGGGAA
901  AGAGGCCACT TGACATACTT GGGGTAGTGC CCCAAGGGTA TTCCCTATCG
951  CTTTTTCATA ATTTTCTCTC TCCAAAATCG GACGGAAACA ATAAAAAAGA
1001 GAGGCGATGT TCATCGGCAA ATATCTATTT TTTTGATAGT GTCTTCCCTT
1051 AAAACTTGAT TTTTGCGAAG ACTTCCGGCT AAAACCATGA AATCAGAGTT
1101 CCTTGTAACA AATTTAATTT GCCTAAATAC AAAAAAGATC GAATGGAGAT
1151 AGCATTAAAC TTGCTCCATA CGAATCATAT TAGTTGGACC GTAACTCATA
1201 GAAAAAGTTG CAAGTTGGTT GACCTATCAA CCCTCTTATG TTGACCCGTA
1251 AACCCTGTTA TGCATTAAGG ATTAAGTACC CGGCAGATCG TCACTACTCA
1301 CGAATGCACA AATTTCCGGT ACGTAGGATG GGATGAGTTG GTCAGAAACG
1351 GGCTCACCAC GTCGCCCAAC CTGCCGCGAT CGAGCCATTG GCCGGCGATG
1401 CACGCGCTTT GACACAGCCG CCCGCCGCCC CCCGGCCCGC CCCCGCTCTT
```

Figure 8B

1451 TAATAAAAAC CGGCCGCCCC CTGTCAAAGG TGTCAAAGTG TCAAGTGCAT
1501 CAGAGCTAAG CTAGCGGTCA CCCAGTCAGC TCACCCCGAG ACGCACCAGG
1551 GGATCTATCG GATCATGGCA GGTGGGAGAT CGGGATCGCG GGAGTTGCCG
1601 GAGACGCCGA CGTGGGCGGT GGCCGTCGTC TGCGCCGTCC TCGTGCTCGT
1651 CTCCGCCGCC ATGGAGCACG GCCTCCACAA CCTCAGCCAT GTACGCGCGC
1701 GCGCACGCGG TGTGCTCATC TCTCGAGTTA ATTTGGTTGT TGTTGTTGTT
1751 GTGTTCTTGT GACATCTCAA TTAACATCCG ATCCTGGTCG ATCGATCGCC
1801 CTGTGGTGGC GCTACTGCTT GCATTGCAGT GGTTCCGTAG GCGGCAGAAG
1851 AAGGCCATGG GCGACGCCCT CGACAAGATC AAAGCAGGTC ACCCTCAGCC
1901 TCAGCTCACC CTCAGCCTCC ATCTCTAAAT ATTTGACGCC GTTGACTTTT
1951 TTAAATATGT TTGACCATTC GTCTTATTTA AAAAATTTAA GTAATTATTA
2001 ATTCTTTTTC TACCATTTGA TTCATTGCTA AATATACTAT TATGTATACA
2051 TATAGTTTTA CATATTTCAC TAAAGTTTTT AAATAAGACG AATGGTCAAA
2101 CATGTTTAAA AAAGTCAACG GCGTCAAACA TTTAGGAAGA AGAGAATATT
2151 ATATTGCTGC TCCCCTCTAG CCACTTTGCT GCCTCCCTCG TCATTTTTTC
2201 AAGTATTTTA CGCAAGACTG GGTCCTCCAA ATCAAACGTC ACAAATAAGC
2251 CATTTATAGT TTCCTTTCGC TTTTTAAGGG GGGACTACTT GTATTTAATC
2301 ATGGAGGAAA CTACCAGTCG GATGTCCGAT TACTTAAAAA AAAATTCGGG
2351 GGACTAATTT TTTTGGCTGA TCATCGGTGA AATATTAGGT TATATATGTT
2401 GAAAAAAAAT CAGCCACAAA CAATGAAATA TTTTGTGAAA CACATATTAG
2451 ACACGTTGAA ACGTATCATT GTTACGTATA AAACATCGAA TGTTAACAGA
2501 TTAAAACATA TGTTTTTTTT TAATCAGAAT ATAATCATGC GATATATTAT
2551 TGTAAAGATA TAATTACAAC GAATACAACA GTGCGATCGG ATTATATATA
2601 TATTAGTAGT TTAAGAGAAA AATCATTTTG AAGATTACTA GATACATACA
2651 CGTATAGATG GATGAAGTGG AGAGAGATTA GAGATAAGTA GTTATATGAA
2701 TTTTGTGAAA CACACTTAAG ACATATGTTC AAACATACTG CTATTATGTA
2751 TGAAATATTG AGTTTTAACG GTTTAAAACA CATATTCTTT TAATTAGAAT
2801 GTAATAATGT GATATCTTGT TGTAAAATTT AATTACATCT AATATAACGG
2851 TGTGATTAGA TTGTATGTTG GATAACATGC CCATCGGTTG GCTTATTTAG
2901 GGAATAAGCC AAATGGTATA TTTGCAAACG AAAAATAATT TGTAAATAAA
2951 ACTTTTATGT ATGTATTCTT AACGATCTAG CAGCAAAGGC TGAAAAATAA
3001 ACTTCGATGA AAAATCTCAA AATCAACTCT TAAAATTTAA ATTTTGGCTT

Figure 8C

3051 ATAAGTATAG TTCCTAACTA GTTTAGAAGA AAAAATATTT AAAGCGGGGA
3101 AGAGGAAAAG GAATAAACTA ATAGCTAAAT TATTGCATGC ATGTAGCGAT
3151 TTGAGGACGA CCGAGTTGTT TTGTCTGGAT CAGCCGACCG AGACAGAGCA
3201 ATCTTCTTTA ATCATAAATA ACCAGAAAAA CCATACCAGT TCATCACAAT
3251 GGACCGAGTC AGAGTCATTA CATATTTTTC ATTGTTGCGC ACAGGATTCA
3301 CCATGTTCTT ATGGGAAATA TTTTTAACTC TCAAATGGTT ATGATTTTGA
3351 ACTCTCATTT TTGAGAGAGA ATTAACAAGC GAGCGAGCAA TCAGGCCAAA
3401 AAGGGAGAAA GAAAATTATT TTTGTTAATT TTTTTTTAAG GTAGGGTGGA
3451 GGAGTCATTA CATGATTTTT TTTTATATTC CCTCGTTGAT TATATGCTGT
3501 TCAAATGGTT ATGATTTTTT TAAAAGATAA CAACAATACA AATTAGTATG
3551 TGATAGATCA TTTCACGAGC ATATAGGATT AAATTTAACT TCTGTAAATT
3601 ACAAAACAAA CAAGTTTAAC TGTTAATATA CATTAAATTT GTTTTTTTCA
3651 ACTTAGGAAT TGAATTTTAT GTATATATTT GTAAAATGAT ATATTAATTT
3701 ATTTTTTTAA AAAAATAATT ATTTAGATAA CACGCAAACT AGAAAACCAC
3751 CGCAGAAGTT CTCATATTTC TTGTCCTATC TGCACTTGCA GAGCTGATGC
3801 TGCTGGGCTT CATATCCCTG CTTCTCACCG TGGCACAGGC GCCCATCTCC
3851 AAGATCTGCA TCCCCAAGTC GGCTGCCAAC ATCTTGTTGC CGTGCAAGGC
3901 AGGCCAAGAT GCCATCGAAG AAGAAGCAGC AAGTGGTCGC CGGTCCTTGG
3951 CCGGCGCCGG CGGCGGGGAC TACTGCTCGA AATTCGATGT GAGAATAACA
4001 CCAGCTGCCG GCAAGCACAA CCTCGATGCA ATAACTAATT TAACTATAAT
4051 TGATTTTTCT TGGGTTTTCT GCAGGGCAAG GTGGCGCTGA TGTCGGCAAA
4101 GAGCATGCAC CAGCTGCACA TTTTCATCTT CGTGCTCGCC GTGTTCCATG
4151 TTACCTACTG CATCATCACC ATGGGTTTAG GGCGCCTCAA AGTGAGTTTG
4201 TCGTTCTGTC CCTCATGCAC ATGTTTTCTC TAGTTCTAGC AAGATTGTCA
4251 GTCCTTCAAA TGGATTGTTT CGACAAGAAA CCCAATTTAT TAATTTGCCA
4301 GTAAATATAT AATAATTGAT CTTTCTTGGT TTTAGATGAA GAAATGGAAG
4351 AAGTGGGAGT CACAGACCAA CTCATTGGAG TATCAGTTCG CAATCGGTAG
4401 TGAATTAAGA ATCTCCCTAA CTATTTCATT TCAGAACCTT TATGATAATG
4451 TCTTGAAAGA GGAGGAGCAA ATCAGCTGAA AAATATGATC GATCCATGCA
4501 GATCCTTCAC GATTCAGGTT CACGCATCAG ACGTCGTTCG TGAAGCGGCA
4551 TCTGGGATCA TTCTCAAGCA CCCCTGGGCT CAGATGGATC GTGAGTTATC
4601 AATCTCCGAA TACATGCTTG TTTTTTATTC TTGCAACTGG CCTAGCTGTT

Figure 8D

4651 CCAATTCAAT CCATATTTTT TGAAAAAAAA AATATTCATG CCGTGTTTGT
4701 TGTTAGGTAG CATTCTTCAG GCAGTTCTTT GGGTCCGTCA CCAAGGTGGA
4751 CTACCTGACC ATGCGGCAAG GCTTCATCAA TGTATATACT AATCAAACCT
4801 GACCAATTCA ACATTGATGA TGCAAACAGA GACCAGGTTT TTTTTTTCGA
4851 GTGTGCATTG AGTAATGGTT TTAGCTTCTT CTCTTTTGCA GGCGCATTTG
4901 TCGCAGAATA GCAAGTTCGA CTTCCACAAA TACATCAAGA GGTCTTTGGA
4951 GGACGACTTC AAAGTTGTCG TTGGCATCAG GTCCGTCCTC GCTTTATTAA
5001 TTATAGGACT CTTATATTCA ACATTTTTTT TATAAAGAAA CATATTTAGT
5051 CTCCAGTTGT GTATGTGTAT GTGGATCTTG ACACATTTGG CTGGTTTTGC
5101 AGCCTCCCTC TGTGGTTCGT CGGAATCCTT GTACTCTTCC TCGATATCCA
5151 CGGTAATCCT TGTCCTATTT CATTCTTTTT TTTACTCTCA AAACCTTGTT
5201 CTGAATTGGT CTTATAATCA CCATCGATTT TTTTTCAACT TTTTCCCCGC
5251 GTGTAGGTCT TGGCACACTT ATTTGGATCT CTTTTGTTCC TCTCATCGTA
5301 AGAGCGAAAT TTCCCTGTCC AAAGAAACAG TTAACATAAT TAATTATGCT
5351 TTAATTTATC ATGAAAATTA ATATGATCAT ATAACTAATG AACAAACATT
5401 CATGTGAATG CCACCGTTGT CTCAGATCGT CTTGTTAGTT GGGACCAAGC
5451 TAGAGATGGT GATCATGGAG ATGGCCCAAG AGATACAGGA CAGGGCCACT
5501 GTGATCCAGG GAGCACCTAT GGTTGAACCA AGCAACAAGT ACTTCTGGTT
5551 CAACCGCCCT GACTGGGTCT TGTTCTTCAT ACACCTGACA CTCTTCCATG
5601 TACATGTTTA AAACCTAAAC CTTGCTGCTC AACTACAAAT AGTACTTTAT
5651 CTTTCACAAT TAACACCTAA TTAACTAACA TAGCATCCAT CCATTTGTGG
5701 CTACTGATCG ATGGGACGAC GGATCGATCA TCACCAGAAC GCATTTCAGA
5751 TGGCGCATTT CGTATGGACT ATGGTGTGTA TGCTACTTGC TTAGTTGTTG
5801 CCATTATCAG TTCTTAAGCA AATTAAGTGT GATGCATGCA CTGACTAATG
5851 AGACAAAAAA TGACACAGCT TGTTCATCGA TCTGGTTGTT TTGTGTGTGA
5901 CAGGCAACAC CTGGTCTGAA GAAATGCTTC CATGAAAATA TTTGGCTGAG
5951 CATCGTGGAA GTCATTGTGG GGATCTCTCT TCAGGTGCTA TGCAGCTACA
6001 TCACCTTCCC GCTCTACGCG CTCGTCACAC AGGTGAACAA GCCATTCACA
6051 AATTCTATTA GCCGTTTCTT AATTGATGAC ACTGTTAATT TTTAGACACA
6101 CGTTTTGACC ATTTGTCTTA TTAAAAATAT TTATGTAATT ATCATTTGAG
6151 TTGTTTTATC ACTAAAAGTA CTTTTTAAAT AATTTATATT TTGCATTTGT
6201 ACAATTCTTT TAATAAGATA ATGGTCAAAC ATGTGTCCAA AAGTTAACAG

Figure 8E

6251 CATCATCTAT TAAGAAAAGG AGGGGTTTTT TTTTTTTGGA ATTTTGCAAA

6301 ATTTGTTCAA AATCAGTCCA AAACCTTTTT TTTTTTCGAA ATTTCAGTTT

6351 CACTACCAGT CCCCATAAAA TGTCTTTTCT TTATTTCCAC AAGATTGAAC

6401 CCATGAGATG CCCTTTGTGT TGGTATGTGT TTTGGCCATC ACTTGCAGAT

6451 GGGATCGAAC ATGAAGAAGA CAATTTTCGA GGAGCAAACG ATGAAGGCGC

6501 TGATGAACTG GAGGAAGAAG GCGATGGAGA AGAAGAAGGT CCGGGACGCC

6551 GACGCGTTCC TGGCGCAGAT GAGCGTCGAC TTCGCGACGC CGGCGTCGAG

6601 CCGGTCCGCG TCGCCGGTGC ACCTGCTGCA GGATCACAGG GCGAGGTCGG

6651 ACGACCCGCC GAGCCCAATC ACGGTGGCCT CACCACCGGC ACCGGAGGAG

6701 GACATGTACC CGGTGCCGGC GGCGGCTGCG TCTCGCCAGC TGCTAGACGA

6751 CCCGCCGGAC AGGAGGTGGA TGGCATCCTC GTCGGCCGAC ATCGCCGATT

6801 CTGATTTTTC CTTCAGCGCA CAACGGTGAC GGGGGCGATC GGTTTCTGTA

6851 TTGATGCTGT ACCAAACATA GGAGTTTAAT ATATATATAA TTGTTACGGT

6901 AAAATCTAAT TATTGTGCGC GCACTTATAT TAGTCTTATA GCGCGACTGG

6951 TTCGTGATTA GACAAGGTGA TGCATGCTGT TTAGTTATAA AGGATATCAG

7001 CGCAGCTAAA AAAACTTACT CCCTACTTAA TAGATGACCT CGTTGATTTT

7051 TAACATTATT CGTCTTATTT AAAAAATTTA TGCAAATGTT TAAAACATAA

7101 ATCATGCTTA AAGTACTTTT AGTGATAAAA CAACTTACAA CAAAATAAAT

7151 TATAGTTACC TAATTTTTTT TAATAAATCG AATGG

Figure 9A

1 TTATACCATG TGAGAAAGGC TGGAAGCATA TGCTCTTAGC AGGGACGCGT
51 GCATGTTTAT ATAGGAGGCA TAAGCCGAAG AGATATACAT GAGGAGAGGT
101 TTAAGATCAG TCTATCTTAT TTACAGTTTA AACACAAGGA GATAGAAAGA
151 GATCCTAACC TACACATGTT ATACAAGTCA CGTATAATAC AAGAGTTATT
201 TCGTCTAACA CCCTCCCCTC TGATATGATA AGTCGCCGGG AGAGAGAGAG
251 AGTGTGTGGC TGCCCTCGCT GCACTGCACG CACATGTTTA CTTCTCCGAC
301 TGAAACCACG GTGAAACCGG CGGCGGTGTC GCACTCCCCT GACTTTCCTC
351 GCCGGGGTCC CGTCCGGACA ATTAAACCGT CTGTACCTGC CGGGCGTCGA
401 CCCGATCGTG ATGTGGCGCC GCTTTGTCTG CAGCGAGCTG CGTGGCCGAT
451 GGCAACAAAA CTGCGGTCAC ATACATGCAT ACCCCGCATA CCCCGACGCT
501 CACCAGTAAG TAGGCTGTGG TGCGGCACCA CGGGCTCGCC GCCATTCATG
551 CCATGCATGG GCCACCCGCC GGCGAAACCG CGGCGCTGCT GCCTGCCACC
601 CCGCCGCCGT TGACGAAGAC TTCGCCCGGC CATCCATAAA AGCATGCATG
651 GCTTGCTCTC ACCGGTCCGG CCACACACAC CACACTTCAC TTCGCCATTC
701 GCACCACCGA GAGCGTAGCG TAACGTGTGT TTGAAGTCCT ACCATTAATT
751 TTGCTGGATC GATGGCTGGG CCGGCGGGAG GTCGGGAGCT GTCGGACACG
801 CCGACGTGGG CGGTGGCGGT AGTCTGCGCC GTCATGATAC TCGTCTCCGT
851 CGCCATGGAG CACGCGCTCC ACAAGCTCGG CCACGTACGT GCTCTCGGTT
901 CACTAGTGCT TAACTGTTTT TGATGTTTTC GGGCGTGTTT GGTAGCCTGC
951 ATGGAGAGTG TATGAGCCCA AAAGTTCCCT CCCCGACCCA CTTTTCGCTG
1001 TTTGGTAGGG TGTATGGGCT GAGGAGAGCA TGCATCAACT GATGCAAAAA
1051 GGGCCTCAGC ATAGCTGAGC CCAGCACCCC CGCAGAGGCG AGCTGAGGCG
1101 AGTTATGCTG AGCCCATGCA CCCTCGCCCC GTCGCCCCGT CGCCCCGTCG
1151 CTCCCCCCCT GCACCTCTTC CTCCTCCCTC TTCCTACCAA ACACAGTCTC
1201 ATCCAAACAT GTAACAACAC ATGCATGACC ACCAAACAAC TGAAGATGAA
1251 TGTATTCATC ATGTCTATAC TTACCATGCA TCAACAGGGA ACAACTATGC
1301 TAGGGTGAGA ACAGCTGCCA AACACACCCG TGCACCTACT CATGCTGTGC
1351 CGGCGCTGGC GTACGTGTGC AGTGGTTCCA CAAGTGGCGC AAGAAGGCCC
1401 TGGGGGAGGC GCTGGAGAAG ATGAAGGCGG AGCTCATGCT GGTGGGCTTC

Figure 9B

1451 ATATCCCTGC TCCTCATCGT CACGCAGGAT CCCGTCTCCA GGATCTGCAT
1501 CTCCAAGGAG GCCGGCGAGA AGATGCTCCC GTGCAAGCCT TACGACGGCG
1551 CCGGCGGTGG CAAAGGCAAG GACAATCACC GGAGGCTTCT CTGGCTCCAA
1601 GGCGAGAGCG AGACCCACCG CCGGTTCCTG GCTGCCCCGG CCGGAGTGGA
1651 CGTCTGCGCC AAACAGGTGA GCACCTAGCG TCGCCACAAA CCACAAACTA
1701 GCTAATGAGC ATGGACCTGA ATTTCTTCTC TTCTTGGCTT GGCTTGACTA
1751 AATTGGTTGT GCAGGGCAAG GTGGCGCTGA TGTCAGCGGG AAGCATGCAC
1801 CAACTGCACA TATTCATCTT CGTGCTCGCC GTCTTCCACG TCTTGTACAG
1851 CGTCGTCACC ATGACCCTAA GCCGTCTCAA AGTGAGCATC ATACTCGAGC
1901 TGTTTGTCAA TAATCCTTGG TTTCCAATCC AATTCCAAAG CTGGCACTGA
1951 TCCTGCTCCG GCTTCCTGCA GATGAAGCAA TGGAAGAAGT GGGAGTCGGA
2001 GACCGCCTCG CTGGAGTATC AGTTCGCGAA TGGTCAGCTT CAACTTTTCT
2051 TACTGAAACC GGATGCATTT ACAACAAACG CACGCACGAT CAATCATCAC
2101 AGTGTGAGCC GATACGTTGA ACCGATTGAA TCCTCGCAGA TCCATCGCGG
2151 TGCCGGTTCA CGCACCAGAC GACGTTGGTG AGGCGGCACC TGGGCCTCTC
2201 CAGCACCCCC GGCGTCAGAT GGGTGGTGGC CTTCTTCAGG CAGTTCTTCA
2251 CGTCGGTGAC CAAGGTGGAC TACCTGACCT TGCGGCAGGG CTTCATCAAC
2301 GCGCATCTCT CGCAGGGCAA CAGGTTCGAC TTCCACAAGT ACATCAAGAG
2351 GTCGTTGGAG GACGACTTCA AAGTCGTCGT CCGCATCAGG TACGCGCCAT
2401 TCCTTTCTCT GCACAAATTA ATACATCCAC CACCACATAG GTAGATAGAT
2451 AGATCGATAG ATAGATTATA CAAGTGCCGG TACGTACGTA CGTCTCATAT
2501 GATCTTGACA CATCTGTCCT CTTGCCGCAG TCTCAAGCTC TGGTTCGTGG
2551 CGGTCCTCAT CCTCTTCCTT GATTTCGACG GTAGCCGCCT TGTCCATGCC
2601 CTGCTCGCCC TCTCCTCCGC TTCTCTCCAT AATTTGTGAA CTTGTCCCGT
2651 ATATAACCAC ACCACCGTCG TCTTCTCGCA GGGATCGGCA CTCTTCTCTG
2701 GATGTCCGTG GTTCCTCTCG TGGTAAGTCC ACAATTTGAA TAGACAACCT
2751 GTCCAATTGT GATGTACAGT ACCTCCAAAC TTAATTAACA TGTCATTTGC
2801 TGATGTCTTG CGTGTAACAT TAGATCCTCT TGTGGGTTGG GACCAAGCTG
2851 GAGATGGTGA TCATGGAGAT GGCCCAGGAG ATCCATGACC GGGAGAGCGT
2901 CGTCAAGGGT GCTCCCGCCG TCGAGCCCAG CAACAAGTAC TTCTGGTTCA
2951 ACCGGCCTGA CTGGGTCCTC TTCCTCATGC ACCTCACACT CTTCCAGAAC
3001 GCGTTTCAGA TGGCTCATTT CGTGTGGACA GTGGTACGTA CAAGTACTTG

Figure 9C

3051 TCACTTCACT TAGGCTAACT CCAACAAACG ACCCCAAATT AATGGTCCGT
3101 CGCGTCTGTT TGGGGTATGT TTGGGGTAAA CGGACACAAA ACTCAATCCA
3151 ACGCGCGGTA GCAAACGAAC GTTTTTCCGT ACGTTTTCGT CCGCTTTCGC
3201 CCCATCCCAG CCCAAATTCG TTGACGTTGT TGCATCGCAG GCCACGCCCG
3251 GCTTGAAGAA ATGCTACCAC GAGAAAATGG CAATGAGCAT CGCCAAGGTC
3301 GTGCTGGGGG TAGCCGCCCA GATCTTGTGC AGCTACATCA CCTTCCCGCT
3351 CTACGCGCTC GTCACGCAGA TGGGCTCACA CATGAAGAGA AGCATCTTCG
3401 ACGAGCAGAC GGCCAAGGCG CTGACCAACT GGCGAAAGAT GGCCAAGGAG
3451 AAGAAGAAGG CCCGAGACGC GGCCATGCTG ATGGCGCAGA TGGGCGGCGG
3501 CGCGACGCCG AGCGTCGGCT CGTCGCCGGT GCACCTGCTC CACAAGGCCG
3551 GGGCGCGGTC CGACGACCCC CAGAGCGTGC CGGCGTCCCC GAGGGCCGAG
3601 AAGGAAGGCG GCGGCGTGCA GCATCCGGCG CGCAAGGTAC CTCCTTGTGA
3651 CGGGTGGAGG TCGGCCTCGT CGCCGGCGCT CGACGCTCAC ATCCCCGGTG
3701 CAGATTTTGG CTTCAGCACG CAACGTTGAC CGATCAGACA AGTTCCTTTT
3751 TTTTTCGGTG AATAGAAGCG TATCATTTCA TTGATAGACA GTAGAAATTA
3801 CAGGAATGGC TGTCCTACTA CTATGTACAC AAGGGCACAG CAAAGGATCA
3851 TTGATCTTGT TACAAGAGCA GTAGAAAGGG ATTGCTCTCC ATTGATCTTG
3901 TTAAGTTGTA TGTCACAAAT TGTTGCAGAA AAAAGTGTAT GTCATCCCAA
3951 CCAAGAGCTG AGTTTGTGAT GATTCGTGCA ATAAGAATTG CAAGTTTCAC
4001 CGAGTCAAAA ATGAAGCTTC TAAGTACGCA CCAACCAACG GACTCTTTCA
4051 TCTCAACAAA AGAACTGTAA ATGGCAATAA TTCTGATAAC ATCGGAAGGG
4101 AGCTC

Figure 10

1 ATGGCAGGTG GGAGATCGGG ATCGCGGGAG TTGCCGGAGA CGCCGACGTG
51 GGCGGTGGCC GTCGTCTGCG CCGTCCTCGT GCTCGTCTCC GCCGCCATGG
101 AGCACGGCCT CCACAACCTC AGCCATAAAA CCACCGCAGA AGTTCTCATA
151 TTTCTTGTCC TATCTGCACT TGCAGAGCTG ATGCTGCTGG GCTTCATATC
201 CCTGCTTCTC ACCGTGGCAC AGGCGCCCAT CTCCAAGATC TGCATCCCCA
251 AGTCGGCTGC CAACATCTTG TTGCCGTGCA AGGCAGGCCA AGATGCCATC
301 GAAGAAGAAG CAGCAAGTGG TCGCCGGTCC TTGGCCGGCG CCGGCGGCGG
351 GGACTACTGC TCGAAATTCG ATGGCAAGGT GGCGCTGATG TCGGCAAAGA
401 GCATGCACCA GCTGCACATT TTCATCTTCG TGCTCGCCGT GTTCCATGTT
451 ACCTACTGCA TCATCACCAT GGGTTTAGGG CGCCTCAAAA TGAAGAAATG
501 GAAGAAGTGG GAGTCACAGA CCAACTCATT GGAGTATCAG TTCGCAATCG
551 ATCCTTCACG ATTCAGGTTC ACGCATCAGA CGTCGTTCGT GAAGCGGCAT
601 CTGGGATCAT TCTCAAGCAC CCCTGGGCTC AGATGGATCG TAGCATTCTT
651 CAGGCAGTTC TTTGGGTCCG TCACCAAGGT GGACTACCTG ACCATGCGGC
701 AAGGCTTCAT CAATGCGCAT TTGTCGCAGA ATAGCAAGTT CGACTTCCAC
751 AAATACATCA AGAGGTCTTT GGAGGACGAC TTCAAAGTTG TCGTTGGCAT
801 CAGCCTCCCT CTGTGGTTCG TCGGAATCCT TGTACTCTTC CTCGATATCC
851 ACGGTCTTGG CACACTTATT TGGATCTCTT TTGTTCCTCT CATCATCGTC
901 TTGTTAGTTG GGACCAAGCT AGAGATGGTG ATCATGGAGA TGGCCCAAGA
951 GATACAGGAC AGGGCCACTG TGATCCAGGG AGCACCTATG GTTGAACCAA
1001 GCAACAAGTA CTTCTGGTTC AACCGCCCTG ACTGGGTCTT GTTCTTCATA
1051 CACCTGACAC TCTTCCATAA CGCATTTCAG ATGGCGCATT TCGTATGGAC
1101 TATGGCAACA CCTGGTCTGA AGAAATGCTT CCATGAAAAT ATTTGGCTGA
1151 GCATCGTGGA AGTCATTGTG GGGATCTCTC TTCAGGTGCT ATGCAGCTAC
1201 ATCACCTTCC CGCTCTACGC GCTCGTCACA CAGATGGGAT CGAACATGAA
1251 GAAGACAATT TTCGAGGAGC AAACGATGAA GGCGCTGATG AACTGGAGGA
1301 AGAAGGCGAT GGAGAAGAAG AAGGTCCGGG ACGCCGACGC GTTCCTGGCG
1351 CAGATGAGCG TCGACTTCGC GACGCCGGCG TCGAGCCGGT CCGCGTCGCC
1401 GGTGCACCTG CTGCAGGTCA CAGGGCGGGT CGGACGCCCG CCGAGCCCAA
1451 TCACGGTGGC CTCACCACCG GCACCGGAGG AGGACATGTA CCCGGTGCCG
1501 GCGGCGGCTG CGTCTCGCCA GCTGCTAGAC GACCCGCCGG ACAGGAGGTG
1551 GATGGCATCC TCGTCGGCCG ACATCGCCGA TTCTGATTTT TCCTTCAGCG
1601 CACAACGGTG A

Figure 11

```
1    ATGGCTGGGC CGGCGGGAGG TCGGGAGCTG TCGGACACGC CGACGTGGGC
51   GGTGGCGGTA GTCTGCGCCG TCATGATACT CGTCTCCGTC GCCATGGAGC
101  ACGCGCTCCA CAAGCTCGGC CACTGGTTCC ACAAGTGGCG CAAGAAGGCC
151  CTGGGGGAGG CGCTGGAGAA GATGAAGGCG GAGCTCATGC TGGTGGGCTT
201  CATATCCCTG CTCCTCATCG TCACGCAGGA TCCCGTCTCC AGGATCTGCA
251  TCTCCAAGGA GGCCGGCGAG AAGATGCTCC CGTGCAAGCC TTACGACGGC
301  GCCGGCGGTG GCAAAGGCAA GGACAATCAC CGGAGGCTTC TCTGGCTCCA
351  AGGCGAGAGC GAGACCCACC GCCGGTTCCT GGCTGCCCCG GCCGGAGTGG
401  ACGTCTGCGC CAAACAGGGC AAGGTGGCGC TGATGTCAGC GGGAAGCATG
451  CACCAACTGC ACATATTCAT CTTCGTGCTC GCCGTCTTCC ACGTCTTGTA
501  CAGCGTCGTC ACCATGACCC TAAGCCGTCT CAAAATGAAG CAATGGAAGA
551  AGTGGGAGTC GGAGACCGCC TCGCTGGAGT ATCAGTTCGC GAATGATCCA
601  TCGCGGTGCC GGTTCACGCA CCAGACGACG TTGGTGAGGC GGCACCTGGG
651  CCTCTCCAGC ACCCCCGGCG TCAGATGGGT GGTGGCCTTC TTCAGGCAGT
701  TCTTCACGTC GGTGACCAAG GTGGACTACC TGACCTTGCG GCAGGGCTTC
751  ATCAACGCGC ATCTCTCGCA GGGCAACAGG TTCGACTTCC ACAAGTACAT
801  CAAGAGGTCG TTGGAGGACG ACTTCAAAGT CGTCGTCCGC ATCAGTCTCA
851  AGCTCTGGTT CGTGGCGGTC CTCATCCTCT TCCTTGATTT CGACGGGATC
901  GGCACTCTTC TCTGGATGTC CGTGGTTCCT CTCGTGATCC TCTTGTGGGT
951  TGGGACCAAG CTGGAGATGG TGATCATGGA GATGGCCCAG GAGATCCATG
1001 ACCGGGAGAG CGTCGTCAAG GGTGCTCCCG CCGTCGAGCC CAGCAACAAG
1051 TACTTCTGGT TCAACCGGCC TGACTGGGTC CTCTTCCTCA TGCACCTCAC
1101 ACTCTTCCAG AACGCGTTTC AGATGGCTCA TTTCGTGTGG ACAGTGGCCA
1151 CGCCCGGCTT GAAGAAATGC TACCACGAGA AAATGGCAAT GAGCATCGCC
1201 AAGGTCGTGC TGGGGGTAGC CGCCCAGATC TTGTGCAGCT ACATCACCTT
1251 CCCGCTCTAC GCGCTCGTCA CGCAGATGGG CTCACACATG AAGAGAAGCA
1301 TCTTCGACGA GCAGACGGCC AAGGCGCTGA CCAACTGGCG AAAGATGGCC
1351 AAGGAGAAGA AGAAGGCCCG AGACGCGGCC ATGCTGATGG CGCAGATGGG
1401 CGGCGGCGCG ACGCCGAGCG TCGGCTCGTC GCCGGTGCAC CTGCTCCACA
1451 AGGCCGGGGC GCGGTCCGAC GACCCCCAGA GCGTGCCGGC GTCCCCGAGG
1501 GCCGAGAAGG AAGGCGGCGG CGTGCAGCAT CCGGCGCGCA AGGTACCTCC
1551 TTGTGACGGG TGGAGGTCGG CCTCGTCGCC GGCGCTCGAC GCTCACATCC
1601 CCGGTGCAGA TTTTGGCTTC AGCACGCAAC GTTGA
```

Figure 12A

```
   1 GTTGGTACAT AAAAGACTCT TCCTTTGTCT GTTTTTTGTT CCCAGATTCA
  51 TCTTTACTTA TTGACTAAAT TCTCTCTGGT GTGAGAAGTA AAATGGGTCA
 101 CGGAGGAGAA GGGATGTCGC TTGAATTCAC TCCGACGTGG GTCGTCGCCG
 151 GAGTTTGTAC GGTCATCGTC GCGATTTCAC TGGCGGTGGA GCGTTTGCTT
 201 CACTATTTCG GTACTGTTCT TAAGAAGAAG AAGCAAAAAC CCCTTTACGA
 251 AGCCCTTCAA AAGGTTAAAG AAGAGCTGAT GTTGTTAGGG TTTATATCGC
 301 TGTTACTGAC GGTATTCCAA GGGCTCATTT CCAAATTCTG TGTGAAAGAA
 351 AATGTGCTTA TGCATATGCT TCCATGTTCT CTCGATTCAA GACGAGAAGC
 401 TGGGGCAAGT GAACATAAAA ACGTTACAGC AAAAGAACAT TTTCAGACTT
 451 TTTTACCTAT TGTTGGAACC ACTAGGCGTC TACTTGCTGA ACATGCTGCT
 501 GTGCAAGTTG GTTACTGTAG CGAAAAGGGT AAAGTACCAT TGCTTTCGCT
 551 TGAGGCATTG CACCATCTAC ATATTTTCAT CTTCGTCCTC GCCATATCCC
 601 ATGTGACATT CTGTGTCCTT ACCGTGATTT TTGGAAGCAC AAGGATTCAC
 651 CAATGGAAGA AATGGGAGGA TTCGATCGCA GATGAGAAGT TTGACCCCGA
 701 AACAGCTCTC AGGAAAAGAA GGGTCACTCA TGTACACAAC CATGCTTTTA
 751 TTAAAGAGCA TTTTCTTGGT ATTGGCAAAG ATTCAGTCAT CCTCGGATGG
 801 ACGCAATCCT TTCTCAAGCA ATTCTATGAT TCTGTGACGA AATCAGATTA
 851 CGTGACTTTA CGTCTTGGTT TCATTATGAC ACATTGTAAG GGAAACCCCA
 901 AGCTTAATTT CCACAAGTAT ATGATGCGCG CTCTAGAGGA TGATTTCAAA
 951 CAAGTTGTTG GTATTAGTTG GTATCTTTGG ATCTTTGTCG TCATCTTTTT
1001 GCTGCTAAAT GTTAACGGAT GGCACACATA TTTCTGGATA GCATTTATTC
1051 CCTTTGCTTT GCTTCTTGCT GTGGGAACAA AGTTGGAGCA TGTGATTGCA
1101 CAGTTAGCTC ATGAAGTTGC AGAGAAACAT GTAGCCATTG AAGGAGACTT
1151 AGTGGTGAAA CCCTCAGATG AGCATTTCTG GTTCAGCAAA CCTCAAATTG
1201 TTCTCTACTT GATCCATTTT ATCCTCTTCC AGAATGCTTT TGAGATTGCG
```

Figure 12B

1251 TTTTTCTTTT GGATTTGGGT TACATACGGC TTCGACTCGT GCATTATGGG
1301 ACAGGTGAGA TACATTGTTC CAAGATTGGT TATCGGGGTC TTCATTCAAG
1351 TGCTTTGCAG TTACAGTACA CTGCCTCTTT ACGCCATCGT CTCACAGATG
1401 GGAAGTAGCT TCAAGAAAGC TATATTCGAG GAGAATGTGC AGGTTGGTCT
1451 TGTTGGTTGG GCACAGAAAG TGAAACAAAA GAGAGACCTA AAAGCTGCAG
1501 CTAGTAATGG AGACGAAGGA AGCTCTCAGG CTGGTCCTGG TCCTGATTCT
1551 GGTTCTGGTT CTGCTCCTGC TGCTGGTCCT GGTGCAGGTT TTGCAGGAAT
1601 TCAGCTCAGC AGAGTAACAA GAAACAACGC AGGGGACACA AACAATGAGA
1651 TTACACCTGA TCATAACAAC TGAGCAGAGA TATTATCTTT TCCATTTAGA
1701 GGATCATCAT CAGATTTTAG CTTCAAGGTC CGGTTTTGTG GTTTATACAT
1751 AAGTTATAGT GACTTGATTT TTTTGTTTTG TTACAAAGTT ACCATCTTTG
1801 GATTAGAATT GGGAAATTGA ATCTGTTTGT ATATTGTATT ATTTGGAACA
1851 TTGTGGATGC CCATGGATAT GTTTCTGTTC

Figure 13

1 MAGGRSGSRE LPETPTWAVA VVCAVLVLVS AAMEHGLHNL SHKTTAEVLI

51 FLVLSALAEL MLLGFISLLL TVAQAPISKI CIPKSAANIL LPCKAGQDAI

101 EEEAASGRRS LAGAGGGDYC SKFDGKVALM SAKSMHQLHI FIFVLAVFHV

151 TYCIITMGLG RLKMKKWKKW ESQTNSLEYQ FAIDPSRFRF THQTSFVKRH

201 LGSFSSTPGL RWIVAFFRQF FGSVTKVDYL TMRQGFINAH LSQNSKFDFH

251 KYIKRSLEDD FKVVVGISLP LWFVGILVLF LDIHGLGTLI WISFVPLIIV

301 LLVGTKLEMV IMEMAQEIQD RATVIQGAPM VEPSNKYFWF NRPDWVLFFI

351 HLTLFHNAFQ MAHFVWTMAT PGLKKCFHEN IWLSIVEVIV GISLQVLCSY

401 ITFPLYALVT QMGSNMKKTI FEEQTMKALM NWRKKAMEKK KVRDADAFLA

451 QMSVDFATPA SSRSASPVHL LQVTGRVGRP PSPITVASPP APEEDMYPVP

501 AAAASRQLLD DPPDRRWMAS SSADIADSDF SFSAQR*

Figure 14

| | | | | | |
|---|---|---|---|---|---|
| 1 | MAGPAGGREL | SDTPTWAVAV | VCAVMILVSV | AMEHALHKLG | HWFHKWRKKA |
| 51 | LGEALEKMKA | ELMLVGFISL | LLIVTQDPVS | RICISKEAGE | KMLPCKPYDG |
| 101 | AGGGKGKDNH | RRLLWLQGES | ETHRRFLAAP | AGVDVCAKQG | KVALMSAGSM |
| 151 | HQLHIFIFVL | AVFHVLYSVV | TMTLSRLKMK | QWKKWESETA | SLEYQFANDP |
| 201 | SRCRFTHQTT | LVRRHLGLSS | TPGVRWVVAF | FRQFFTSVTK | VDYLTLRQGF |
| 251 | INAHLSQGNR | FDFHKYIKRS | LEDDFKVVVR | ISLKLWFVAV | LILFLDFDGI |
| 301 | GTLLWMSVVP | LVILLWVGTK | LEMVIMEMAQ | EIHDRESVVK | GAPAVEPSNK |
| 351 | YFWFNRPDWV | LFLMHLTLFQ | NAFQMAHFVW | TVATPGLKKC | YHEKMAMSIA |
| 401 | KVVLGVAAQI | LCSYITFPLY | ALVTQMGSHM | KRSIFDEQTA | KALTNWRKMA |
| 451 | KEKKKARDAA | MLMAQMGGGA | TPSVGSSPVH | LLHKAGARSD | DPQSVPASPR |
| 501 | AEKEGGGVQH | PARKVPPCDG | WRSASSPALD | AHIPGADFGF | STQR* |

Figure 15

```
  1  MGHGGEGMSL EFTPTWVVAG VCTVIVAISL AVERLLHYFG TVLKKKKQKP
 51  LYEALQKVKE ELMLLGFISL LLTVFQGLIS KFCVKENVLM HMLPCSLDSR
101  REAGASEHKN VTAKEHFQTF LPIVGTTRRL LAEHAAVQVG YCSEKGKVPL
151  LSLEALHHLH IFIFVLAISH VTFCVLTVIF GSTRIHQWKK WEDSIADEKF
201  DPETALRKRR VTHVHNHAFI KEHFLGIGKD SVILGWTQSF LKQFYDSVTK
251  SDYVTLRLGF IMTHCKGNPK LNFHKYMMRA LEDDFKQVVG ISWYLWIFVV
301  IFLLLNVNGW HTYFWIAFIP FALLLAVGTK LEHVIAQLAH EVAEKHVAIE
351  GDLVVKPSDE HFWFSKPQIV LYLIHFILFQ NAFEIAFFFW IWVTYGFDSC
401  IMGQVRYIVP RLVIGVFIQV LCSYSTLPLY AIVSQMGSSF KKAIFEENVQ
451  VGLVGWAQKV KQKRDLKAAA SNGDEGSSQA GPGPDSGSGS APAAGPGAGF
501  AGIQLSRVTR NNAGDTNNEI TPDHNN*
```

POLYNUCLEOTIDE AND ITS USE FOR MODULATING A DEFENCE RESPONSE IN PLANTS

This application is a continuation of application Ser. No. 09/230,728, filed Jan. 29, 1999 now abandoned; which is a 371 of PCT/GB97/02046, filed Jul. 29, 1997, the entire content of which is hereby incorporated by reference in this application.

The present invention relates to stimulating a defence response in plants, with a view to providing the plants with enhanced pathogen resistance. More specifically, it has resulted from cloning of the barley Mlo gene, various mutant mlo alleles, and a number of homologues from various species. The Mlo gene has been isolated using a positional cloning approach which has never previously been successful in Barley. Details and discussion are provided below. Wild-type Mlo exerts a negative regulatory function on a pathogen defence response, such that mutants exhibit a defence response in the absence of pathogen. In accordance with the present invention, down-regulation or out-competition of Mlo function may be used to stimulate a defence response in transgenic plants, conferring increased pathogen resistance.

Mutations have been described in several plants in which defence responses to pathogens appear to be constitutively expressed. Mutation-induced recessive alleles (mlo) of the barley Mlo locus exhibit a leaf lesion phenotype and confer an apparently durable, broad spectrum resistance to the powdery mildew pathogen, *Erysiphe graminis* f sp hordei.

Resistance responses to the powdery mildew pathogen have been genetically well characterized (Wiberg, 1974; Søgaard and Jørgensen, 1988; Jørgensen, 1994). In most analyzed cases resistance is specified by race-specific resistance genes following the rules of Flor's gene-for-gene hypothesis (Flor, 1971). In this type of plant/pathogen interaction, resistance is specified by and dependent on the presence of two complementary genes, one from the host and one from the fungal pathogen. The complementary genes have been termed operationally (pathogen) resistance ("RA") gene and avirulence gene, respectively. Most of the powdery mildew resistance genes (Mlx) act as dominant or semidominant traits (Jøgensen, 1994).

Monogenic resistance mediated by recessive (mlo) alleles of the Mlo locus is different. Apart From being recessive, it differs from race-specifc resistance to single pathogen strains in that (i) it confers broad spectrum resistance to almost all known isolates of the pathogen (ii) nlo resistance alleles have been obtained by mutagen treatment of any tested susceptible wild type (Mlo) variety, and (iii) mao resistance alleles exhibit a defence mimic phenotype in the absence of the pathogen (Wolter et al., 1993). Thus, the genetic data indicate the Mlo wild type allele exerts a negative rmedatory function on defence responses to pathogen attack.

Resistance mediated by alo alleles is currently widely used in barley breeding and an estimated 10 million hectares are annually planted in Europe with seeds of this genotype. A 'mlo' like, inherited resistance to powdery mildew in other cereal plants has not been reported so far although the fungus is a relevant pathogen in wheat (attacked by *rzysiphe graminiu* f sp *triticl*), oat (attacked by *E. g.* f sp *avenae*), and rye (attacked by *.E g.* f sp *secalis*). Because cereals are morphologically, genetically and biochemically highly related to each other (Moore et al., 1995), one would predict the existence of homologous genes in these species. The failure to have found a 'mlo' like, inherited resistance in wheat and oat is probably due to their hexaploid genomes, making it difficult to obtain by mutagenesis defective alleles in all six gene copies, and the chance of all such mutations occurring in Nature is remote. The failure to have found a mlo equivalent in other cereals is probably due to insignificant amount of mutational analysis in these species and complications as a result of their outbreeding nature (e.g. rye).

RFLP markers closely linked to Mlo on barley chromosome 4 were previously identified on the basis of a mlo backcross line collection containing mlo alleles from six genetic backgrounds (Hinze et al., 1991). The map position of Mlo on the basis of RFLP markers was consistent with its chromosomal localization as determined by a previous mapping with morphological markers (Jørgensen, 1977).

Having identified an ~3 cM genetic interval containing Mlo bordered by genetic markers, we decided to attempt to isolate the gene via positional cloning.

However, there is no documented example of a successful positional cloning attempt of a barley gene. We were faced with a number of difficulties.

Firstly, the genome of barley ($5.3\times10^9$ bp/haploid genome equivalent; Bennett and Smith, 1991) has almost double the size of the human genome and because the total genetic map covers ~1.800 cM (Becker et al., 1995) we were confronted with a very unfavourable ratio of genetic and physical distances (1 cM corresponds to ~3 Mb).

Seconcly, a high resolution genetic map had to be constructed around Mlo enabling the positioning of linked markers with a precision of better than 0.1 cM.

Thirdly. we aimed to physically delimit the target gene and both flanking DNA markers on individual large insert genomic clones, a procedure later termed "chromosome landing". (Tanksley er al., 1995). For this pupose, a complete barley YAC library from barley Megabase DNA had to be constructed with an average insert size of 500–600 kb, which was unprecedented.

Fourthly, we had to prepare unusual genetic tools that enabled us to identify the Mlo gene within a physcally delimited region without tne need for a time consuming. generation of barley transgenLc plants and testing of different candidate genes. We used for our studies ten characterized radiation- or chemically-induced mlo mutants (Jørgensen, 1992). For a conclusive chain of evidence of the gene isolation we decided to depend upon a functional restosation of the wild type Mlo allele starting out from characterized mlo defective alleles. For this purpose, we performed mlo heteroallelic crosses and isolated susceptible intragenic Mlo recominants. The sequence analysis of these proves the function of the described gene.

The cloning of the barley Mlo gene and bomlogues, including homologues from other plant species, gives rise to a number of practical applications, reflected in the varsous aspects of the present invention.

According to a first aspect of the present invention there is provided a nucleic acid molecule comprising a nucleotide sequence encoding a peptide with Mlo function. Those skilled in the art will appreciate that "Mlo function" refers to the ability to suppress a defence response, said defence response being race and/or pathogen independent and autonomous of the presence of a pathogen, such as, for example, the Mlo gene of barley, the Acd gene and the Lsd gene of Arabidopsis.

mlo mutations that down-regulate or disrupt functional expression of the wild-type Mlo sequence are recessive, such that they are complemented by expression of a wild-type sequence. Thus "Mlo function" can be determined by assessing the level of constitutive defence response and/or susceptibility of the plant to a pathogen such as, for example, powdery mildew or rust (e.g. yellow rust). Accordingly, a putative nucleotide sequence with Mlo function can be tested upon complementation of a. suitable mlo mutant. The term "mlo function" is used to refer to sequences which confer a mlo mutant phenotype on a plant.

The capitalisation of "Mlo" and non-capitalisation of "mlo" is thus used to differentiate between "wild-type" and "mutant" function.

A mlo mutant phenotype is characterised by the exhibition of an increased resistance against one or more pathogens, which is race and/or pathogen independent and autonomous of the presence of a pathogen.

The test plant may be monocotyledonous or dicotyledonous. Sutable monocots include any of barley, rice, wheat, maize or oat, particularly barley. Suitable dicots include Arabidopsis.

Nucleic acid according to the invention may encode a polypeptide comprising the amino acid sequence shown in FIG. 2, or an allele, variant, derivarive or mutant, or homologue, thereof.

Nucleic acid according to the present invention may have the sequence of a Mlo geae of barley, or be a mutant, variant (or derivative) or allele cf the sequence provided, or a homologue thereof. Preferred mutants, variants and alleles are those which encode a sequence which retains a functional characteristic of the wild-type cene, especially the ability to suppress a defence response as discussed herein. Other preferred mutants, variants and alleles encode a sequence which, in a homozygote, cause constitutive activation of a defence response, or at least promotes activation of a defence response (i.e. is a mlo mutant sequence). e.g. by reducing or wholly or partly abolishing Mlo function. Preferred mutations giving mlo mutant sequences are shown in Table 1. Changes to a sequence, to produce a mutant, derivative or variant, may be by one or more of addition, insertion, deletion or substitution of one or more nucleotides in the nucleic acid, leading to the addition, insertion, deletion and/or substitution of one or more amino acids. of course, changes to the nucleic acid which make no difference to the encoded amino acid sequence are included. Particular variants, mutants. alleles and derivatives are discussed further below, as well as homologues.

A preferred nucleic acid sequence according co an aspect of the present invention is shown in FIG. 2 along with the predicted amino acid sequence. Nucleic acid may be subject to alteration by way of substitution of nucleotides and/or a combination of addition, insertion and/or substitution of one or more nucleotides with or without altering the encoded amino acids sequence (by virtue of the degeneracy of the genetic code).

As discussed below, further aspects of the present invention provide homologues of the Mlo sequence shown in FIG. 2, including from rice (genomic sequence FIG. 5, bottom line, cDNA sequence FIG. 10, amino acid sequence FIG. 13) and barley (genomic sequence FIG. 6, bottom line, cDNA sequence FIG. 11, amino acid sequence FIG. 14); also Table 5B (nucleotii sequences) and FIG. 5A (amino acid sequences) show homologous EST's from rice and Arabidopsis.

The present invention also provides a vector which comprises nucleic acid with any one of the provided sequences, preferably a vector from which a product can be expressed. The vector is preferably suitable for transformation into a plant cell and/or a microbial cell. The invention further encompasses a host cell transformed with such a vector, especially a plant cell ora microbial cell (e.g. *Agrobacterium tumefaciens*). Thus, a host cell, such as a plant cell, comprising nucleic acid according to the present invention is provided. Within the cell, the nucleic acid may be incorporated within the nuclear genome. i.e. a chromosome. There may be more than one heterologous nucleotide sequence per haploid genome.

A vector comprising nucleic aced according to the present inventon need not include a promoter, particularly if the vector is to be used to introduce the nucleic acid nto cells for recombination into the gente.

Nucleic acid molecules and vectors according to the present invention may be provided in a form isolated and/or purified from their natural environment, in substantially pure or homogeneous form, or free or substantially free of nucleic acid or genes of the species of interest or origin other than the relevant sequence. Nucleic acid according to the present rw invention may comprise cDNA, RNA, genomic DNA and may be wholly or partially synthetic. The term "islate" may encc ass all these possibilities.

The prevent invention also encompasses the expression product of ay of the nucleic acid sequences disclosed and methods of making the expression product by expression frow encoding nucleic acid therefore under suitable conditions in suitable host cells, e.g. *E. coli*. Those skilled in the art are well able to construct vectors and design protocols for expression and recovery of products of recombinant gene expression. Suitable vectors can be chosen or constructed, containing one or more appropriate regulatory sequences, including promoter sequences. terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press. Transformation procedures depend on the host used, but are well known. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference, along with all other documents mentioned.

Purified Mlo protein, or a fragment, mutant or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed furtherbelow.

Methods of producing antibodies include immunising a mammal (eg human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immuising a mammal, antibodies with appropriate binding specificity may be obtained from a recombinantly produced library of expressed immunoglobulin variable domains, eg using lambda bacteriophage or filamentous bacteriophage which display functional immunoglobulin binding domains on their surfaces; for instance see WO92/01047.

Antibodies raised to a polypeptide or peptide can be used in the identification and/cr isolation of homologous polypeptides, and then the encoding genes. Thus, the present invention provides a method of identifying or isolating a polypeptide with Mlo or mlo function (in accordance with embodments disclosed herein), comprsisng screening candidate peptides or polypeptides wit a polypeptide comprising the antigen-binding domain of an antibody (for example whole antibody or a fraigment thereof) which is able to bind an Mlo or mlo peptide, polypeptide or fragment, variant or variant thereof or preferably has binding specificity for such a peptide or polypeptide, such as having an amino acid sequence identified herein. Specific binding members such as antibodies and polypeptides comprising antigen binding domains of antibodies that bind and are preferably specific for a Mlo or mlo peptide or polypeptide or mutant, variant or derivative thereof represent further aspects of the present invention, as do their use and methods which employ them.

Candidate peptidee or polypeptides for screening may for instance be the products of an expression library created using nucleic acid derived from an plant of interest, or may be the product of a purification process from a natural source.

A peptide or polypeptide fount to bind the antibody may be isolated and then may be subject to amino acid sequencing. Any suitable technique may be used to sequence the peptide or polypeptide either wholly or partially (for instance a fragment of a polypeptide may be sequenced). Amino acid sequence information may be used in obtaining nucleic acid encodingthe peptide or polypeptide, for instance by designing one or more oligonucleotides (e.g. a degenerate pool of oligonucleotides) for use as probes or primers in hybridisation to candidate nucleic acid, or by searching computer sequence databases, as discussed further below.

A further aspect of the present invention provides a method of identifying and cloning Mlo homologuez from plants, including species other than Barley, which method employs a nucleotide sequence derived from that shown in FIG. 2. Further similar aspects employ a nucleotide sequence derived from any of the other Figures provided herein. Nucleic acid libraries may be screened using techniques well known to those skilled in the art and homologous sequences thereby identified then tested. The provision of sequence information for the Mlo gene of Barley and various homologues enables the obtention of homologous sequences from Barley and other plant species, as exemplified further herein.

Also, one can easily derive PCR primers based on putative within the sequence shown in FIG. 2, a single amino acid change with respect to the sequence shown in FIG. 2, or 2, 3, 4, 5, 6, 7, 8, or 9 changes, about 10, 15, 20, 30, 40 or 50 changes, or greater than about 50, 60, 70, 80 or 90 changes. In addition to one or more changes within the amino acid sequence shown in FIG. 2, a mutant, allele, variant or derivative amino acid sequence may include additional amino acids at the C-terminus and/or N-terminus.

As is well-understood, homology at the amino acid level is id generally in terms of amino acid similarity or idenitity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art, or, and this may be preferred, the standard program BestFit, which is part of the Wisconsin Package, Version 8, September 1994, (Genetics Computer Group, 575 Science Drive, Madison, Wis., USA, Wis. 53711). BestFit makes an optimal alignment of the best segment of similarity between two sequences. Optimal alignments are found by inserting gaps to maximize the number of matches using the local homology algorithm of Smith and Waterman Homology may be over the full-length of the relevant exon sequences, which might be identified by comparison with the Mlo sequence provided in FIG. 2 wherein exons are highlighted, and perform RT-PCR with total FRN from the plant of interest, e.g. barley and rice for the homologues shown in FIGS. 5 and 6, with cDNA and amino acid sequences shown in other figures herein.

The homologues whose nucleotide sequences are given and whose amino acid sequences are given or are deducible represent and provide further aspects of the present invention in accordance with those disclosed for the parley gene shown in FIG. 2.

The present invention also extends to nucleic acid encoding a Mlo homologte obtained using a nucleotide sequence derived from that shown in FIG. 2. or the amino acid sequence shown in FIG. 2. Preferably, the nucleotide seqrence and/or amino acid sequence shares homology with the sequence encoded by the nucleotide sequence of FIG. 2, preferably at least about 50%, or at least about 55%, or at least abou 60%, or at least about 65%. or at least about 70%, or at least about 75%, or at least about 80% homology, or at least about 85% homology, or at least about 90% homology. most preferably at least about 95% homology. "Homology" in relation to an amino acid sequence may be used to refer to identity or similarity, preferably identity. Righ levels of amlno acid identity may be limited to functionally significant domains or regions.

A mutant, allele, variant or derivative amino acid sequence in accordance with the present invention may include seouence shown herein, cr may more preferably be over a contiguous secuence of about or greater than about 20, 25, 30, 33, 40, 50, 67, 133, 167, 200, 233, 267, 300, 333, 400, 450, 500, 550, 600 or more amino acids or codons, compared with the relevant amino aced secuence or nucleotide sequence as the case may be.

The EST sequences provided herein, have on average 70% similarity and 50% identity with the Mlo amino acid sequence of FIG. 2. We show that the rice homologue (FIG. 5) and barley homologue (FIG. 6) have an amino acid identity of 81% (amino aced secuences shown in FIG. 13 and FIG. 14).

In certain embodiments, an allele, variant, derivative, mutant or homologue of the spec, ic seeqence may show little overall homology, say about 20%, or about 25%, or about 30%, or about 35%, or about 40% or about 45%, with the specific sequence. However, in functioally significant domains or regions the amino acid homology may be much higher. Putative functionally signilicant domains or regions can be identified using processes of bioimformatica, including comparison of the sequences of homologues. Functionally significant domains or regions of different polypeptides may be combined for expression from encoding nucleic acid as a fusion protein For example, particularly advantageous or desirable properties of different homologues may be combined in a hybrid protein, such that the resultant expression product. with Mlo or mlo function, may comprise fragments of various parent proteins.

The nucleotide sequence information provided herein, or any part thereof, may be used in a data-base search to find homologous sequences, expression products of which can be tested for Mlo or mlo function. These may have ability to complement a mlo mutant phenotype in a plant or may, upon expression in a plant, confer a mlo phenotype.

In public sequence databases we recently identified several homologues for the sequence of FIG. 2. We have already found homologues in rice and barley, and the dicot. Arabidopals.

By sequencing homologues, studying their expression patterns and examining the effect of altering their expression, genes carrying out a similar function to Mlo in Barley are obtainable. Of course, mutants, variants and alleles of these sequences are included within the scope of the present invention in the same terms as discussed above for the Barley gene.

Homology between the hbmologues as disclosed herein, may be exploited in the identification of further homologues, for example using oligonucleotides (e.g. a degenerate pool) designed on the basis of sequence conservation.

According to a further aspect, the present invention provides a method of identifying or a method of cloning a Mlo homologue, e.g. from a species other than Barley, the method employing a nucleotide sequence derived from that shown in FIG. 2 or that shown in any of the other Figures herein. For instance, such a method may employ an oligonucleotide or oligonucleotides which comprises or comprise a sequence or sequences that are conserved between tne sequences of FIGS. 2 and/or 3 and/or 6 and/or 10 and/or 11 and/or 12. or encoding an amino acid sequence conserved between FIGS. 2 and/or 7 and/or 13 and/or 14 and/or 15 to search for hzmologues. Thus, a method of obtaining nucleic acid is provided. comprising hybridisation of an oligonucleotide or a nucleic acid molecule comprising such an oligonucleotide to target/candidate nucleic acid. Tarcet or candidate nucleic acid may. for example. comprise a genomic or cDoA library obtainable from an organism known to contain or suspected of containing such nucleic acid, either monocotyledonous or dicotyledonous. Successful hybridisation may be identified and target/candidate nucleic acid isolated for further investigation and/or use.

Hybridisation may involve probing nucleic acid and identifying positive hybridisation under suitably stringent conditions (in accordance with known tecbnicues) and/or use of oligonucleotides as primers in a method of nucleic acid amplificacion, such as PCR. For probing, preferred conditions are those which are stringent enough for there to be a simple pattern with a small number of hybridisations identified as positive which can be investigated further. It is well kown in the art to increase stringency of hybridisation gradually until only a few positive clones remain.

As an alternative to probing, though still employing nucleic acid hybridisation. oligonucleotides designed to amplify DNA sequences may be used in PM reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers for some purposes are sequences conserved (completely, substantially or partly) between at least two Mlo peptidesor polypeptides encoded by genes able to suppress a defence response in a plant, e.g. with any of the amino acid sequences of any of the various figures herein and/or encoded by the nucleotide sequences of any of the various figures herein.

On the basis of amino acid sequence information oligonucleotide probes or primers may be desigred, taking into account the degeneracy of the genetic code, and, where appropriate, codon usage of the organism from the candidate nucleic acid is derived.

Preferably an oligonucleotide in accordance with certain embodiments of the invention, e.g. for use in nucleic acid amplification, is up to about 50 nucleotides, or about 40 nucleotides or about 30 or fewer nucleotides in length (e.g. 18, 21 or 24).

Assessment of whether or not such a PCR product corresponds to Mlo homologue genes may be conducted in various ways. A PCR band from such a reaction might contain a complex mix of products. Individual products may be cloned and each one individually screened. It may be analysed by transformation to assess function on introduction into a plant of interest.

As noted, nucleic acid according to the present invention is obtainable using oligonucleotides, designed on the basjs of sequence information provided herein. as probes or primers. Nucleic acid isolated and/or puriied from one or more cells of barley or another plant (see above), or a nucleic acid library derived from nucleic acid isolated and/or purified from the plant (e.g a cDNA library derived from mRNA isolated from the plant), may be probed under conditions for selective hybridisation and/or subjeced to a specific nucleic acid amplification reaction such as the poivmerase chain reactction (PCR). The nucleic acid probed or used as template in the amplification reaction may be genoic DNA, cDN or RNA. If necessary. one or more gene fragments may be ligated to generat a full-length coding sec eznce.

We have tested several PCR primers derived from the Mlo sequence disclosed herein to test their specificity for amolifying nucleic acid according to the present invention, using both barley genomic DNA and RT-PCR templates. The latter was synthesized from barley polyaA$^+$ RNA. In each case we were able to amplify the expected Mlo derived gene fragments as shown by cloning and subsequent DNA sequencing of the PCR products. Full length cDNA clones can be obtained as described by 5' and 3' RACE technology if RT-PCR products are used as templates.

Examples of primers tested include:

| | | |
|---|---|---|
| 25L | 5'-GTG CAT CTG CGT GTG CGT A-3' | (SEQ ID NO:57) |
| 25LN | 5'-GTG TGC GTA CCT GGT AGA G-3' | (SEQ ID NO:58) |
| 25R | 5'-AAC GAC GTC TGG TGC GTG-3' | (SEQ ID NO:59) |
| 33 | 5'-TGC AGC TAT ATG ACC TTC CCC CTC-3' | (SEQ ID NO:60) |
| 37 | 5'-GGA CAT GCT GAT GGC TCA GA-3' | (SEQ ID NO:61) |
| 38 | 5'-CAG AAC TTG TCT CAT CCC TG-3 | (SEQ ID NO:62) |

-continued

```
38A    5'-GGC TAT ACA TTG GGA CTA ACA-3'       (SEQ ID NO:63)

38B    5'-CGA ATC ATC ACA TCC TAT GTT-3'       (SEQ ID NO:64)

39     5'-GCA AGT TCG ACT TCC AC-3'            (SEQ ID NO:65)

39A    5'-TCG ACT TCC ACA AGT ACA TCA-3'       (SEQ ID NO:66)

53     5'-AGC GTA CCT GCG TAC GTA G-3'         (SEQ ID NO:67)
```

Various primer combinations have been tested: 38/39A; 38/39; 38/33; 38/37; 38A/39A; 38B/39A; 38/25L; 38/25LN; 25R/25L; 25R/25LN; 25R/53.

Various aspects of the present invention include the obtainable nucleic acid, methods of screening material, e.g. cell lysate, nucleic acid preparations, for the presence of nucleic acid of interest, methods of obtaining the nucleic acid, and the primers and primer combinations given above.

The sequence information provided herein also allows the design of diagnostic tests for determination of the presence of a specific mlo resistance allele, or a susceptibility allele (e.g. wild-type), in any given plant, cultivar, variety, population, landrace, part of a family or other selection in a breeding programme or other such genotype. A diagnostic test may be based on determination of the presence or absence of a particular allele by means of nucleic acid or polypeptide determination.

At the nucleic acid level, this may involve hybrzdisation of a suitable oligo- or poly-nucleotide, such as a fragment of the Mlo gene or a homologue thereof. including any homologue disclosed herein, or ary particular allele, such as an allele which gives an mlo phenotype. such as any such allele disclosed herein. The hybridisation may involve PCR designed to amplify a product from a given allelic version of mlo, with subsequent detection of an amplified product by any of a number of rd possible methods including but not limited to gel electrophoresis, capillary electrophoresis, direct hybrid saticn of nucleotide sequence probes and so on. A diagnostic test may be based on PCR designed to amplify various alleles or any allele from the Mlo locus, with a test to distingish the different posuible alleles by any of a number of possible methods, including MM fragment size, restriction site variation; (e.g. CAPS—cleaved amplified polymorphic sites) and so on. A diagnostic test may also be based on a great number of possible variants of nucleic acid analysis that will be apparent to those skilled in the art, such as use of a synthetic mloderived sequence as a hybridisation probe Broadly, the methods divide into those screening for the presence of nucleic acid sequences and those that rely on detecting the presence or absence of a polypeptide. The methods may make use of biological samples from one or more plants or cells that are suspected to contain the nucleic acid sequences or polypeptide.

Exemplary approaches for detecting nucleic acid or polypeptides include analysing a sample from the plant or plant cell by:

(a) comparing the sequence of nucleic acid in the sample with all or part of the nucleotide sequence shown in FIG. 7 to determine whether the sample from the patient contains a mutation;

(b) determining the presence in the sample of a polypeptide including the amino acid sequence shown in FIG. 2 or a fragment thereof and, if present, determining whether the polypeptide is full length, and/or is mutated, and/or is expressed at the normal level;

(c) performing DNA fingerprinting to compare the restriction pattern produced when a restriction enzyme cuts. nucleic acid in the sample with the restriction pattern obtained from the nucleotide sequence shown in FIG. 7 or from a known mutant, allele or variant thereof;

(d) contacting the sample with a specific binding member capable of binding to nucleic acid including the nucleotide sequence as set out in FIG. 7 or a fragment thereof, or a mutant, allele or variant thereof, the specific binding member including nucleic acid h ybridisable with the sequence of FIG. 7 or a polypeptide including a binding domain with specificity for nucleic acid including the sequence of FIG. 7 or the polypeptide encoded by it, or a mutated form thereof, and determining binding of the specific binding member;

(e) performing PCR involving one or more primers based on the nucleotide sequence shown in FIG. 7 to screen the sample for nucleic acid including the nucleotide sequence of FIG. 7 or a mutant, allele or variant thereof.

When screening for a resistance allele nucleic acid, the nucleic acid in the sample will initially be amplified, e.g. using PCR, to increase the amount of the analyte as compared to other sequences present in the sample. This allows the target sequences to be detected with a high degree of sensitivity if they aze present in the sample. This initial step may be avoided by using highly sensitive array techniques that are becoming increasingly important in the art.

A variant form of the gene may contain one or more insertions, deletions substitutions and/or additions of one or more nucleotides compared with the wild-type sequence (such as shown in Table 1) which may or may not distrupt the gene function. Differences at the nucleic acid level are not necessarily reflected by a difference in the amino acid sequence of the encoded polypeptide. However, a mutation or other difference in a gene may result in a frame-shift or stop codon, which could seriously affect the nature of the polypeptide produced (if any), or a point mutation or gross mutational change to the encoded polypeptide. including insertion, deletion, substitution and/or addition of one or more amino acids or regions in the polypeptide. A mutation in a promoter sequence or other regulatory region may prevent or reduce expression from the gene or affect the processing or stability of the mRNA transcript.

Tests may be carried out on preparations containing genomic DNA, cDNA and/or mRNA. Testing cDNA or mRNA has the advantage of the complexity of the nucleic acid being reduced by the absence of intron sequences, but the possible disadvantage of extra time and effort being required in making the preparations. RNA is more difficult to manipulate than DNA because of the wide-spread occurrence of RN' ases.

Nucleic acid in a test sample may be sequenced and the sequence compared with the sequence shown in FIG. 2, or other figure herein, to determine whether or not a difference is present. If so, the difference can be compared with known susceptibility alleles (e.g. as summarised in Table 1) to determine whether the test nucleic-acid contains one or more of the variations indicated, or this difference can be investigated for association with disease resistance.

The amplified nucleic acid may then be sequenced as above, and/or tested in any other way to determine the presence or absence of a particular feature. Nucleic acid fortesting may be prepared from nucleic acid removed from cells or in a library using a variety of other techniques such as restriction enzyme digest and electrophoresis.

Nucleic acid may be screened using a variant- or allele-specific probe. Such a probe corresponds in sequence to a region of the gene, or its complement, containing a sequence alteration known to be associated with disease resistance. Under suitably stringent conditions, specific hybridisation of such a probe to test nucleic acid is indicative of the presence of the sequence alteration in the test nucleic acid. For efficient screening purposes, more than one probe may be used on the same test sample.

Allele- or variant-specific oligonucleotides may similarly be used in PCR to specifically amplify particular sequences if present in a test sample. Assessment of whether a PCR band contains a gene variant may be carried out in a number of ways familiar to those skilled in the art. The PCR product may for instance be treated in a way that enables one to dsplay the mutation or polymorphism on dematuring polyacrylamide DNA sequencing gel, with specific bands that are linked to the gene variants being selected.

An alternative or supolement to looking for the presence of variant sequences in a test sample is to look for tne presence of the normal sequeace, e.g. using a suitably specific oligonucleotide probe or primer.

Approaches which rely on hybridisation between a probe and test nucleic acid and subsequent detection of a mismatch may be employed. Under appropriate conditions (temperature pH etc.), an oligonucleotide probe will hybridise with a aecuence which is not entirely complementary. The degree of base-pairing between the two molecules will be sufficient for them to anneal despite a mis-match. Various approaches are well known in the art for detecting the presence of a mis-match between two arnealing nucleic acid molecules.

For instance. RN' ase A cleaves at the site of a mis-match. Cleavage can be detected by electrophoresing test nucleic acid to which the relevant probe or probe has annealed and looking for smaller molecules (i.e. molecules with higher electrophoretic mobility) than the full length probe/test hybrid. Other approaches rely on the use of enzymes such as resolvases or endonucleases.

Thus, an oligonucleotide probe that has the sequence of a region of the normal gene (either sense or anti-sense strand). in which mutations associated with disease resistance are known to occur (e.g. see Table 1) may be annealed to test nucleic acid and the presence or absence of a mis-match determined. Detection of the presence of a mis-match may indicate the presence in the test nucleic acid of a mutation associated with disease resistance. On the other hand, an oligonucleotide probe that has the sequence of a region of the gene including a mutation associated with disease resistance may be annealed to test nucleic acid and the presence or absence of a mis-match determined. The presence of a mis-match may indicate that the nucleic acid in the test sample has the normal sequence, or a different mutant or allele sequence. In either case, a battery of probes to different regions of the gene may be employed.

The presence of differences in sequence of nucleic acid molecules may be detected by means of restriction enzyme digestion, such as in a method of DNA fingerprinting where the restriction pattern produced when one or more restriction enzymes are used to cut a sample of nucleic acid is compared with the pattern obtained when a sample containing the normal gene or a variant or allele is digested with the same enyme or enzymes.

The presence of absence of a lesion in a promoter or other regulatory sequence may also be assessed by deter ing the level of mRNA production by transcription or the level of polypeptide production by translation from the mRNA.

Nucleic actd isolated and/or purif ed from one or rore cells of a plant or a nucleic acid library derived from nucleic acid isolated and/or purified from cells (e.g. a cDNA library derived from mRNA isolated from the cells), may be probed under conditions for selected hybridisation and/or subjected to a spcecfic nucleic acid amplification reaction such as the polymerase chain reacticn (PCR).

A method may include hybridisation of one or more (e.g. two) probes or primers to target nucleic acid. Where the nucleic acid is double-stranded DNA, hybridization will generally be preceded by denaturation to produce single-stranded DNA. the hybridisation may be as part of a PCR procedure, or as part of a probing procedure not involving PCR. An example proceduse would be a combination of PCR and low stringency hybridisation. A screening procedLte, chosen foat the many available to those skilled is the art, is used to identify successful hybridisuation events and isolate hybridised nucleic acid.

Binding of a probe to target nuclgic acid (e.g. DNA) may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNAase cleavage and allele specific oligonucleotide probing.

Probing may employ the standard Southern blotting technique. For instance DNA may be extracted from cells and digested with different restriction enzymes. Restriction fragments may then be separated by electrophoresis on an agarose gel, before denaturation and transfer to a ru nitrocellulose filter. Labelled probe may be hybridised to the DNA fragments on the filter and binding determined. DNA for probing may be prepared from RNA preparations from cells.

Preliminary experiments may be performed by hybridising under low stringency conditions various probes to Southern blots of DNA digested with restriction enzymes. Suitable conditions would be achieved when a large number of hybridising fragments were obtained while the background hybridisation was low. Using these conditions nucleic acid libraries, e.g. cDNA libraries representative of expressed sequences, may be searched.

As noted, those skilled in the art are well able to employ suitable conditions of the desired stringency for selective. hybridisation, taking into account factors such as oligonucleotide length and base composition, temperature and so on.

In some preferred embodiments of diagnostic assays according to the present invention, oligonwtcleotides according to the present invention that are fragments of any of the sequences shown in FIG. 2, or ary allele associated with disease resistance, e.g. as identified in Table 1. are at least about 10 nucleotides in length, more preferably at least about 15 nuleotides in length, more preferably at least about 20 nucleotides in length, more preferably about 30 nucleotides rn length. Such fragments themselves individually represent aspects of the present invention. Fragments and other oligonucleotides may be used as primers or probes as discussed but may also be generated (e.g. by PCR) in methods concerned with determining the presence in a test sample of a sequence indicative of disease resistance.

There are various methods for deteníncr the presence cr absence in a tess sample of a particular polypeptide, such as the polypeptide with the amino acid sequence shown in FIG. 2. or other figure herein, or an amino acid sequence mutant, variant or allele thereof (e.g. including an alteration show in Table 1).

A sample may be tested for the presence of a binding partner for a specific binding member such as an antibody (or mixture of antibodies), specific for one or tore particular variants of the polypeptide shown in FIG. 2 e.g. see Table 1.

In such cases, the sample may be tested by being contacted with a specific binding membe such as an antibody under appropriate conditions for specific binding, before binding is determined, for instance using a reporter system as discussed. Where a panel of antibodies is used, different reporting labels may be employed for each antibody so that binding of each can be determined.

A specific binding member such as an antibody may be used to isolate and/or purify its binding partner polypeptide from a test sample, to allow for sequence and/or biochemical analysis of the polypeptide to determine whether it has the sequerce and/or properties of the wild-type polypeptide or a particular mutant, variant or allele thereof. Amino acid sequence is routine in the art using automated sequencing machines.

The use of diagnostic tests for mlo alleles allows the researcher or plant breeder to establish, with full confidence. and independent from time consuming resistance tests, whether or not a desired allele is present in the plant of interest (or a cell thereof), whether the plant is a representative of a collection of other genetically identical plants (e.g. an inbred variety or cultivar) or one individual in a sample of related. (e.g. breeder's selection) or unrelated plants. The mlo alleles conferring the desirable disease resistance phenotype are recessive, and are not therefore detectable at the whole plant phenotype level when in a heterozygous condition in the presence of a wild-type Mlo allele. Phenotypic screening for the presence of such recessive alleles is therefore only possibze on material homozvgous for the mlo locus and so delays substantially the generation in a plant breeding programme at which selection can be reliably and cost-effectively applied. In a bakcross breeding proramme where, for example, a breeder is aiming to intergress a desirable mlo allele into an elite adapted high performing target genotype, the mlo locus will be permanently in the heterozygcus condition until selling is carried out. Nucleic acid or pollpeptide testing for the presence of the recessive allele avoids the need to test self ed progeny of backcross aene-atior. individuals, thus saving considerable time and money. In other types of breedins scheme based on selection and selfing of desirable individuals, nucleic acid or polypeplide diagostics for the desirable mlo alles in high throughput, low cost assays as provided by this invention, reliable selection for the desirable mlo alleles can be made at early generatcns and on more material than would otherwise be possible. This gain in reliabiilty of selection plus the time saving by being able to teat material earlier and wthcut costly resistance phenotype screening is of considerable value in plant breeding.

By way of example for nucleic acid testing, the barley mlo-5 resistance allele is characterized by a G- to A-nucleotide substitution in the predicted start codon of the Mlo gene (Table 1) The. mutation may easily be detected by standard PCR amplification of a Mlo gene segment from genomic template DNA with the primers:

forward primert 51'-GTTGCCACACTTTGCCACG-3' (SEQ ID NO:68)

reverse primert 5'-AAGCCAAGACGACAATCAGA-31' (SEQ ID NO:69) (for example), followed by digestion with the restriction enzyme PohA1. This generates a cleaved amplified polymorphic sequences (CAPS) marker which may be displayed using conventional agarose gel electrophoresis. Presence of a 769 bp fragment is indicative of the presence of the mlo-5 allele.

The plos-9 resistance allele is characterized by a C- to T-nucleotide substitution (Table 1). Thin allele is of particular relevance since it is used frequently in breeding material. The mutational event may be easily detected using the primers:

forward primer 5'-GRROCCACACTTTGCCACG-3' (SEQ ID NO:70)

reverse primer 5'-AAGCCAAGACGACAATCAGA-3' (SEQ ID NOs71)

(for example) and subsegment digestion of genomic amplification products with the restriction enzyme Rha1. This generates a CAPS marker which may be displayed by conventional agaroqe gel electrophoresin. The presence ofa 374 bp fragment is indicative of the presence of mlo-9.

A third, particularly interesting allele is mlo-12, characterised by a substitution a residue 240, specifically. a Phe240 to leucine replacement. This may result from a C720. to A substitution in the encoding nucleotide sequence (Table 1). This is the only currently documented moc allele for which conclusive evidence is available that the altered protein retains residual wild-type activity (Hentrich, 1979*, Arch. Züchtungsvorsch., Berlin* 9, S. 283–291). mlo-12 exhibits no detectable spontaneous cell death reaction but confers a sufficient level of resistance to pathogens such as the powdery midew fungus. mlo12 may therefore be the allele of choice in breeding programs if minimal pleiotropic effects (spontaneous cell death) are desirable after introgression of the mlo resistance in elite breeding lines. Furthermore, the molecular site of the amino acid substition within the Mlo protein allows the design of alleles with a residual wild-type activity, and also the obtention of ineraccrng and/or inhibitor molecules, reducer undesirable pleiotropic effects from a complete loss of function of the Mlo protein.

Nucleic aced-based determination of the presence or absence of mlo alleles may be comiined with determination of the gerotype of the flanking linked genomic DNA and other unlinked genomic DNA using established sets of markers such as RFLPs. microsatellites or SSRs. AFLPs etc. This enables the researcher or plant breeder to select for not only the presence of the desirable nlo alelei but also for individual plant or families of plans which have the most desirable combinations of linked and unlinked genetic background. Such recombinations of desirable material may occur only rarely within a given segregating breeding population or backcross progeny. Direct assay of the slo locus as afforded by the present invention allows the researcher to make a stepwise approach to fixing (making homosygous) the desired combination of flanking markers and mlo alleles, by first identifying individuals fixed for one flanking marker and then identifying progeny fixed on the other side of the mlo locus all the time knowing with confidence that the desirable mlo allele is still present.

The present disclosure provides sufficient information for a person skilled in the art to obtain genomic DNA sequence for. any given new or existing mlo allele and devise a suitable nucleic acid- and/or polypeptide-based diagnostic assay. Existing mlo alleles to which this may be applied include, for example, mlo-1, mlo-3, mlo-4, mlo-5, mlo-6, mlo-7, mlo-8, mlo-9, mlo-10, mlo-12, mlo-13, mlo-16, mlo-17, mlo-26 and mlo-28, for all of which sequence information is provided herein (see e.g. FIG. 2 and Table 1). In designing a nucleic acid assay account is taken of the distinctive variation in sequence that characterises the particular variant allele. Thus, the present invention extends to an oligonucleotide fragment of a mlo allele, having a sequence which allows it to hybridise specifically to that allele as compared with other mlo alleles. Such an oligonucleotide spans a nucleotide at which a mlo mutation occurs, and may include the mutated nucleotide at or towards its 3' or 5' end. Such an oligonucleotide may hybridise with the sense or anti-sense strand. The variation may be within the coding sequence of the mlo gene, or may lie within an intron sequence or in an upstream or downstream non-coding sequence, wherein disruption affects or is otherwise related to the lesion in Mlo that results in the mildew resistant phenotype.

The mlo-9 allele iswidely but not exclusively used in plant breeding (J Helms Jørgensen—Euphytica (1992) 63: 141–152), mlo-11 is also used. Use oF mlo mutants in practical !breeding has largely been restricted to spring barley, because the spontaneous cell death resporse associated with many of the mutant alleles appears to represent a penalty to plant growth and performance when incorporated nto high yielding winter barley genotypes. However different alo alleles have different degrees of associated spootaneous ceil death response, and thus some, either existing or newly created from mutagenesis programmes or lated as spontaneous mutants, are more suitable than others for incorporation into winter barley backgrounds. The mlo-12 allele ry be particularly suitable since no detectable pleiotropic effects occur desplte conferring a sufficient level of pathogen resistance. The use of mlo based mildew resistance m-e widely in winter barleys will have significant value for barley growers as well as significant economic and environmental implications such as reduced use of fungicide inputs with their associated treatment costs. The provision of nucleic acid diagnostics as provided herein enables rapid and accurate deployment of new and existing mlo alleles into winter barley germplasm.

Plants which include a plant cell according to the invention are also provided, along with any part or propagule thereof, seed, selfed or hybrid progeny and descendants. A plant according to the present invention may be one which does not breed true in one or more properties. Plant varieties may be excluded, particularly registrable plant varieties according to Plant Breeders' Rights. It is noted that a plant need not be considered a "plant variety" simply because it contains stably within its genome a transgene, introduced into a cell of the plant or an ancestor thereof.

In addition to a plant, the present invention provides any clone of such a plant, seed, selfed or hybrid progeny and descendants, and any part of any of these, such as cuttings, seed. The invention provides any plant propagule, that is any part which may be used in reproduction or propagation, sexual or asexual, including cuttings, seed and so on. Also encompassed by the invention is a plant which is a sexually or asexually propagated off-spring, clone or descendant of such a plant, or any part or propagule of said plant, off-spring, clone or descendant.

A further aspect of the present invention provides a method of making a plant cell involving introduction of the sequence (e.g. as part of a suitable vector) into a plant cell and causing or allowing recombination between the vector and the plant cell genome to introduce the sequence of nucleotides into the genome.

Following transformation of a plant cell a plant may be regenerated.

The invention further provides a method of modulating Mlo expression in a plant, which may modulate a defence response in the plant, comprising expression of a heterologous Mlo gene sequence (or mutant, allele, variant or homologue thereof, as discussed) wizhin cells of the plant. As discussed further herein, modulation or alteration of the level of constitutive defence response in a plant may be by way of suppression, repression or reduction (in the manner of wild-type Mlo) or promotion, stimulation, activation, increase, enhancement or augmentation (in the manmer of mutant mlo). Activation or enhancement of the defence response may confer or increase pathogen resistance of the plant, especially resistance to powdery mildew and/or rust (such as yellow rust).

The term "heterologous" may be used to indicate that the gene/sequence of nucleotides in question have been introduced into said cells of the plant or an ancestor thereof, using genetic engineering, we by human intervention. A transgenic plant cell, i.e. trarsganic or the nucleic acid in question, may be provided. The transgene may be on an extra-genomic vector or incorporated, preferably stably, into the genome. A heterologous gene may replace an endogenous equivalent gene, ie one which normally perform the same or a similar functions or the inserted secuence may be additional to the endogenous gene or other sequence. An advantage of introduction of a heterologous gene is the ability to place expression of a sequence under the control of a promoter of choice, in order to be able to influence expression according to preference, such as under particular developmental. spatial or temporal control, or under control of an inducible promoter. Furthermore. mutants, variants and derivatives of the wild-type gene, e.g. with higher or lower activity than wild-type, may be used in place of the endogenous gene. Nucleic acid heterologous, or exogenous or foreign, to a plant cell may be non-naturally occuring in cells of that type, variety or species. Thus, nucleic acid may include a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of. that type or species or variety of plant, such as operably linked to one or more regulatory sequences, such as a promoter sequence, for control of expression. A sequence within a plant or other host cell may be identifiably heterologous, exogenous or foreign.

Down-regulation of wild-type Mlo gene function lead to stimulation of a constitutive defence response. This may be achieved in a number of different ways, as illustrated below. The nucleic acid according to the invention may be placed under the control of an inducible gene promoter thus placing expression under the control of the user.

In a further aspect the present invention provides a gene construct comprising an inducible promoter operatively linked to a nucleotide sequence provided by the present invention. As discussed, this enables control of expression of the gene. The invention alsoprovides plants transformed with said gene construct and methods comprising introduction of such a construct into a plant cell and/or induction of expression of a construct within a plant cell, e.g. by application of a suitable stimulus, such as an effective exogenous inducer or endogenous signal.

The term "inducible" as applied to a promoter is well understood by those skilled in the art. In essence, expression under the control of an inducible promoter is "switched on" or increased in response co an applied stimulus (which may be generated within a cell or provided exogenously). The nature of he stimulus varies between pronoters. Some inducible promoters cause little or undetectable levels of expression (or no expression) in the absence of tne appropriate stimulus. other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "witchable") promoter may be used which causes a basic level of expression in the absence of the stimulus which level is too low to bring about a desired phenotype (and may in fact be zero). Upon application of the scimulus, expression is increased (or switched on) to a level which brings about the desired phenotype.

Suitable promoters include the Cauliflower Mosaic Virus 35S (CaKV 35S) gene promoter that is expressed at a high level in virtually all plant tissues (Benfey et al, (1990a) EMBO J 9: 1677–1684); the cauliflower meri 5 promoter that is expressed in the vegetative apical meristem as well as several well localised positions in the plant body, eg inner phloem, flower S primordia, branching points in root and shoot (Medford, J. I. (1992) *Plant Cell* 4, 1029–1039; Medford et al, (1991) *Plant Cell* 3, 359–370) and the *Arabidopsis thaliana* LEAFY promoter that is expressed very early in flower development (Weigel et al, (1992) *Cell* 69, 843–859).

An aspect of the present invention is the use of nucleic acid according to the invention in the production of a transgenic plant.

When introducing a chosen gene construct into a cell, certain considerations must be taken into account, well known to those skilled in the art. The nucleic acid to be inserted should be assembled within a construct which contains effective regulatory elements which will drive transcription. There must. be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by Agrobacterium exploiting its natural gene transfer ability (EP-A-270355, EP-A-0116718, NAR 12(22) 8711–87215 1984), particle or microprojectile bombardment (U.S. Pat. No. 5,100,792, EP-A-444882, EP-A-434616) microinjection (WO 92/09696, WO 94/00583, EP 331083, EP 175966, areen et al. (1987) *Plant Tissue and Cell Culture*, Academic Press), electroporation (EP 290395, WO 8706614) other forms of direct DNA uotaLe (DE 4005152, WO 9012096, U.S. Pat. No. 4,684,611), liposome mediated DNA uptake (e.g. Freeman et al. *Plant Cell Physiol*. 29: 1355 (1984)), or the vortexing method (e.g. Kindle. *PMAS U.S.A*. 87: 1228 (1950d) Physical methods for the traraformation of plait cells are reviewed in Oard, 1991, *Biotech. Adv*. 9: 1–11.

Agrobacterium transforration is widely used by those skilled in the art to transform *dicotyledonous* species. Recently, there has been substantal progress towards the routine production of stable, ferile transgenic plants in almost all economically relevant motocot plants (Toriyama, et al. (1988) *Bio/Technology* 6, 1072–1074; Zhang, et al. (1988) *Plant Cell Rep*. 7, 379–384; Zang. et al. (1988) *Theor Appl Genet* 76, 835–840; Shommoto, et al. (1989) *Nature* 338, 274–276; Datta, et al. (1990) *Bio/Techuclogy* 8, 736–740; Chriseou, et al. (1991) *Bio/Techiology* 9, 957–962; Peng, et al. (1991) International Rice Research institute, Manila, Philippines 563–574; Cao, et al. (1992) *Plant Cell Rep*. 11, 585–591; Li, et al. (1993) *Plant Cell Rep*. 12, 250–255; Rathore, et al. (1993) *Plant Molecular Biology* 21, 871–884; Fromm. et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, Agrobacterium mediated transformation is now emerging also as an highly efficient alternative transformation method in monocots (Hiei et al. (1994) *The Plant Journal* 6, 271–282)

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct. DNA uptake are preferred where Agrobacterium is inefficient or ineffective. Alternatively, a combination of different techniques may be employed to enhance the efficiency of the transformation process, eg bombardment with Agrobacterium coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from calls, tissues and organs of the plant. Available techniques are reviewd in Vasil et al., *Cell Culture and Somatic Cel Genetica of Plants, Vol* I, II and III, *Laborasozy Procedures and Their Applications*, Academic Press, 1994, and Weissbach and Weissbach, *Methods for Plant Molecular Biology*, Academic Press, 1989.

The particular choice of a transformation technoogy will be determined by its efficiency to transform certain plant species as well as the experience and preference of the person paractising the inventiorn with a particular methodology of choice. It will be apparen to the skilled person that the particular choice of a tzansforration system to introduce nucleic acid into plant cells is not essential to or a limitaton of the invention, nor is the choice of technique for palnt regeneration.

In the present invetion expression may be achieved by introduction of the nucleotide sequence in a sense orientation. Thus, the present invention provides a method of modulation of a defence response in a plant, the method comprasing causing or allowing expression of nucleic acid according to the inition within cells of the plant. Generally. it will be desirable to stimulate the defence response, and this may be achieved by disrupting Mlo gene function.

Down-regulation of expreasion of a target gene may be achieved using anti-sense technology or "magnse regulatiorn" ("co-suppression").

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in Bourque, (1995), *Plant Science* 105, 125–149, and Flavell, (1994) *PNAS USA* 91, 3490–3496.

An alternative is to use a copy of all or part of the target gene inserted in sense, that is the same, orientation as the target gene, to achieve reduction in expression of the target gene by co-suppression. See, for example, van der Krol et al., (1990) *The Plant Cell* 2, 291–299; Napoli et al., (1990) *The Plant Cell* 2, 2:79–289; Zhang et al., (1992) *The Plant Cell* 4, 1575–1588, and U.S. Pat. No. 5,231,020.

The complete sequence corresponding to the coding sequence (in reverse orientation for anti-sense) need not be used. For example fragments of sufficient length may be used. It is a routine matter for the person skilled in the art to screen fragments of various sizes and from various parts of the coding sequence to optimise the level of anti-sense inhibition It may be advantageous to include the initiating methionine ATG codon, and perhaps one or more nucleotides upstream of the initiating codon. A further possibility is to target a conserved sequence of a gene, e.g. a sequence that is characteristic of one or more genes, such as a regulatory sequence. Antisenme constructs may involve 3' end or 5' end secquences of Mlo or homologues. In cases where several Mlo homologues exist in a plant species, the involvement of 5'- and 3'-end untranslated sequences in the construct will enhance specificity of silencing.

The sequence employed may be about 500 iucleotides or less, possibly about 400 nucleotides, about 300 nucleotides. about 200 nucleotides, or about 100 nucleotides. It may be possibie to use oligonucleotides of much ahorter lengths, 14–23 nucleotides, although longer fragments, and generally even lorger than about 500 nucleotides are preferable where possible, such as longer than about 600 mucleotides, than about 700 nucleotides, than about 800 nucleotides, than about 1000 nucleotides, than about 1200 nvcleotides, than about 1400 nuclectides, or more. it may be preferable that there is complete sequence identity in the sequence used for down-regulation of expression of a target sequence, and the target sequence, though total comdlementarity or similarity of sequence is not essential. One or more nucleotides may differ in the sequence used from the target gene. Thus, a sequence employed in a down-regulation of gene expression in accordance with the present invention may be a wild-type sequence (e.g. gene) selected from those available, or a mutant, derivative, variant or allele, by way of insertion, addition, deletion or substitution of one or more nucleotides, of such a sequence. The sequence need not include an open reading frame or specify an RNA that would be translatable. It may be preferred for there to be sufficient homology for the respective anti-sense and sense RNA molecules to hybridise. There may be down regulation of gene expression even where there is about 5%, 10%, 15% or 20% or more mismatch between the sequence used and the target gene.

Generally, the transcribed nucleic acid may represent a fragment of an Mlo gene, such as including a nucleotide sequence shown in FIG. 2, or the complement thereof, or may be a mutant, derivative, variant or allele thereof, in similar terms as discussed above in relation to alterations being made to a coding sequence and the homology of the altered sequence. The homology may be sufficient for the transcribed anti-sense RNA to hybridise with nucleic acid within cells of the plant, though irrespective of whether hybridisation takes place the desirecd effect is down-regulation of gene expression.

Anti-sense regulation may itself be regulated by employing an inducible promoter in an appropriate construct.

Constructs may be expressed using the natural promoter, by a constitutively expressed promotor such as the CaMV 35S promotor, by a tissue-specific or cell-type specific promoter, or by a promoter that can be activated by an external signal or agent. The CAMV 35S promoter but also the rice actin and maize ubiquitin promoters have been shown to give high levels of reporter gene expression in rice (Fujimoto et al., (1993) *Bio/Technology* 11, 1151–1155; Zhang, et al., (1991) Plant Cell 3, 1155–1165; Cornejo et al., (1993) *Plant Molecular Biology* 23, 567–581).

For use in anti-sense regulation. nucleic acid including a nucleotide sequence complementary to a coding sequence of a Mlo gene (i.e. including hornologues), or a fragment of a said coding sequence suitable for use in anti-sene regulation of expression, is provided. This may be DNA and under control of an appropriate regulatory sequence for anti-sense transcription in cells of interest.

Thus, the present invention also provides a method of conferring pathogen resistance on a plant, the method including causing or allowing anti-sense transcription from heterologous nucleic acid according to the inverticn within cells of the plant.

The present invention further provides the use ofe nucleotide sequence of FIG. 2 or a fragment, mutant, dirivative, allele, variant or homologue thereof, such as any sequence shown or identified herein. for down-regulation of gene expression, particularly down-regulation of expression of an Mlo gene or homologue thereof, preferably in order to confer pathogen resistance on a plant.

When additional copies of the target gene, are inserted in sense, that is the same, orientation as the target gene, a range of phenotypes is produced which includes individuals where over-expression occurs and some where under-ewression of protein from the target gene occurs. When the inserted gene is omly part of the endogenous gene the number of under-expressing individuals in the transgenic population increases. The mechanism by which sense regulation occurs, particularly down-regulation, is not well-understood. However, this technique is well-reported in scientific and patent literature and is used routinely for gene control. See, for example, van der Krol et al., (1990) *The Plant Cell* 2, 291–229; Napoli et al., (1990) *The Plant Cell* 2, 279–289; Zhang et al, 1992 *The Plant Cell* 4, 1575–1588.

Again, fragments, mutants and so on may be used in similar terms as described above for use in anti-sense regulation.

Thus, the present invention also provides a method of conferring pathogen resistance on a plant, the method including causing or allowing expression from nucleic acid according to the invention within cells of the plant. This may be used to suppress Mlo activity. Here the activity of the product is preferably suppressed as a result of under-expression within the plant cells.

As noted, Mlo down-regulation may promote activation of a defence response, which may in turn confer or augment pathogen resistance of the plant, especially resistance to powdery mildew and/or rust (e.g. yellow rust).

Thus, the present invention also provides a method of modulating Mlo function in a plant, the method comprising causing or allowing expression from nucleic acid according to the invention within cells of the plant to suppress endogenous Mlo expression.

Modified versions of Mlo may be used to down-regulate endogenous Mlo function. For example mutants, variants, derivativee etc., may be employed. For instance, expwession of a mlo mutant sequence at a high level may out-compete actvity of endogenous Mlo.

Reduction of Mlo wild type activity may be achieved by using ribozymes, such as replication ribozymes, e.g. of the hammerhead class (Haseloff and Gerlach, 198*, Nature* 334: 585-591; Feyter et al. *Mol*., 1996*, Gen. Genet.* 250: 329–338).

Another way to reduce Mlo function in a plant employs trarsposon mutagenseis (reviewed by Osborne et al., (1995) *Current Opinion in Cell Biology* 7, 406–413). Inactivation of gaenes has been demorstrated via a 'tageted taggng' aporoach using either endogenous mobile elements or heterologous cloned trasposons which retain their mobility in alien genomes. Mlo alleles carrying any insertion of know sequence could be identified by using PCR primers with binding specificities both in the insertion sequence and the Mlo homologue. 'Two-element systems' could be used to stabilize the transposon within inactivated alleles. In the two-element approach, a T-DNA is constructed bearing a non-autonomous transposon containing selectable or screenable marker gene inserted into an excision marker. Plants sing these T-DNAs are crossed to plants bearing a second T-DNA expressing transposaae function. Hybrids are double-selected for excision and for the marker within the transposon yielding $F_2$ plants with tr sed elements. The two-elemant approach has a particular advantage with respect to Ac/Ds of maize, as the transposed Ds is likely to be unlinked to the transposase, facilitating outcrossing and stabilization of the Ds insertion (Jones et al., (1994) *Science* 266, 789–793; Osborne et al., (1995) *Current opinion in Cell Biology* 7, 406–413).

The mlo-based powdery mildew resistance is caused by the inactivation of the Mlo wild type allele, resulting in a recessive resistance phenotype. Substances that inhibit the activity of the Mlo wild type protein may be used to induce the resistance phenotype.

An important hint that complete inactivation of Mlo expression is not essential and may even be detrimental is provided by the description of mutagen-induced mlo resistance alleles that are likely to have retained residual wild type allele activity. These alleles exhibit no detectable spontaneous leaf necrosis which negatively affects photosynthesis rates and yield (Hentrich, W (1979) *Arch. Züchtungsvorsch*., Berlin 9, S. 283–291).

The Mlo protein is predicted to be membrane-anchored by seven transmembrane helices (see e.g. FIG. 7). This structure prediction has been reinforced by recent analysis of Mlo homologues in rice and *Arabidopsis thaliana*. Structure prediction of the *Arabidopsis thaliana* homologue also suggests the presence of seven transmembrane helices. A comparison of the Mlo homologues revealed in addition conserved cysteine residues inthe putative extracellular loops 1 and 3 and high probabilities of amphipathic helices in the second intracellular loop adjacent to the predicted transmembrane helices 3 and 4. Thesecorserved structural motifs in the family of Mlo proteins are reminiscent of C protein coupled receptors (GPCR) described extensively in marmalian systems. GPCRs are known to be activated by ligands and to amplify sigrals intracellularly via heterotrimeric G proteins. Wwithout in any way providing a limitation on the nature or scope of any aspect of thepresent invention, it is predicted that Mlo activates an inhibicory G alpha subunit of heterotrimeric G proteins, thus leading to a downregulation of as yet unknown effector proteins.

The provision herein of Mlo seuence information enables the identification of antagonists of function of the Mlo protein (e.g. GPCR function) Antagonists of Mlo may block receptor activation by its unknown genuine ligand, mimicking recessive mutations in the Mlo gene. Such Mlo antagonist may be used as crop protection ccmpornds for example applied externally to the plant orcrop or here the compound is peptidyl in nature, delivered internally via a biological vector (e.g. recombinant infecting viral particle expressing the antagonistic molecule within target plant cells) or via a transgenic route (plants or plant cells genetical y modified to express the antagonist molecule, perhaps under control of a promoter inducible by an exterally applied compound (eg GST-II. promoter from maize—Jepson et al *Plant Molecular Biology* 26:1855–1866 (1994)) allowing control over the timing of expresion of the mlo inactivation phenotype.

Leaf segments of KLo wild type plants may be tested with a test substance, e.g. from a random or combinatorial compound library, for resistance upon challenge with pathogen such as powdery mildew. The detached leaf segment assay is used as a standard test system to score for susceptibility/resistance upon inoculation with powdery mildew spores. Leaf segments of 7-day-old seedlings of the genotype Mlo RorI may be placed on agar, for example individual wells of 96-well microtiter plates containing 50 $\mu$l agar. Different compounds may be applied to the agar surface in each well at a concentration of about 1 ppm dissolved in DMSO. Around seven days after inoculation of the detached leaf segments with pathogen, such as spores of a virulent powdery mildew isolate, compounds which induce resistance may be recognised by the absence of fungal mycelium on leaf segments in the microtiter plates.

A further selection may be used to discriminate between compounds that act in the mlo pathway and those that confer resistance by other mechanisms, or those which exhibit a direct fungitoxic activity. For this purpose mutants in genes (Ror genes) which may be required for mlo resistance (Freialdenhoven et al., (1996), The Plant Cell 6, 5–14) may be used. Mutants of these genes confer susceptibility to powdery mildew attack despite the presence of mlo resistance alleles. Plants of the genotype Mlo rorl (wild type Mlo protein and defective Rorl gene) may be used, for example, to test compounds which induce resistance on Mlo Rorl genotypes but exhibit susceptibility on the Mlo rorl genotype, enabling selection of candidate Mlo antagonists. Testing candidate compounds identified using a leaf segment test may be jsed to drastcally redce the number of candidate compounds for further n vitro tests.

A further selection step of candidate antagonists may involve heterologous expreasion of the Mlo protein or a fragment thereof (e.g. in a baculovisus insect cell system) and subsequent binding assays with labelled molecules. Specific binding of compouds to cell lines expressing wild type Mlo protein is a good inoicator of their antagonistic mode of action. Analsis of the deduced Mlo protein sequence has provided strong evidence that the protein is anchored in the memrane via seven transmeebane helices and may represent a novel mebber of the so-called serpentine receptor family. The conclusion is supported by the sequence data derived from homologous genes ideatified in barley, rice and Arabidopsis. Seven transmembrane proteins have been shown to be expressed at high level in the Baulovirus/inaect cell system (up to $10^7$ molecules per cell—Tate and Griushamer, 1996, *TIBTECX* 14: 426–430). Since the family of Mlo proteins appears to be restricted to the plant kingdom, this provides a low-background environment for compound tests. Candidate compounds which are labelled, radioactively or non-radioactively, may be tested for specific binding to Sf9 insect cells dresesig the Mlo protein after infecion with a recombinant baculovirus construct. Specificity of the binding may be tested further by Sf9 expression of mutant mlo proteins which carry characterised mutations (e.g. as in Table 1 leading in vivo to resistance.

Thus, in various further aspects the present invention. relates to assays for substances able to interfere with Mlo function, i.e. confer a mlo mutant phenotype, such substances themselves and uses thereof.

The use of Mlo in identifying and/or obtaininga substance which inhibits Mlo function is further provided by the present invention, as is the use of Mlo in identifying and/or obtaining a substance which induces pathogen resistance in a plant.

Agents useful in accordance with the present invention may be identified by screening techniques which involve determining whether an agent under test inhibits or disrupts Mlo function to induce an mlo phenotype. Candidate inhibitors are substances which bind Mlo.

It should of course be noted that references to "Mlo" in relation to assays and screens should be taken to refer to homologues, such as in other species, including rice and wheat, not just in barley, also appropriate fragments, variants, alleles and derivatives thereof. Assessment of whether a test substance is able to bind the Mlo protein does not necessarily require the use of full-length Mlo protein. A suitable fragment may be used (or a suitable analogue or variant thereof).

Suitable fragments of Mlo include those which include residues known to be crucial for Mlo function as identified by mlo mutant alleles (Table 1). Smaller fragments, and analogues and variants of this fragment may similarly be employed, e.g. as identified using techniques such as deletion analysis or alanine scanning. Furthermore, one class of agents that can be used to disrupt Mlo activity are peprides fragments of it. Such peptides tend to be short, and may be about 40 amino acids in length or less, preferably about 35 amino acids in length or less, more preferably about 30 amino acids in length, or less, more preferably about 25 amino acids or less, more preferably about 20 amino acids or less. more preferably about 15 amino acids or less, more preferably about 10 amino acids or less, or 9, 8, 7, 6, 5 or less in lengh. The present invention also encompasses peptides which are sequence variants or derivatives. of a wild type 14lo sequence, but which retain ability to interfere with Mlo function, e.g. to induce an mlo mutant is phenotype. Where one or more additional amino acids are included, such amino acids may be from Mlo or may be heterologolous or foreign to Mlo. Apeptide may also be included within a larger fusion protein, particularly where the peptide is fused to a non-Mlo (i.e. heterologous or foreign) sequence, such as a polypeptide or protein domain.

Peptides may be generated wholly or partly by chemical synthesis. The compounds of the present invention can be readily prepared according to well-established, standard liquid or, preferably, solid-phase peptide synthesis methods, general descriptions of which are broadly available fsee, for example, in J.M. Stewart and J. D. Young, Solid Phase Peptide Synthesis, 2nd edition, Pierce Chemical Company, Rockford, Ill. (1984), in M. Bodanzsky and A. Bodanzsky, The Practice of ?eptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a peptidyl molecule according to the present invention (peptide or polypeptide) is to express nucleic acid encoding it, by use of nucleic acid in an expression system, as discussed elsewhere herein. This allows for peptide agents to be delivered to plants Transgenically, by means of encoding nucleic acid. If coipled to an inducible promoter for expression under control of the user, this allows for flexibility in induction of an mlo phenotype and pathogen resistance. This may allow for any side-effects arising from interference with Mlo function to be moderated.

In one general aspect the present invention provides an assay method for a substance able to interact with the relevant region of Mlo, the method including:

(a) bringing into contact a Mlo polypeptide or peptide ragment thereoof, or a variant, derivative or analogue thereof, and a test comoound; and (b) determining interaction or binding between said polypeptide or peptide and the test compound.

A test compound found to interact with the relevant portion of Mlo may be tested for ability to modulate, e.g. disrupt or interfere with, Mlo function, as discussed already above.

Another general aspect of the present invention provides an assay method for a substance able to induce an mlomurtat phenotype in a-plant, the method including:

(a) bringing into contact a plant or part thereof (e.g. leaf or leaf segment) and a test compound; and (b) determining Mlo unction and/or pathogen resistance and/or stimulation of a defenae response in the plant.

Susceptibility or resistance to a pathogen may be determined by assessing pathogen growth, e.g. for powdery mildew the presence or absence, or extent, of mycelial growth. minding of a test compound to a polypeptide or peptide may be assessed in addition to ability of the test compound to stimulate a defence response in a plant. Such tests may be run in parallel or one test may be performed on a substance which tests positive in another test.

Of course, the person skilled in the art will design any appropriate control experiets with which to compare results obtained in test assays.

Performance of an assay method according to the present invention may be followed by isolation and/or manufacture and/or use of a compound, substance or molecule which tests positive for ability to modulate Mlo function and/or induce pathogen resistance, such as resistance to powdery mildew.

The precise format of an assay of the invention may be varied by those of skill in the art using routine skill and knowledge. For example, interaction between substances may be studied in vitro by labelling one with a detectable Babel and bringing it into contact with the other which has been, immobilised on a solid support. Suitable detectable labels, especially for peptidyl substances include $^{35}S$-methionine which, may be incorporated into recombinantly produced peptides and polypeptides. Recombinantly produced peptides and polypeptides may also be expressed as a fusion protein containing an epitope, which can be labelled with an antibody.

An assay according to the present invention may also take the form of an in vivo assay. The in vivo assay may be performed in a cell line such as a yeast strain or mammalian cell line in which the relevant polypeptides or peptides are expressed from one or more vectors introduced into the cell.

For example, a polypeptide or peptide containing a fragment of Mlo or a peptidyl analogue or variant thereof as disclosed, may be fused to a DNA binding domain such as that of the yeast transcription factor GAL 4. The GAL 4 transcription factor includes two functional domains. These domains are the DNA binding domain (GAL4DRD) and the GAL4 transcriptional activation domain (GAL4TAD). By fusing such a polypeptide or peptide to one of those domains and another polypeptide or pepcide to the respective counterpart, a functional GAL 4 transcription factor is restored only when two polypeptides or peptides of interest interact. Thus, interaction of the polypeptides or peptides may be measured by the use of a repos er gene probably linked to a GAL 4 DNA binding site which is capable of activating transcription of said reporter gesn. This assay format is described by Fields and Song, 1989, Nature 340; 245–246. This type of assay format ean be used in both mammalian cells and in yeast. Other combinations of DNA binding domain and transcriptional activation domain are available in the art and may be prefered, such as the LexA DNA binding domain and the VP60 transcriptional activation domain.

When looking for peptides or other substances which interact with Mlo, the Mlo polypeptide or peptide may be employed as a fusion with (e.g.) the LexA-DNA binding domain, with test polypeptide or peptide (e.g. a random or combinatorial peptide library) as a fusion with (e.g.) VP60. An increase in reporter gene expression (e.g. in the case of β-galactosidase a strengthnning of the blue colour) results from the presence of a peptide which interacts with Mlo, which interaction is required for transcriptional activation of the β-galactosidase gene.

The amount of test substance or comspoid which may be added to an assay of the invention will normally be determined by trial and error depending upon the type of compound used. Typically, from about 0.001 nM to 1 mM or more concentrations of putative inhibitor compound may be used, for example from 0.01 nM to 100 $\mu$M, e.g. 0.1 to 50 $\mu$M, such as about 10 $\mu$M. Greater concentrations may be used when a peptide is the test substance. Even a molecule which has a weak effect may be a useful lead compound for further investigation and development.

Compounds which may be used may be natural or synthetic chemical compounds used in drug screeni. programmes. Extracs of plants which contain several characterised or uncharacterised components may also be used. Antibodies directed to Mlo or a fragment thereof form a further class of putative inhibitor compounds. Candidate inhibitor antibodies may be characterised and their binding regions determined to provide single chain antibodies and fragments thereof which are responsible for disrupting the interaction. Other candidate inhibitor compounds may be based on modelling the 3-dimensional structure of a polypeptide or peptide fragment and using rational drug design to provide potential inhibitor compounds with particular molecular shape, size and charge characteristics. It is worth noting, however, that combinatorial library technology provides an efficient way of testing a potentially vast number of different substances for ability to interact with and/or modulate the activity of a polypeptide. Such libraries and their use are known in the art, for all manner of natural products, small molecules and peptides, among others. The use of peptide libraries may be preferred in certain circumstances.

Following identification of a substance or agent which modulates or affects Mlo function, the substance or agent may be investigated further. Furthermore, It may be manufactured and/or used in preparat on, i.e. manufacture or formulation, of a composition for inducing pathogen resistance in a plant. These may be applied to plants, C. for iniucing pathoge resistance, such as resistance to powedery mildew. A further aspect of the present invention provides a method of inducing pathogen resistance in a plant, the method including applying such a substance to the plant. A peptidyl molecule may be applied to a plant transgerically, by expression from encoding nucleic acid, as noted.

A polypeptide, peptide or other substance able to modulate or interfree witn Mlo function, inducing pathogen resistance in a plant as disclosed herein, or a nucleic acid molecule encoding a peptidyl such molecule, may be provided in a kit, e.g. sealed in a suitable container which protects its contents from the external envi-onment. Such a kit may include instructiaon for use.

Further aspects and embodiments of the present invention will be apparent to those skilled in the art. The present invention will now be exemplified by way of illustration with reference to the following figures:

BRIEF DESCRIPTION OF THE DRAWINGS

FIG. 2 shows an Mlo coding sequence and encoded amino acid sequence according to the present invention (SEQ ID NO:1 and 2). The amino acid sequence predicted from DNA sequences of RT-PCR products from Ingrid Mlo are shown. Nucleotide numbers are given according to translational Start site.

Figure 1:
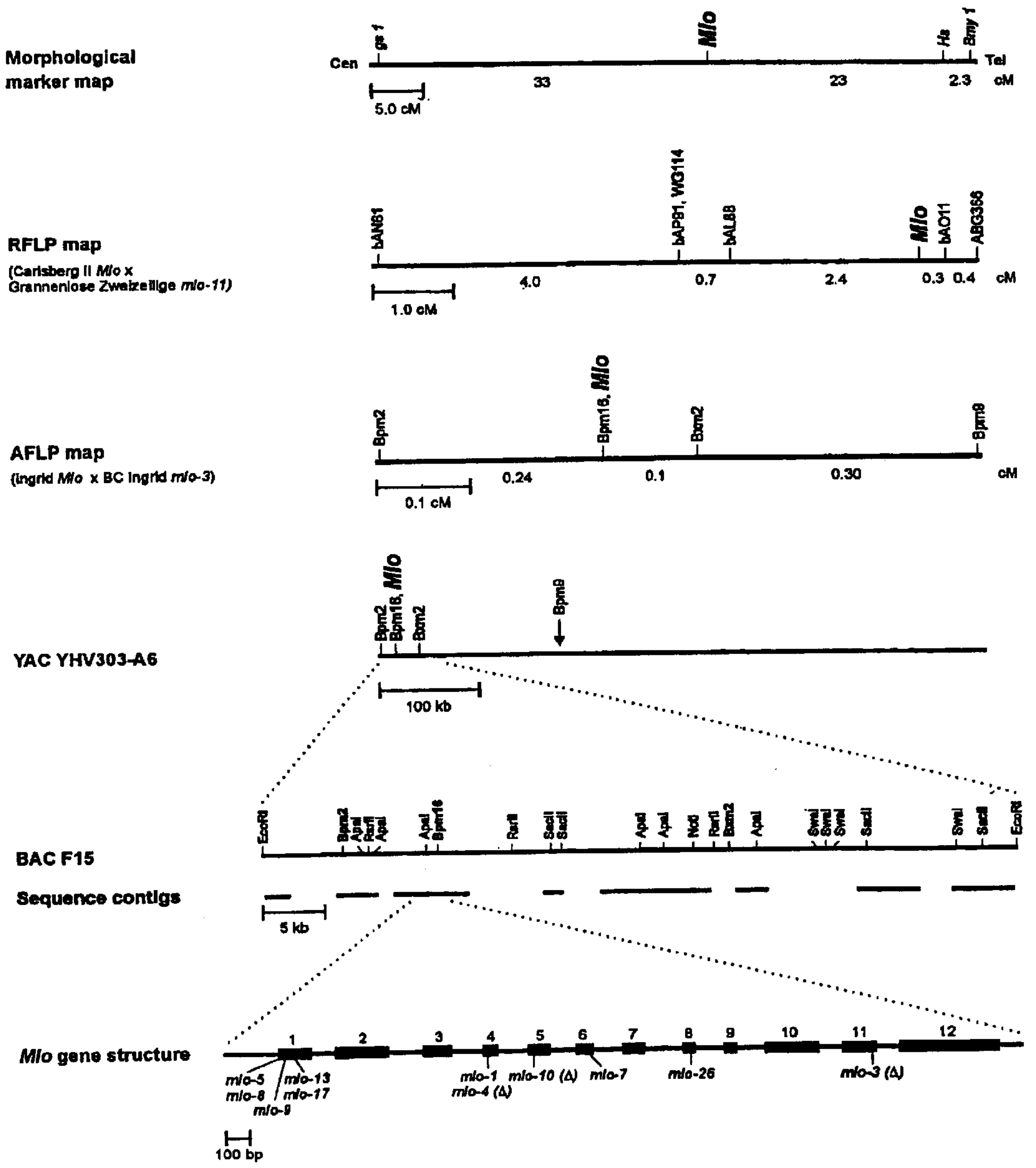
FIG. 1 Positional Cloning of Mlo. The Mlo locus has been mapped with increasing precision on the long arm of barley chromosome 4 using morphological, RFLP and FLP markers. The upper part of the figure presents the genetic linkage maps of these markers relative to Mlo. All genetic distances are indicated in centiMorgan (cM) based on multi-point linkage analysis except for genetic distances between AFLP markers which are calculated by two-point-estimates. The morphological marker map (Jørgensen, 1977) positions Mlo at a distance of more than 20 cM to hairy leaf sheath (Hs) and glossy sheath/spike (gsl). The RFLP marker map is based on the analysis of 257 $F_2$ individuals derived from the cross Carlsberg II mlo Grannenlose Zweizeilige mlo-11. The previously published RFLP map (Hinze et al., 1991) of the same cross was basedon only 44 $F_2$ individuals. The gene was delimited to a 2.7 cM interval bordered by markers bAO11 and bALI88. AFLP markers were identified and mapped as described in Experimental procedures. Their genetic distance to Mlo is based on the cross Ingrid Mlo x $BC_7$Ingrid mlo-3. The crucial result of the AFLP analysis has been the identification of two markers, Bpm2 and Bpm9, defining an 0.64 cM interval containing the Mlo locus and one marker (Bpm16) cosegregating with Mlo on the basis of more than 4,000 meiotic events. Marker Bxm2 which is located 0.1 cM telomeric to Mlo was derived from BAC F15 template DNA (see below). One YAC clone, YAC YHV303-A6, containing the cosegregating marker Bpm16 and two flankLg loci (Bpm2 and Bpm9). is shown in the middle section of the figure. The position of marker Bpm9 was only roughly estimated within the YAC clone as indicated by the arrow. The isert of BAC F15 represents a 60 kb subfragmetn of this YAC as indicated inthe lower part of the Figure. After the identification of AFLP marker Bpm2 in BAC F15, marker Bxm2 was discovered and positioned 0.1 cM in telomeric orientation of Mlo. The approximate physical position of AFLP msrkers Bpm2, Bpm16, and Bxm2 (spanning an interval of approxamately 30 kb) as well as the location of some rare occurring restriction sites are indicated. Dashed lines below the schwatic representation of RAC F15 DNA snow the positio of the largest established DNA sequence contigs. The structure of the Mlo gere is given schematically in the bottom line of the Figure. Exons are highlighted by black boxes. Positions of mutational events are indicated for the eleven tested mlo alleles. Mutant alleles carrying deletions in their nucleotide sequence are marked with a $\Delta_7$ the remaining mutant alleles represent single nucleotide substitutions resulting in amino acid exchanges in each case.

A DNA of the parental lines mlo-B and mlo-1 and two homozygous susceptible (S, Mlo Mlo) and two resistant (R, mlo moo) progenies derived from two susceptible F2 plants (designated 1 and 2) were tested. The DNAs in lanes S and R represent selection $F_3$ individuals from $F_3$ families obtained by selfing the susceptible $F_2$ individuals 1 and 2. Note that susceptible $F_2$ individuals are expected to be heterozygous at Mlo in this section scheme. Infraction phenotypes were scored seven days after inoculation with the mlo avirulent isolate K1. DNA from a third susceptible dnc-idual of this heteroallelic cross (see Table 7) is not included in this Figure.

B DNX of the parental liaes mlo-5 and mlo-1 and seven homozygous susceptible (S, Mlo Mlo) and seven resistant (R, mlo mlol progeny derived from seven susceptible $F_2$ plants (designated 1 to 7) were tested. The DNAs in ianes S and R represent selected $F_3$ individuals from $F_3$ families obtained by selaing the susceptible $F_2$ individuals 1 to 7. DNA was analyzed from two further susceptible individuals of this heteroallelic cross only in the $F_2$ generation (8* and 9*).

FIG. 5 shows an alignment of genomic sequences covering the barley Mlo gene and a rice homologue isolated via crosshybridizaeion with a barley gene specific probe (SEQ ID NOs:3 and 4). The top line shows the barley Mlo genomic DNA sequence (exon sequences underlined). The bottom line shows the rice genomic sequence containing the rice Mlo homologue.

FIG. 6 shows an alignment of genomic sequences carrying the barley Mlo gene and a barley homologue isolated via croashybridization with a barley gene specific probe (SEQ ID NOs:5 and 6). The top line shows the barley Mlo genomic DNA sequence (exon sequences underlined). The bottom line shows the genomic sequence containing the barley Mlo homologue.

FIG. 7 Nucleotide and Deduced Amino Acid Sequence of the Barley Mlo cDNA (SEQ ID NOs:7 and 8). The nucleotide and the deduced amino acid sequence are based on the combined data of RT-PCR and RACE obtained from experiments using RNA of cultivar Ingrid Mlo. The stop codon is marked by an asterisk, the putative polyadenylation signal is underlined and the detected termini of RACE products are indicated by arrows above the sequence. Positions of introns an indentified by comparison with corresponding; genomic clones are labelled by triangles below the nucleic acid sequence. Six predicted transmembrane spanning helices according to the MEMSAT algorithm (Jones et al., 1994) are boxed in grey colour. A putative nuclear localization signal (K-K-K-V-R) and cavein kinase II site (S-I-F-D) in the carboxy-terminal half of the protein are shown in bold type.

FIG. 8 shows genomic sequence of rice (*Oryza sativa*) homologue including coding and flanking sequences (SEQ ID NO:9).

FIG. 9 shows genomic sequence of barley (*Hordeum vulgare*) homologue including coding and flanking sequences (SEQ ID NO:10).

FIG. shows cDNA sequence of rice homologue.

FIG. 11 (SEQ ID NO:12) shows cDNA sequence of barley homologue (SEQ ID NO:11).

FIG. 12 shows CDNA sequence of *Arabidopois thaliana* homologue (SEQ ID:NO:13).

FIG. 13 shows amino acid sequence of rice homologue. (SEQ ID NO:14).

FIG. 14 shows amino acid sequence of barley hoologue (SEQ ID NO:15).

FIG. 15 shows amino acid sequence of Arebidopsi homologue (SEQ ID NO:16).

Figure 16A:
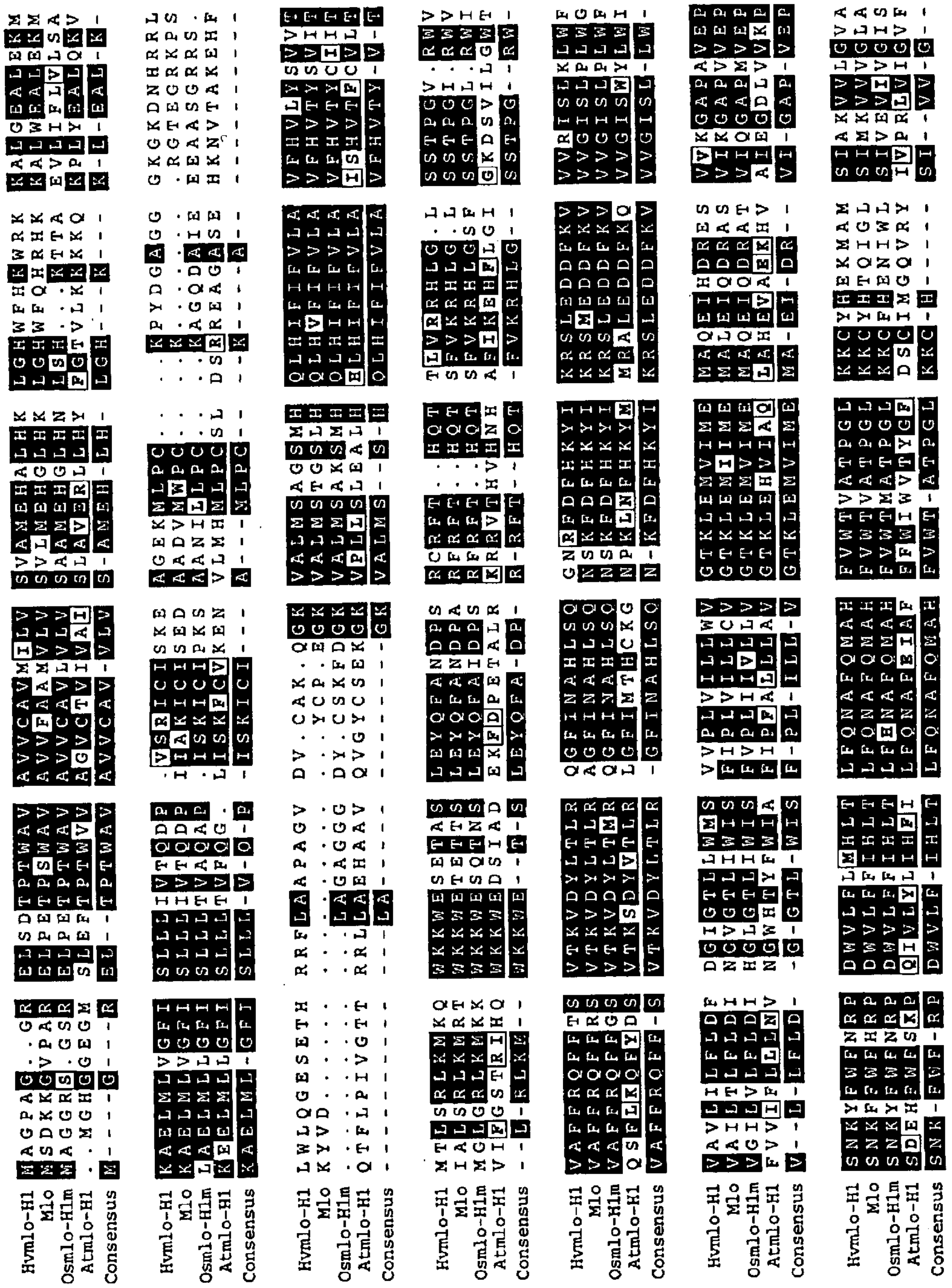
Figure 16B:
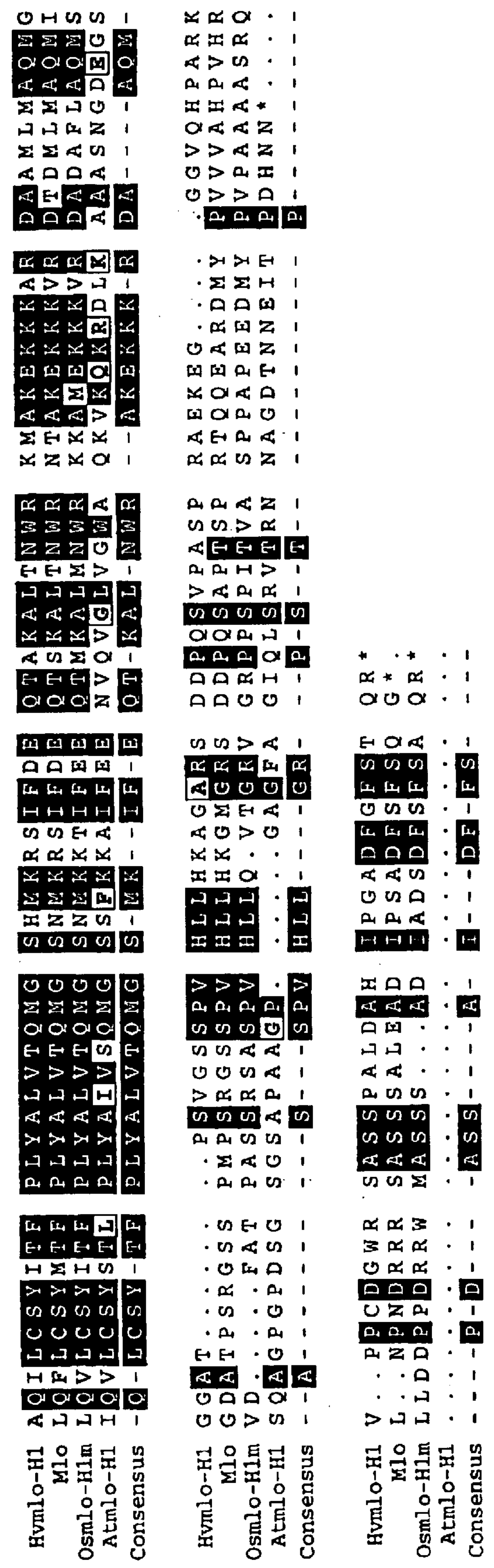

FIG. 16 shows a pretty box of amino acid sequences of Mlo, barley, rice and Arabidopsis homologues (SEQ ID NOs:17–19).

All documents mentioned in this document are incorporated by reference.

EXAMPLE 1

Cloning of Mlo of Barley

Targeted Search for AFLP Markers Tightly linked to Mlo

Efforts to increase the DNA marker density around Mlo were coordinated with attempts to construct a local high resolution genetic map. An alternative possibility would have beef to extend the population size of the characterized cross Carlsbezg II Mlo x Grannenlose Zweizejlige mlo-11 (Hinze et al. 1991) but it was felc to be advantageous to establish a high resolution map starting out from one of the available Bc mlo lines and its recurrent parent line. Importantly, the donor parent of the BC line represents a different; genetie background in comparison to the recurrent parent line. In this way, searching for linked AFLP markers could be stated in parallel with generating a large mapping population from a cross between the same genetic lines. In addition, the DC line based cross allowed testing of colinearity of DNA markers in the vicinity of Mlo as determined from the cross Carlsberg II Mlo x Grafzenlooe Zweizeilige mlo-11 (Ninze et al. 3991). For the new cross a mlo-3 backerous (BC) line was used that had been backcrossed seven times into the genetic background Ingrid ($BC_7$ Ingrid mlo-3; Hizie et al., 1991). The line was previously characterized to carry a relatively small introgressed DNA segment on barley chromosome 4. In addition, the donor parent line Malteria Heda mlo-3 exhibits in comparison to DNA from the recurrent parent Ingrid polymorphisms with most of the identified RFLP loci linked to Mlo. Thus, by searching polymorphisms only between two DNA templates, from lines Ingrid Mlo and $BC_7$ Ingrid mlo-3, we hoped to increase the density of DNA markers with AFLPs aroundfMlo in a targeted manner.

The same two lines were crossed to establish a segregating population for high resolution mapping of DNA markers, formally representing an eigth backcross. $F_2$ individuals were scored-for mlo resistance after powdery mildew inoculation with isolate KS (virulent on Ingrid Mlo and avirulent on $BC_7$ Ingrid mlo-3). Initially, only a small fraction of the $F_2$ (77 individuals). was analyzed for recombination events with flanking RFLP markers. Analysis of four identified recombinants (designated 8-32-2, 7-38-4, 1-34-1, and 1-49-4) indicated colinearity of marker order in this cross compared to the previously analyzed cross Carlsberg II Mlo x Grannenlose Zweizeilige mlo-11 (Hinze et, al., 1991). Several of the 77 $F_2$ seedlings which exhibited a susceptible phenotype and heterozygosity for the tested flanking DNA marker loci (bAO11, bAL88/2, and bAP91; Hinze et al., 1991) were grown to maturity to provide further selfed seed material segregating for Mlo/mlo-3 in the $F_3$ generation. In total, leaf material was harvested for high resolution marker mapping from 2,026 individuals derived from either the selfed $F_2$ or $F_3$ generation.

AFLP marker candidates were identified by testing all possible Pgc I/Mse I primer combinations (1,024) extending into genomic sequences up to nucleotide positions +2 and −3, respectively. Similarly. almost 1,900 Eco RI/Mse I primer combinations (+3/+3) have been analyzed. Four DNA templates were included in this analysis: Ingrid Mlo, $BC_7$ Ingrid mlo-3, a DNA pool of two phenotypically mlo resistant F2 individuals, and a DNA pool of mine phenotypically susceptible $F_2$ individuals. The resistant and susceptible $F_2$ individulas which were included as DrA pools in the AFLP search had been selected from the above mentioned RFLP analysis of 77 $F_2$ segregacts. The pooled $F_3$ DNA eabled us to control whether candidate poLymorphisms detected between template DNA from the parents were heritable traits in the F2. All identfied AFLP candidate markers have been re-exaimined with eight DNA templates: Ingrid Mlo, $BC_7$ Ingrid mlo-3, DNA pools from individuals of three $F_3$ famiies which were phenotypically. iomozygous susceptible (MloMlo) according to K1 inoculation eriments; DNA of three resistant $F_2$ individuals. A total of 18 Pst I/Mse I and 20 Eco RI/Mse I primers were confirmed based on the selection procedure.

The number of identified AFLP mararkers made it useful to assign them first roughly to marker intervals based on the RFLP map around Mlo. It was hoped that this approach should enable both evaluation of the distribution of AFLPs among previously identified RFLP intervals close to Mlo and selection of a pair of flanking AFLP markers with which recombinants could be identified among the 2,026 segregants. For AFLP assignment we used those four recombinants that had been identified with RFLP markers out of the above mentioned small sample of 77 $F_2$ segregants from Ingrid Mlo x $BC_7$ Ingrid mlo-3 (two recombinants in interval bAP91-bAL88, one in Mlo-bAO11, and one in bAO11-ABG366). A total of 18 AFLPS were found to be located within a genetic distance of approximately 3.5 cM including Mlo.

Construction of a High Resolution AFAP Map Around Mlo

A two-step procedure was used to construct the high resolution AFLP map. First, all 2,026 segregants were screened for recombination events between two AFLP markers on opposite sides of Mlo and subsequently only the few identified recombinants were used to map all the identified AFLPs in the 3.5 cM target interval. AFLP markers Bpm1 and Bpm9 were chosen, detecting each allelic DNA fragments in Ingrid Mlo and $BC_7$ Ingrid mlo-3 and located on opposite sites of Mlo to screen DNA templates of the segregants for recombination events. Alternatively, the search for recombinants could have been carried out with the flanking RFLP markers bAO11 and bALS8. However, although the conversion into cleaved amplified polymorphic sites (CAPS) was successful for both markers, difficulties to display the alleles of both loci simultaneously from crudely purified genomic DNA were encountered. A total of. 2,026 individuals ($F_2$or $F_3$ segregants) were screened simultaneously with AFLP markers Bpm1 and Bpm9 and 98 recombinants were identified. AFLP analysis was subsequently carried out with each of the 98 DNA templates of the recombinants to identlfy the alleles of each of the identified of AFLP loci. The recombinants have been selfed and inoculation experiments with powdery mildew isolate K1 were performed using at least 25 individuals of each recombinant family to deduce the alleles of the previous generation at the Mlo locus. The obtained data enabled the construction of a high resolution map around Mlo based on more than 4,000 meiotic events and a resolution of at least 0.025 cM derived vla two-point estimates. The essential result has been the identification of a DNA marker cosegregating With Mlo (Bpm16) and two flanking markers (Bpm2 and Bpm9) at a distance of 0.25 and 0.4 cM respectively (FIG. 1).

Construction of a Large Insert Size Barley YAC Library, Isolation of Bpm16 Containing YACs, and Physical Delimication of Mlo The genetic evidence indicates that nlo resistance is due to loss of function in the kao wild type allele. Therefore, it was decided to establish a large insert size YAC library from cultivar Ingrid Mlo into vector pYAC4 (Burke et al., 1987; Hieter, 1990). Megabase DNA suitable for YAC cloning experiments was prepared in mg amounts from mesophy11 protoplasts of five-day-old seedlings according to a modified protocol described by Siedler and Graner (1951). The DNA was partially digested with Eco RI in the presence of Eco RI methyltransferase to obtain DNA fragments after preparative pulsed-field gel electrophoresis (PFGE) in the size range of 500–600 kb. After ligation with Eco RI digested pYAC4, the DNA was transformed into yeast strain AB1380 and colonies carrying recombinant pYAC4 DNA were selected on solidified synthetic complete medium lacking tryptophan and uracil (Sherman et al., 1986). Forty randomly selected yeast colonies were tested for the presence of barley DNA using labelled barley genomic DNA in Southern experiments. The size of the YAC inserts was found after PFGE separations to vary between 500 and 800 kb. On average a genetic distance of 0.2 cM was expected to be represented on the individual recombinant YAC clone. A total of ~40,000 clones representing four barley genome equivalents have been generated.

Four YAC clones (designated 303A6, 322G2, 400H11, and 417D1) have been isolated with marker Bpm16 cosegregating with Mlo. Their insert size was determined by PFGE to be 650, 710, 650, and 820 kb respectively. AFLP analysis had shown that three of these clones ($303A6_1$ 322G2, and 417D1) contain also both flanking marker loci whereas clone 400H11 contains only loci Bpm16 and Bpm2. These findings strongly suggested that the Mlo gene had been physically delimited on recombinant YAC clones 303A6, 322G2, and 417D1.

YAC 303A6 was chosen for subcloning experiments into BAC vector pECSBAC4 containing a unique Eco RI site (Shizuya et. al., 1992; the vector pECSBAC4 is described by Frijters and Michelmore, 1996; submitted). Total yeast DNA of this clone was partially digested with Eco RI to obtain DNA fragments with an average size of 50 kb and ligated into Eco RI digested and deposphorylated BAC vector. Bacterlal colonies containing YAC 30A6-derived DNA in pECSBAC4 were identified by replica colony hybridization exeriments. One set of colony containing membranes was hybridized wich labelled yeast AB11380 DNA and the replica set was hybridized with labelled PFGE-purified YAC303A6 DNA. Recombiat BAC clones cotaining the ALP locus Bpm16 were Subsequently identified using the cloned 108 bp Par I/Mse I genomc Bpm16 fragment as a probe in colony hybridization experiments.

One BAC clone, BAC P15, containing an insert of ~60 kb was chosen for further detailed studies. It was found that the recombinant BAC clone contained in addition the AFLP marker locus Bpm2, but not Bpm9. At this point the BAC P15 insert DNA indicated successful physical delimitation in telomeric orientation but it was an open question whether the insert would contain bordering sequences in centromeric direction. Instead of constructing a BAC contig between Bpm 16 and Bpm9, the option to develop new polymorphic markers from BAC F15 was chosen. An allelic Xma I/Mse I polymorphism (designated B) was identified between the parental lines Ingrid Mlo and $BC_7$ Ingrid mlo-3.

An analysis of the 25 recombinant individuals earrying recombination events within the Mlo containig interval Bpm2-Bpm9 enabled mapping of Bxm2 in centrometric orientation at a distance of 0.1 cM from Mlo. Only four out of the 16 available recombinants in the interval Bpm9-Mlo and none of the 9 recombinants in the interval Mlo-Bpn2 were found to exhibit a recombination event between Bxm2 and Mlo. It was concluded that Mlo had been physically delimited on BAC F15 between marker loci Bpm2 and Bxm2 (FIG. 1).

Identification of the Mlo Gene and Mlo Mutants

A random sequencing project was initiated to determine sequence contigs of the ~60 kb insert of BAC F15 before marker Bxm2 was identified and shown to delimit the gene in telomeric orientation. In parallel, a physical map was generated (FIG. 1). The physical map indicated that the flanking markers Bpm2 and Bxm2 are physically separated by ~30 kb. The ru sequence contigs were searched for regions of high coding probability using the UNIX versions of the STADEN program package. Only one sequence contig of almost 6 kb, including the cosegregating marker Bpm16, revealed an extensive region of high coding probability.

Figure 3:
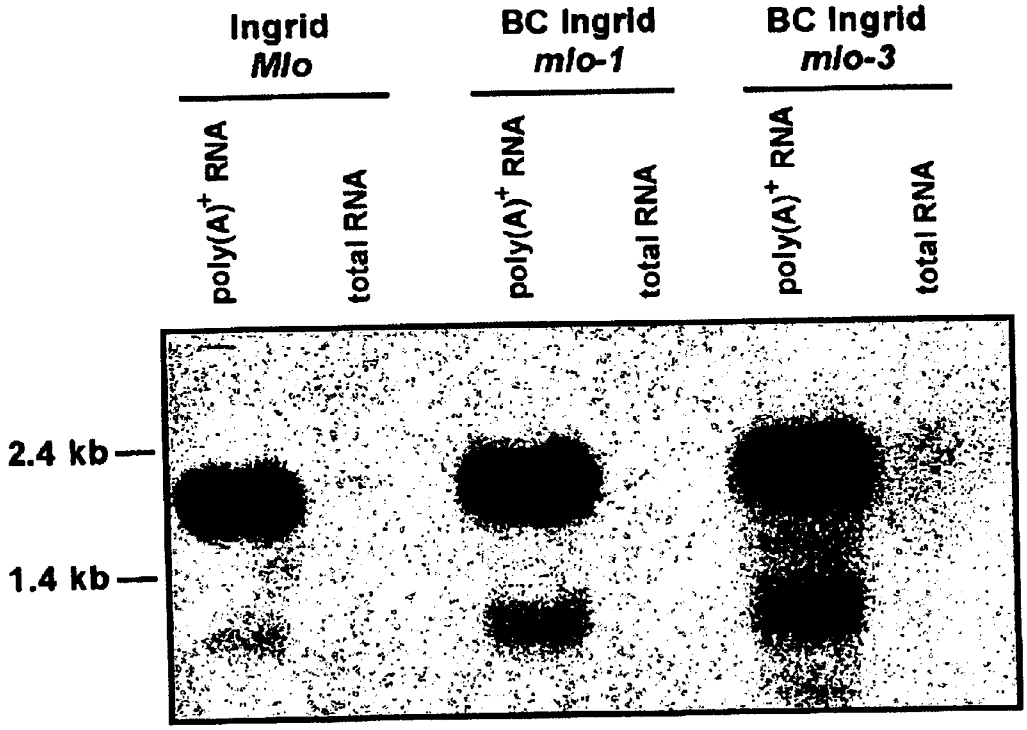
FIG. 3 Northern Blot Analysis of Mlo Transcript Accumulation. Total RNA (20 $\mu$g) wnd poly(A)$^+$ RNA (5 $\mu$g) of seven-day-old uninfected barley primary leaves of one wild type (cultivar Ingrid Mlo) and two mutant (BC Ingrid mlo-1, BC Ingrid mlo-3) cultivars were isolated, separated on a 1.2% formaldehyde gel and transferred to a nitrocellulose membrane (Hybond). The filter was probed under stringent conditions (Sambrook et al., 1989) with the radioactivity labelled full size RT-PCR product derived from Ingrid Mlo (FIG. 7). A clear signal is detected only in the lanes containing poly(A)$^+$ RNA. The signal corresponds to a size of approximately 2 kb.

RT-PCR reactions were performed with total leaf RNA derived from cultivar Ingrid Mlo using a series of primers deduced from regions which indicated high coding probabilities. and obtained in each case a distinct amplification-product. Sequencing of the largest RT-PCR products revealed a single extensive open reading frame of 1,602 bp (FIG. 2). The deduced putative protein of 533 amino acids has a molecular weight of 60.4 kdal. The ~1.7 kb RT-PCR product was used as a hybridization probe and detected a single RNA transcript of ~1.9 kb length. (FIG. 3). A comparison of the genomic sequence and the largest RT-PCR fragment reveals 12 exons and 11 introns. each flanked by the characteristic splice site sequences (FIG. 1).

Because marker Bpm16 is located at the 3' end of the above described gene (exon 11) and cosegregates with the Mlo locus, we started a direct PCR sequencing of the various available mutagen-4nduced mlo resistance a1leles. We ident fied in 14 out of 15 tested mutant alleles nucleotide alterations which result either in single amino acid alterations, deletions or frame shifts of the wild type sequence (Table 1). The suspect that mutant allele mlo-2 is located within the promoter- or 5' untrarnslated sequences. The region is notoriously difficult to be sequenced via direct PCR sequencing from genomic DNA templates but emerimenzs using a aeries of nested primers are likely to solve this problem. In summay, the comparative sequencing of genomic DNA from various mutant mlo lines and their respective Mlo wild type ciltivars provided strong evidence that Mlo has been identified.

Intragenic Reccmbinacts

It had been the intention to provide a chain of evidence for the molecular isolation of ilo which did not rely upon complemetation experiments via transgenic barley plants. We had chosen to develop an unusual genetic tool to confirm that the identified gene represented Mlo. It was reasoned that if the mutations observed in the above described gene caused resistance to the powdery mildew fungus, recombination events between mutant allele sites should restore wild type sequences. It was predicted that thoes intragenic recombinants would exhibit susceptibility upon powdery mildew attact.

A crossing scheme was devised involving mlo resistance alleles mlo-1, mlo-5, and mlo-8. The mutant preformed as shown (mlo-1and mlo-8). Intermutant crosses were preformed as shown in Table 2 generating in each case the 10 $F_1$ plants. $F_2$ populations were obtained by self-fertilization. $F_2$ seedlings were screened for rare susceptible individuals after inoculation with powdery mildew isolated K1 which is virulent on each of hte parantal Mlo wild type cultivars. Suscaptible $F_2$ individuals were identified with a frequency of $\sim 6\times 10^{-4}$. In contrast, if comparabel numbers of progenies from selfings of each of the mlo mutants were tested for resistance of K1, no susceptible seedling was identified. This finding strongly indicated that the majority of the susceptible individuals derived from the intremutant crosses were not due to spontanous revrsion events of the mutatn of mlo alleles. Inheritance of the susceptible $F_2$ famlies. Each of the F2 individuals segregated susceptible and resistant $F_3$ individuals indicating hetrozgosity for alleles conferring resistance/susceptibility in the $F_2$. Homozygous susceptibel $F_3$ progeny were isolated for the majority of susceptible $F_2$ individuals by selfing of $F_3$ individuals and subsequent identification of $F_4$ famlies in which only susceptible individuals were detected.

Figures 4A, 4B:
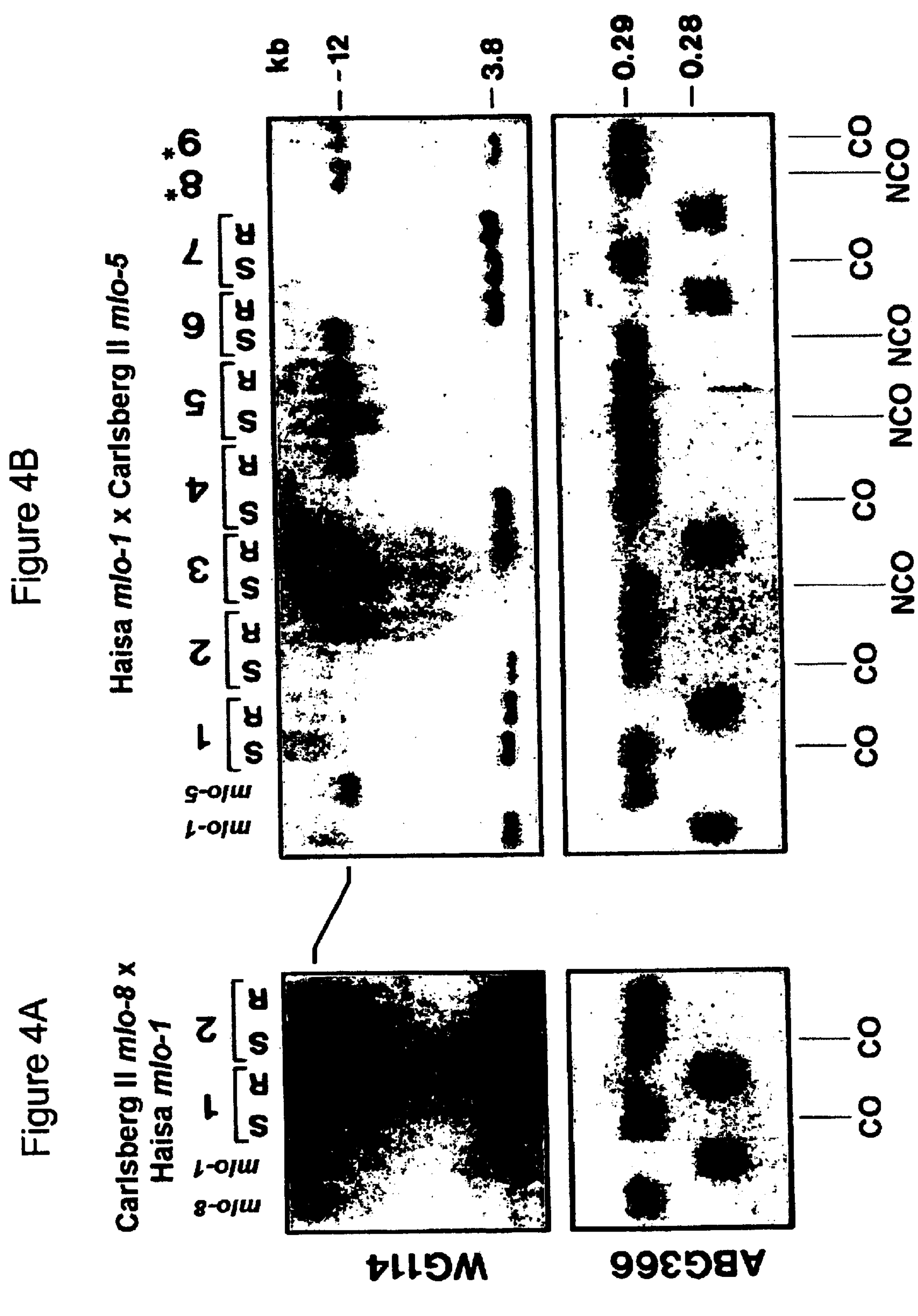
FIG. 4 Southern Blot Analysis of Intragenic Recombinants derived from mlo heteroallelic crosses. The alleles of two RFLP markers flanking Mlo on opposite sides of either susceptible $F_2$ individuals or homozygous susceptible and homozygous resistant progeny were determined by Southern blot analysis. Plant DNA (10 $\mu$g) of the individuals were digested with Pst I (A) or Hae III (B) and hybridized with the radioactively labelled RFLP markers WG114 (upper panel; maps 3.1 cM in centromeric orientation to Mlo; see FIG. 1) and ABG366 (lower panel; maps 0.7 cM in telomeric orientation to Mlo; see FIG. 1) according to standard procedures (Sambrook ec al., 1989).

A molecular analysis of the susceptible individuals has been performed using RFLP markers known to be tightly linked (<3 cM) on each side of the Mlo locus (FIG. 4). RFLP marker WG114 maps in cent-omeric orientation relative to Mlo, marker ABG366 maps in the direction of the telomere. Detected RFLP alleles are shown for the intermutant crosses mlo-8 x alo-1 (A) and mlo-1 x mlo-5 (B). DNA was analyzed either from susceptible $F_2$ individuals (indicaed b *) or from homozygous susceptible (S) and homozygous resistant (R) $F_3$ progey obtained from selfed susceptible $F_2$ individuals.

The homozygous susceptible $F_3$ progeny from the susceptible $F_2$ plant #1 of cross mlo-8 x mlo-1 (FIG. 4) reveals the WG114 allele derived from the mlo-2 parent in cectromeric orientation next to Mlo and the ABG366 allele from the mlo-8 parent in telomeric orientation to Mlo. The homozygous xesistant $F_3$ progeny from $F_2$ plant #1; of this cross reveals in contrast only the flanklng marker alleles derived from parent mlo-2. The finding strongly suggested that susceptibility in $F_2$ plant #1 is caused by a cross-over type of recombination in the preceding meiosis of one chromosome which results in a restoration of the Mlo wild type allele whereas the second $F_2$ chromosome of individual 1 contains a functionally unaltered mlo-1 allele. The allelotypes of the RFLP loci of the homozygous susceptible $F_3$ progeny from susceptible $F_2$ plant #1 are identical to the one described above. However, flanking marker alleles from the homozygous resistant $F_3$ progeny of this individual are in both cases derived from the mlo-8parent. It is concluded that again a cross-over type of recombination restored one Mlo wildtype allele in the susceptible $F_2$ individual #2.

Nine susceptible $F_2$ individuals were recovered from the cross mlo-1 x mlo-5 (FIG. 4). For susceptible $F_2$ individuals #1 to #7 both homozygous susceptible and homozygous resistent $F_3$ progeny were analyzed at the DNA level. Note that only DNA from the heterozygous susceptible $F_2$ individuals was analyzed in the case of individuals #8 and #9 (marked by a *). The following allele patterns with respect to the flanking RFLP loci were observed: (i) homozygous resistant $F_3$ progeny showed ro on both sides of Mlo either only the allelotypes of loci WG114 and ABG366 derived from the mlo-1 parent (individuals #1, #3, #6, #7) or only the allelotypes derived from the mino-5 parent (individuals #2, #4, #5). (ii) Homozygous susceptible $F_3$ progeny showed in contrast either only the allelotypes of both loci derived from the mlo-5 parent (no. #3, #5, #6) or they showed different allelotypes on both sides of Mlo (individuals #1, #2, #4, #7). (iii) The homozygous susceptible $F_3$ progeny with different allelotypes on both sides always contain in centromeric orientation the mlo-1 derived WG114 allele and in telomeric orientation the mlo-5 derived ABG366 allele. (iv) The heterozygous susceptible $F_2$ individual #8 reveals on either side next to Mlo only the alleles derived from parent mlo-5. The heterozygous susceptible individual #9 reveals in centromeric orientation alleles derived from both parents mlo-2 and Mlo-5 whereas only the mlo-5 derived allele is detected in telomeric orientation. A comprehensive interpretation of the data suggests that susceptibility in $F_2$ individuals no. #1, #2, #4, #7, and #9 is caused by a cross-over type of recombination restoring the Mlo wild type allele. Non cross-over types of recombination may have restored the Mlo wild type allele in individuals no. #3, #5, #6, and #8.

A compilation of the detected flanking RFLP alleles of all isolated susceptible $F_2$ individuals or homozygous $F_3$ progeny is shown in Table 3. Note that individual #3 of the cross mlo-8 x mlo-1 is not shown in FIG. 4. The compilation reveals that (i) cross-over types of recombination (CO) and non cross-over types of recombination (NCO) are found with a ratio of 7:5, (ii) cross-over types of recombination are resolved unidirectional, and (iii) NCO recombinants were not observed with parental mlo-1-linked RFLP alleles.

The CO type intragen-c recombinants isolated from heteroallelic mlo crosses were used to test whether wild type sequences of the Mlo candidate gene had been restored. For the three relevant alleles mlo-1, mlo-5, mlo-8 alleles candidate mutation sites have been identified (Table 1 and 4) Direct PCR sequencing of genomic DNA of susceptible intragenic recombinants derived from both heteroallelic crosses mlo-1 x mlo-8 and mlo-1 x mlo-5 revealed restoration of wild type sequences (Table 4). This observation strongly suggests that the intragenic cross over event occurred between nucleotide −1 and +483 in the former and +3 and +483 in the latter cross (according to translational start site). Thus, the molecular analysis of seven intragenic recombinants from two heteroallelic crosses provides final proof that the above described candidate gene represents Mlo.

EXAMPLE 2

Homologues of the Identified Mlo Gene

The available expressed sequence tag (EST) databases of *Oryzae sativa* (rice) and *Arabidopsis thaliana* were searched for homologous protein sequences. Five Arabidopsis cDNA clones were identified whose deduced amino acid sequences show substantial similarity to the Mlo protein. Remarkable is cDNA clone 205N12T7 which reveals a chance probability of 1.2 $e^{-45}$. In addition, at least one significant homologue was found in rice (OSR163811A)

A rice BAC library (Wang et al., 1995) has also been screened with a labelled barley genomic fragment containing Mlo. A BAC clone containing an insert of ~23 kb was isolated. Subsequent subcloning enabled isolation of a 2.5 kb Pst I genomic rice fragment showing strong cross-hybridization with the barley Nlo gene probe. DNA sequencing of this fragment revealed remarkable DNA sequence similarities within exon sequences of the barley Mlo gene (FIG. 5).

Finally, a 13 kb λ genomic barley clone derived from cultivar Igri (Stratagene) was isolated with a labelled barley genomic fragment containing Mlo. The nucleotide sequence derived from a subcloned 2.6 kb Sac I fragment reveals again extensive sequence similarities. to the Mlo gene (FIG. 6). The location of the barley Mlo homologue within the genome is not within BAC F15 DNA.

In summary, there is conclusive evidence for Mlo homologues both in a monocotyledonous and a dicotyledonous plant species.

Discussion

Any speculation as to mode of action of Mlo and mlo nucleic acid and polypeotides should provide no limitation on the nature or scope of any aspect or embodiment of the present invention.

In plants, resistance to pathogens is frequently determined by dominant resistance genes, whose products are assumed to recognize pathogen derived avirulence gene products. This mode of pathogen defence follows Flor's gene-for-gene hypothesis (Flor. 1971). Recently, several 'gene-for-gene' type resistance genes have been molecularly isolated (Martin et al., 1993; Bent et al., 1994; Jones et al., 1994; Mindrinos et al., 1994; Whitham et al., 1994; Grant et al., 1995; Lawrence et al., 1995; Song et al., 1995). The surprising finding is that the deducedproteins share remarkable similar structural domains although they trigger resistance reactions to pathogens such as viruses, fungi, and bacteria (Dangl, 1995; Staskawicz et al., 1995). The isolated genes code for proteins that either contain a leucine-rich region (LRR), with or without an attached nucleotide binding site (NBS), indicative of ligand-binding and protein-protein interaction or encode a simple serine/threonine kinase. A structural combination of LRR and the kinase domain has been reported in the deduced protein from the rice Xa21 resistance gene (Song et al., 1995). The structural similarity of resistance genes in 'gene-for-gene' defence makes the existence of a common underlying resistance mechanisms likely.

Resistance mediated by recessive resistance alleles of the Mlo gene differs in various aspects from 'gene-for-gene' resistance (see introductory comments above). The molecular isolation of the Mlo gene and the sequencing ofvarious mutation-induced mlo alleles described here, confirms previous interpretations from combined mutational and Mendelian genetic studies (Hentrich, 1979; Jørgensen, 1983). It is concluded that defective alleles of the Mlo Locus mediate broad spectrum resistance to pathogens such as the powdery mildew pathogen. This is inconsistent with the involvement of a specific recognition event of a pathogen-derived product as has been proposed for race-specific resistance genes.

Pleiotropic effects of mlo alleles have provided some clues towards the developmentof a molecular concept of the observed broad spectrum resistance response.

Firstly, aseptically grown mlo plants exhibit at a high frequency a spontaneous formation of cell wall appositions (CWAs) in leaf epidermal cells (Wolter et al., 1993). Those CWAs are usually formed in response to attempted pathogen penetration directly beneath the fungal apressorium. CWAs are believed to form a physical barrier against pathogen ingress and have been implicated repeatedly in mlo mediated resistance (Bayles, 1990).

Secondly, at a later stage, the plants develop macroscopically detectable leaf necrotic flecks. The spontaneous leaf necrosis response has been extensively studied with a unique collection of 95 chemically-induced mlo alleles (Hentrich, 1979). The alleles were classified as either showing a gradually different infection phenotype upon infection of a mixture of nine powdery mildew isolates. Those mlo alleles which give rise to an intermediate infection phenotype (i.e. development of a considerable number of sporulating fungal colonies upon inoculation) showed no detectable spontaneous leaf necrosis whereas the category of the most effective resistance alleles exhibits pronounced necrosis in the absence of the pathogen. Thus, there is solid evidence that the former catagory of mlo alleles retain residual wild type allele activity and those alleles appear to exhibit no detectable spontaneous leaf necrosis.

Thirdly, a constitutive expression of defence-related genes has been observed in mlo seedlings grown urder mildew-free conditions—in primary leaves when 10–11 days old; this includes genes of the PR-1 family, chitinases and peroxidases.

We have shown that mlo in barley confers increased resistance to different types of yellow rust (*Puccinia struciformis*) when a one to one mixture of talcum powder and spores were aviblown onto leaves of mlo barley plants after onset of constitutive expression of defence related genes (10–11 day old mlo seedlings).

Thus, it appears that multiple defence-associated responses are constitutively expressed in mlo plants.

The temporal relationship of these events is interesting: the onset of constitutive defence-related transcript accumulation is detected in 11 day-old seedlings and precedes CWA formation which is followed by the appearance of macroscopically visible leaf necrosis. Importantly, however, mlo resistance can be experimentally tested as early as in five day-old seedlings and is fully functional at this time. We conclude that the Mlo protein has a negative regulatory function in plant defence and that plants with a defective protein are 'primed' for the onset of defence responses.

The deduced amino acid sequence of Mlo reveals no significant homologies to any of the described plant resistance genes so far, supporting the idea of a distinct muscular resistance mechanism. The Mlo gene shows also no striking similarities to any characterized plant or mammalian gene sequence in the various data bases. However, highly significant homologous sequences have been identified in the EST and genomic databases both from rice and *Arabidopss thaliana* (Table 5 and FIG. 5). This strongly suggests that the Mlo protein represents a member of a novel protein family. A putative nuclear localization motif (NLS) is found within exon 12 providing indication of nuclear localization of the protein (KEKKKVR; Nigg et al., 1991). The significance of this motif is supported by a casein kinase II motif located 14 amino acids into direction of the $NH_2$-terminus (SIFD; Rihs et al., 1991). Functional tests may examine the putative subcellular localization of the Mlo protein.

Mutations have been described also in other plant species in which defence responses to pathogens appear to be constitutively expressed (Walbot et al., 1983; Pryor, 1987; Jones, 1994). It has been suggested that this class of mutants, termed lesion mimics (Les) or necrotic mutants (nec), affect the control of plant defence responses. Recessively inherited lesion mimic mutants have been systematically analysed in *Arabidopsis thaliana* (Greenberg and Ausubel, 1993; Dietrich et al., 1994; Greenberg et al., 1994; Weymann et al. 1995). The affected genes have been designated acd (accelerated cell death; acd1 and acd2) or lsd (lesions simulating disease resistance response; lsd1 to lsd7).

Each of the mutants exhibits, in the absence of pathogens, HR characteristics such as plant cell wall modifications and the accumulation of defence-related gene transcripts. Leaves of the acd2 mutant have been shown to accumulate high levels-of salicylic acid and of the Arabidopsis phytoalexin, camelexin (Tsuji et al., 1992). Importantly, acd and lsd mutants exhibit elevated resistance to a bacterial (*P. syringae*) and fungal (*P. parasitica*) pathogen. The lsd1 mutant is exceptional in that it confers heightened pathogen resistance at a prelesion state, in contrast to the other defective loci which exhibit elevated pathogen resistance only in the lesion-positive state. In this respect, lsd1 resembles the mlo mutants in barley. Another striking feature of lsd1 is the indeterminate spread of lesions in contrast to the other mutants where lesion growth is determinate.

Experimental Procdures

Plant Material

A compilation of the mlo mutants and their mother varieties analyzed in this study has been described by Jørgensen (1992) and by Habekuss and Hentrich (1989). Since mutant 2118 has not been assigned to an allele number so far, we designate the allele here as mlo-26, according to current numbering in the Grainoene database (gopher colon forward slash forward slash greengenes dot cit dot cornell dot edu colon 70 forward slash 77 forward slash dot graingenes dot ndx forward slash index question mark mlo).

The high resolution map is based on a cross between Ingrid Mlo x $BC_7$ Ingrid mlo-3. $F_1$ plants were selfed generating a segregating $F_2$ population of approximately 600 plants. Phenotypically susceptible $F_2$ plants which showed heterozygosity for RFLP markers on opposite sites of Mlo were selfed and generated further segregants in the $F_3$ generation for high resolution mapping.

Powdery Mildew Infection Tests

The fungal isolate K1 (Hinze et al., 1991) is virulent on all cultivars used in this study carrying the Mlo allele and avirulent on all tested mlo genotypes. Plant growth and inoculation with *Erysiphe graminis* f sp *hordei* were carried out as described previously (Freialdenhoven et al., 1996). The genotype at Mlo of recombinants used for the high resolution map were determined after selfing and subsequent inoculation experiments in $F_3$ or $F_4$ families comprising at least 24 individuals.

AFLP Analysis

Genomic DNA for AFLP analysis was isolated according to Stewart and Via (1993). AFLP analysis was carried out with minor modifications as described by Vos et al. (1995). For screening of AFLP markers linked to Mlo we used the enzyme combinations Pst I/Mse I with amplification primers carrying +2 and +3 selective bases respectively in genomic sequences of amplified fragments. For Eco RI/Mse I amplification primers we used +3 and +3 selective bases respectively. A set of four DNA templates has been used: from the susceptible parent cultivar Ingrid Mlo, the resistant parert $BC_7$Ingrid mlo-3, a pool of two resistant $F_2$ individuals (mlo-3 mlo-3) and a pool of nine susceptible $F_2$ individuals (Mlo Mlo) derived from the cross Ingrid Mlo x $BC_7$ Ingrid mlo-3. Amplified genomic fragments representing AFLP markers Bpm2, Bpm9, and Bpm16 (FIG. 1) were cloned and sequenced as follows: gel pieces (fixed by vacuum drying to Whatman 3MM paper) containing the amplified genomic fragments were identified via autoradiography and subsequently excised. 100 $\mu$l water were added, boiled for 10 min. and after centrifugation 5 $\mu$l of the supernatant were used as a template for non-radioactive reamplification (30 cycles) with the selective AFLP primers. Amplification products were isolated after agarose gel using a DNA isolation kit (Jetsorb, Genomed Inc., USA). DNA was reated with Klenow polymerase and T4 polynucleotide kinase and subsequently cloned in the EcoRV site of pBluescript SK (Stratagene). Sequencing reactions were performed using a dye terminator cycle sequencing reaction kit (Perkin Elmer) and resolved either on an ABI 373 or 377 (Applied Biosystems) automated sequencer.

Barley YAC Library and BAC Sublibrary Construction of YAC YHV303-A6

The YAC library of barley cultivar Ingrid was. established using the pYAC4 vector (Burke et al., 1987; Kuhn and Ludwig 1994) and yeast strain AB 1380. Details of the library construction and its characterization will be described elsewhere. Screening for YAC clones containing marker Bpm16 was done by AFLP analysis. For construction of a BAC sublibrary of YAC YHV303-A6, total DNA of this yeast clone was used. After partial Eco RI digestion and preparative pulsed-field gel electrophoresis, DNA fragments in the size range of 50 kb were recovered and subcloned in the pECSBAC4 vector. Clones carrying YHV303-Ag derived inserts were identified by a two-step colony hybridization procedure. First total labelled DNA of the non-recombinant yeast strain AB 1380 was used as a probe to eliminate most of the clones carrying insert DNA derived from the host strain. In a subsequent hybridization step the remaining clones were probed wish the labelled recombinant chromosome YHV303-A6 after enrichment by preparative pulsed-field gel electrophoresis.

DNA Sequencing of BAC F15

DNA of BAC F15 was isolated by an alkaline lysis large scale plasmid preparation according to Sambrook et al. (1989). 50 Ag of purified DNA were rebulized by high pressure treatment with argon gas in a reaction chamber for 150 seconds. The ends of the sheared and reprecipitared DNA were blunt-ended by a T4 DNA polymerase-mediated fill in reaction. DNA fragments in the size range between 800 bp and 3 kb were isolated from agarose gels using a DNA isolation kit (Jetsbrb, Genomed Inc., U.S.A.), subcloned into the pBluescript SK vector (Stratagene) and propagated in *E. coli* DN5α. Clones carrying BAC F15 derived. inserts were selected by hybridization using the sheared DNA of BAC F15 as a probe. Sequencing reactions were performed as described above. Evaluation of the sequencing data, construction of sequence contigs, and estimation of coding propabilities were done by means of the STADEN software package for Unix users (4th edition, 1994). Assessment of coding probabilities was based on a combined evaluation of uneven positional base frequencies, positional base preference and barley codon usage in the investigated contigs. Homology searches were done using the BLAST software.

PCR-based Sequencing of Alleles at Mlo

Plant chromosomal DNA for this purpose was isolated according to Chunwongse et al. (1993). DNA sequences of Mlo alleles of the different barley varieties, mlo mutants, BC lines, and intragenic recombinants used in this study were obtained by PCR-based sequencing. Seven overlapping subfragments of the gene (each 400 bp–600 bp in length) were amplified by PCR (35 cycles, 60° C. annealing temperature) using sets of specific primers. After preparative agarose gel electrophoresis and isolation of the amplification products using the Jetsorb kit (Genomed Inc., U.S.A.) fragments were reamplified to increase specificity. The resulting products were subsequently purified from nucleotides and oligonucleotides (Jetpure, Genomed Inc., U.S.A.) and used as a template in DNA sequencing reactions (see above). All DNA sequences of mutnt alleles and corresponding regions of the parental lines and the intragenic recombinants were derived from both strands andconfirmedtwo times in independent sets of experiments. In addition, mutant alleles mlo-1, mlo-3, mlo-4, mlo-5, mlo-7, mlo-8, mlo-9, and mlo-10 were also verified in the corresponding BC lines in cultivar Ingrid.

RT-PCR and Rapid Amplification of cDNA Ends (RACE)

RT-PCR was performed using the SUPERSCRIPT preamplification system for first strand CDNA synthesis (Gibco BRL). Total RNA (1 $\mu$g) of seven-day-old primary barley leaves (cultivar Ingrid) served as template. First strand cDNA synthesis was primed by an oligo(dT) primer. The putative coding region of the Mlo gene was subsequently amplified using oligonucleotides 25L (GTGCATCTGCOTGTGCGTA) (SEQ ID NOs:72) and 38 (CAGAAACTTGTCTCATCCCTG) (SEQ ID NO:73) in a single amplification step (35 cycles, 60° C. annealing temperature). The resulting product was analyzed by direct sequencing 5'- and 3'-ends of the Mlo cDNA were determined by RACE (Frohman et al., 1988) using the MARATHON cDNA amplification kit (Clontech). Corresponding experimental procedures were mainly carried out according to the instructions of the manufacturer. To obtain specific RACE products, two consecutive rounds of amplification (35 cycles, 55° C. annealing temperature) were necessary. For this purpose, two sets of nested primers were used in. combination with the adapter primers of the kit: oligonucleotides 46 (AGGGTCAGGATCGCCAC) (SEQ ID NO:74) and 55 (TTGTGGAGGCCGT(TTCC) (SEQ ID NO:75) for the 51'-end and primers 33 (TGCAGCTATATGACCTTCCCCCTC) (SEQ ID NO:76) and 37 (GGACATGCTCATGGCTCAGA) (SEQ ID NO:77) for the 3'-end. RACE products were subcloned into pBluescript SK (Stratagene). Ten 5'-end and eight 3' end clones were chosen for DNA sequence analysis.

The term "AFLPs" is used herein to refer to "AFLP markers".

Table 1 summarizes the identified mutation sites of various mutants within the Mlo gene. The origin, the mutagen and the predicted effect of tre mutation at the amino acid level are indicated.

41531 *Arabidopsis thaliana* cDNA clone 97N8T7, NCBI Seq ID 932185), number T22146 (definition 4153 *Arabidopsis thaliana* cDNA clone 97N9T7, NCBI Seq ID 932186), number N37544 (definition 18771 *Arabidopsis thaliana* cDNA clone 205N12T7, NCSI Seq ID 1158686), number T88073 (definition 11769 *Arabidopsis thaliana* CDNA clone 155123T7, NCBI Seq ID 935932) number H76041 (definition 17746 *Arabidopsis thaliana* cDNM clone 193P6T7, NCRI seq ID 1053292), number D24287 (rice cDNA partial sequence R1638_1A, nID g428139) and D24131 (rice cDNA partial sequence R1408_1A, nID g427985) are shown. The Arabidbpsis sequences are from. Newman et al. (1994) *Plant Phyiol.* 106 1241–55. The rice sequences are from Minobe, Y. and Sasaki, T. submitted Nov. 2, 1993 to DDBJ.

TABLE 1 mlo Mutant Alleles

| Allele | Mother Variety | Mutagen | Mutational Event at Mlo | Effect on Amino Acid Level |
|---|---|---|---|---|
| mlo-1 | Haisa | X-rays | $T^{484} \rightarrow A$ | $trp^{182} \rightarrow arg$ |
| mlo-3 | Malleria Heda | γ-rays | deletion of 2 nucleotides (1188–1189) | frame shift after $phe^{395}$ |
| mlo-4 | Foma | X-rays | deletion of 11 nucleotides (478–488) | frame shift after $trp^{159}$ |
| mlo-5 | Carlsberg II | EMS | $G^3 \rightarrow A$ | $met^1 \rightarrow ile^a$ |
| mlo-7 | Carlsberg II | EMS | $G^{677} \rightarrow A$ | $gly^{228} \rightarrow asp$ |
| mlo-8 | Carlsberg II | EMS | $A^1 \rightarrow G$ | $met^1 \rightarrow val^a$ |
| mlo-9 | Diamant | EMS | $C^{28} \rightarrow T$ | $arg^{10} \rightarrow trp$ |
| mlo-10 | Foma | γ-rays | deletion of 6 nucleotides (543–548) | 2 amino acids ($phe^{182}$, $thr^{183}$) missing |
| mlo-12 | Elgina | NMU | $C^{720} \rightarrow A$ | $phe^{240} \rightarrow leu$ |
| mlo-13 | Plena | EMS | $T^{89} \rightarrow A$ | $val^{30} \rightarrow glu$ |
| mlo-16 | Alsa | EMS | $G^{1917*} \rightarrow A$ | alteration in 3' splice border of intron 9 |
| mlo-17 | Plena | EMS | $C^{82} \rightarrow T$ | $ser^{31} \rightarrow phe$ |
| mlo-26 | Plena | EMS | $T^{809} \rightarrow A$ | $leu^{270} \rightarrow his$ |
| mlo-28 | Nadja | $NaN_3$ | $C^{865} \rightarrow T$ | $thr^{222} \rightarrow ile$ |

Numbers of nucleotides and amino acids are given according to the translational start site of the Mlo cDNA sequence.
*Nucleotide number according to the translational start site of the genomic Mlo DNA sequence.
EMS = ethylmethane sulfonate,
NMU = nitrosomethylurea,
$NaN_3$ = sodium azide.
[a]Next start codon is at nucleotide positions 79–81 and is in frame with the coding sequence.

Table 2 shows the results of heteroallelic mlo crosses and selfings of the respective mlo lines to isolate intragenic recombination events.

Table 3 summarizes the genotypes at flanking RFLP markers in susceptible $F_2$ or homozygous $F_3$ progeny from the intermutant crosses. CO and NCO indicate crossover type and non crossover type recombinants deduced from flanking molecular marker exchange. Table 3 summarizes DNA sequence analysts of suceptible intragenic crossover type recombinants (from homozygous susceptible $F_3$ progeny) and the corresponding parental mao mutant lines. Sequences flanking the identified mutation sites are shown.

Table 4 shows the results of direct PCR seauencing of genomic DNA of susceptible intragenic recombinants derived from both heteroallelic crosses mlo-1 x mlo-8 and mlo-1 x mlo-5, revealing restoration of wild type sequences.

Table 5 shows several *Arabidopsis thaliana* and two rice expressed sequence tags (ESTs) with homology to the Mlo protein.

Table 5A show amino acid sequences, with "cuery" indicating part of the Mlo protein sequence to which homology has been found, with the predicted amino acid sequence of each identified EST marked with "subject" (SEQ ID NOs:20–49).

Table 5B shows EST nucleotide sequences encoding the amino acid sequences shown in Table 5A (SEQ ID NOs:50–56). Geniank Accession number T22145 (definition

TABLE 2

$F_2$ progeny from intermutant crosses and selfings

| Testcrosses | resistant | susceptible | frequency of susceptible $F_2$ progeny |
|---|---|---|---|
| mlo-8 × mlo-1 | 5,281 | 3 | $5.7 \times 10^{-4}$ |
| mlo-5 × mlo-1 | 915 | 0 | — |
| mlo-5 × mlo-1 | 14,474 | 9 | $6.2 \times 10^{-4}$ |

| selfings | resistant | susceptible |
|---|---|---|
| mlo-1 | 12,634 | 0 |
| mlo-5 | 5,498 | 0 |
| mlo-8 | 8,435 | 0 |

TABLE 3

Genotypes at Flanking RFLP Markers in Susceptible Progeny Derived from Heteroallelic mlo Crosses

| Testcross | Susceptible Plant | Parental Genotype In Centromeric Orientation to Mlo[1] | Parental Genotype In Telomeric Orientation to Mlo[2] | Type of Recombination |
|---|---|---|---|---|
| mlo-8 × mlo-1 | 1 | mlo-1 | mlo-8 | CO |
| | 2 | mlo-1 | mlo-8 | CO |
| | 3 | mlo-8 | mlo-8 | NCO |
| mlo-1 × mlo-5 | 1 | mlo-1 | mlo-5 | CO |
| | 2 | mlo-1 | mlo-5 | CO |
| | 3 | mlo-5 | mlo-5 | NCO |
| | 4 | mlo-1 | mlo-5 | CO |
| | 5 | mlo-5 | mlo-5 | NCO |
| | 6 | mlo-5 | mlo-5 | NCO |
| | 7 | mlo-1 | mlo-5 | CO |
| | 8* | mlo-5 | mlo-5 | NCO |
| | 9* | mlo-1 + mlo-5 | mlo-5 | CO |

[1]deduced from alleles of RFLP marker WG114 (see FIG. 1)
[2]deduced from alleles of RFLP marker ABG366 (see FIG. 1)
CO = cross over type,
NCO = non cross over type of recombination
*Genotypes of flanking RFLP markers have been determined in heterozygous susceptible $F_2$ individuals; in all other cases homozygous susceptible $F_3$ progeny derived from the susceptible $F_2$ individuals were tested

TABLE 4

Restoration of Mlo Wild Type Sequences by Intragenic Recombinantion Events

| | | | Nucleotide Sequences Flanking Mutant Sites[1] | |
|---|---|---|---|---|
| | Genotypes | | Nucleotides −3 to +3 | Nucleotides 481 to 486 |
| Haisa | Mlo | | CCGATG | AATGGG |
| | mlo-1 | | CCGATG | AAAGGG |
| Carlsberg II | Mlo | | CCGATG | AATGGG |
| | mlo-5 | | CCGATA | AATGGG |
| | mlo-8 | | CCGGTG | AATGGG |
| Intragenic recombinant | mlo-1 × mlo-8 | 1 | CCGATG | AATGGG |
| | | 2 | CCGATG | AATGGG |
| | mlo-1 × mlo-5 | 1 | CCGATG | AATGGG |
| | | 2 | CCGATG | AATGGG |
| | | 4 | CCGATG | AATGGG |
| | | 7 | CCGATG | AATGGG |
| | | 9 | CCGATG | AATGGG |

[1]Numbers of nucleotides are given according to the translational start site (see FIG. 2)

TABLE 5A

```
>EM EST1:AT1452 T22145 4153 Arabidopsis thaliana cDNA clone 97N8T7. 11/95
 Length = 382
 Plus Strand HSPs:
 Score = 248 (115.9 bits), Expect = 2.9e-27, P = 2.9e-27
 Identities = 47/100 (47%), Positives = 67/100 (67%), Frame = +2

Query: 242 KYIKRSMEDDFKVVVGISLPLWGVAILTLFLDINGVGTLIWISFIPLVILLCVGTKLEMI  301
           KY+ R++EDDFK VVGIS  LW   ++   L++NG  T  WI+FIP  +LL VGTKLE +
Sbjct:   2 KYMMRALEDDFKQVVGISWYLWXFVVIFXLLNVNGWHTYFWIAFIPPXLLLAVGTKLEHV  181

Query: 302 IMEMALEIQDRASVIKGAPVVEPSNKFFWFHRPDWVLFFI 341
           I ++A E+ ++   I+G  VV+P  + FWF +P  VL+ I
Sbjct: 182 IAQLAHEVAEKHVAIEGDLVVKPXXEHFWFSKPQIVLYLI 301

>EM EST1:AT1462 T22146 4154 Arabidopsis thaliana cDNA clone 97N9T7. 11/95
 Length = 390
 Plus Strand HSPs:
 Score = 212 (99.1 bits), Expect = 4.2e-26, Sum P(2) = 4.2e-26
 Identities = 41/83 (49%), Positives = 58/83 (69%), Frame = +2

Query: 242 KYIKRSMEDDFKVVVGISLPLWGVAILTLFLDINGVGTLIWISFIPLVILLGVGTKLEMI  301
           KY+ R++EDDFK VVGIS  LW   ++ L L++NG  T  WI+FIP  +LL VGTKLE +
Sbjct:   2 KYMMRALEDDFKQVVGISWYLWXFVVIFLLLNVNGWHTYFWIAFIPFALLLAVGTKLEHV  181

Query: 302 IMEMALEIQDRASVIKGAPVVEP 324
           I ++A E+ ++   I+G  VV+P
```

TABLE 5A-continued

```
Sbjct: 182 IAQLAHEVAEKHVAIEGDLVVKP 250

 Score = 52 (24.3 bits), Expect = 1.9, Sum P(2) = 0.85
 Identities = 9/32 (28%), Positives = 16/32 (50%), Frame = +2

Query:  18 WAVAVVFAAMVLVSVLMEHGLHKLGHWFQHRH 49
           W   + FA ++ V   +EH + +L H    +H
Sbjct: 122 WIAFIPFALLLAVGTKLEHVIAQLAHEVAEKH 217

 Score = 49 (22.9 bits), Expect = 4.2e-26, Sum P(2) = 4.2e-26
 Identities = 8/17 (47%), Positives = 12/17 (70%), Frame = +1

Query: 323 EPSNKFFWFHRPDWVLF 339
           E S++ EWF +P  VL+
Sbjct: 244 ETSDEHFWFSKPQXVLY 294

>EM EST1:AT54418 N37544 18771 Arabidopsis thaliana cDNA clone 205N12T7. 1/96
 Length = 585
 Plus Strand HSPs:
 Score = 277 (129.5 bits), Expect = 1.2e-45, Sum P(2) = 1.2e-45
 Identities = 51/96 (53%), Positives = 71/96 (73%), Frame = +1

Query: 236 SKFDFHKYIKRSMEDDFKVVVGISLPLWGVAILTLFLDINGVGTLIWISFIPLVILLCVG   295
           S+FDF KYI+RS+E DFK VV.IS  +W VA+L L  +  G+ + +W+ FIPLV++L VG
Sbjct: 127 SRFDFRKYIQRSLEKDFKTVVEISPVIWFVAVLFLLTNSYGLRSYLWLPFIPLVVILIVG   306

Query: 296 TKLEHIIMEMALEIQDRASVIKGAPVVEPSNKFFWF 331
           TKLE+II ++ L IQ+   V++HAPVV+P +  FWF
Sbjct: 307 TKLEVIITKLGLRIQEEGDVVRGAPVVQPGDDXFWF 414

 Score = 121 (56.6 bits), Expect = 1.2e-45, Sum P(2) = 1.2e-45
 Identities = 25/45 (55%), Positives = 29/45 (64%), Frame = +1

Query: 196 SSTPGIRWVVAFFRQFFRSVTKVDYLTLRAGFINAHLSQNSKFDF 240
           S T    W+V FFRQFF SVTRVDYL L  GFI AH +  ++  F
Sbjct:   1 SKTRVTLWIVCFFRQFFGSVTKVDYLALXHGFIMAHFAPGNESRF 135

>EM EST1:AT04117 H76041 17746 Arabidopsis thaliana cDNA clone 193P6T7. 11/95
 Length = 476
 Plus Strand HSPs:
 Score = 210 (98.2 bits), Expect = 9.0e-36, Sum P(2) = 9.0e-36
Identities = 43/86 (50%), Positives = 58/86 (67%), Frame = +1

Query: 196 SSTPGIRWVVAFFRQFFRSVTKVDYLTLRAGFINAHLSQNSKFDFHKYIKRSMEDDFKVV   255
           ++TP    V  FFRQFF SV + DYLTLR GF +AHL+   KF+F +YIK S+EDDFK+V
Sbjct: 124 TTTPFXFNVGCFFRQFFVSVERTDYLTLRHGFXSAHLAPGRKFNFQRYIKXSLEDDFKLV   303

Query: 256 VGISLPLWGVAILTLFLDINGVGTLI 281
           VGI   LW   ++ L +    +GT++
Sbjct: 304 VGIXPVLWASFVIFLAVQX*WLGTIV 381

 Score = 119 (55.6 bits), Expect = 9.0e-36, Sum P(2) = 9.0e-36
 Identities = 24/57 (42%), Positives = 32/57 (56%), Frame = +1

Query: 156 MRTWKKWETETTSLEYQFANDPARFRFTHQTSVFKRHLGLSSTPGIRWVVAFFRQFF     212
           +R WKKWE  T S +Y F  D +R R TH+TSFV+ H    +T    + V  F + F
Sbjct:   1 IRGWKKWEQXTLSNDYXFXIDHSRLRLTHETSFVREHTSFWTTTPFXFNVGCFFRQF     171

 Score = 40 (18.7 bits), Expect = 1.2e-08, Sum P(2) = 1.2e-08
 Identities = 8/19 (42%), Positives = 10/19 (52%), Frame = +2

Query: 269 TLFLDINGVGTLIWISFIP 287
           +L  + NG G L W S  P
Sbjct: 344 SLLVNXNGWGPLFWASVPP 400

>EM EST1:AT0739 T88073 11769 Arabidopsis thaliana cDNA clone 155I23T7. 11/95
 Length = 460
 Plus Strand HSPs:
 Score = 175 (81.8 bits), Expect = 1.2e-24, Sum P(2) = 1.2e-24
Identities = 31/67 (46%), Positives = 43/67 (64%), Frame = +1

Query: 146 VITIALSRLKMRTWKKWETETTSLEYQFANDPARFRFTHQTSVFKRHLGLSSTPGIRMVV   205
           ++T A  ++KMRTWK WE ET ++EYQ++NDP RFRF    TSF +RHL    S   +   +
Sbjct:   4 IVTYAFGKIKMRTWESWKEETKTIEYQYSNDPERFRFARDTSFGRRHLNFWSKTRVTLWI   183

 Score = 121 (56.6 bits), Expect = 1.4e-14, Sum P(2) = 1.4e-14
 Identities = 25/45 (55%), Positives = 29/45 (64%), Frame = +1
```

TABLE 5A-continued

```
Query: 196 SSTPGIRWVVAFFRQFFRSVTKVDYLTLRAGFINAHLSQNSKFDF 240
           S T    W+V FFRQFF SVTKVDYL L  GFI AH +  ++  F
Sbjct: 157 SKTRVTLWIVCFFRQFFGSVTKVDYLALXHGFIMAHFAPGNESRF 291

 Score = 75 (35.1 bits), Expect = 1.2e-24, Sum P(2) = 1.2e-24
 Identities = 14/21 (66%), Positives = 17/21 (80%), Frame = +1

Query: 236 SKFDFHKYIKRSMEDDFKVVV 256
           S+FDF KYI+RS+  DFK VV
Sbjct: 283 SRFDFRKYIQRSLXXDFKTVV 345

>EM EST5:OSR16381A D24287 Rice cDNA, partial sequence (R1638_1A). 5/95
 Length = 400
 Plus Strand HSPs:
 Score = 147 (88.7 bits), Expect = 1.9e-16, Sum P(2) = 1.9e-16
 Identities = 26/53 (49%), Positives = 35/53 (66%), Frame = +1

Query: 236 SKFDFHKYIKRSMEDDFKVVVGISLPLWGVAILTLFLDINGVGTLIWISFIPL         288
           ++F+F KYIKR +EDDFK VVGIS P W  A+  +  +++G   L W S  PL
Sbjct: 202 TRFNFRKYIKRXLEDDFKYVVGISAPXWASALAIMLFNVHGWHNLFWFSTXPL         360

 Score = 45 (21.0 bits), Expect = 1.9e-16, Sum P(2) = 1.9e-16
 Identities = 9/15 (60%), Positives = 11/15 (73%), Frame = +2

Query: 287 PLVILLCVGTKLEMI 301
           PL + L VGTKL+ I
Sbjct: 356 PLXVTLAVGTKLQAI 400

>EM EST5:OSS1692A D39989 Rice cDNA, partial sequence (S1692_1A). 11/94
 Length = 343
 Plus Strand HSPs:
 Score = 95 (44.4 bits), Expect = 0.00059, P = 0.00059
Identities = 24/58 (41%), Positives = 31/58 (53%), Frame = +3

Query:  43 HWFQHRHKKALWEALEKMKAELMLVGFISLLLIVTQDPIIAKICISEDAADVMWPCKR    100
           H  +  H+  L +A+EKMK E+ML+GFISLLL  T   I      S+       PC R
Sbjct:   3 HXSEKTHRNPLHKAMEKMKEEMMLLGFISLLLAATSRIISGICIDSKYYNSNFSPCTR    176
```

TABLE 5B

```
GenBank Accession Number T22145
    1 caagtatatg atgcgcgctc tagaggatga tttcaaacaa gttgttggta ttagttggta
   61 tctttggntc tttgtcgtca tctttttnct gctaaatgtt aacggatggc acacatattt
  121 ctggatagca tttattccct ttnctttgct tcttgctgtg ggaacaaagt tggagcatgt
  181 nattgcacag ttagctcatg aagttgcaga gaaacatgta gccattgaag gagacttagt
  241 ggtgaaaccc ncanatgagc atttctggtt cagcaaacct caaattgttc tctacttgat
  301 cccattttat cctctttccc agaatgcntt ttnagantgc ntttttttnnt tttggnnttt
  361 ggggtaanan annggtttcg nc

GenBank Accession Number T22146
    1 caagtatatg atgcgcgctc tagaggatga tttcaaacaa gttgttggta ttagttggta
   61 tctttggntc tttgtcgtca tctttttgct gctaaatgtt aacggatggc acacatattt
  121 ctggatagca tttattccct ttgctttgct tcttgctgtg ggaacaaagt tggagcatgt
  181 nattgcacag ttagctcatg aagttgcaga gaaacatgta gccattgaag gagacttagt
  241 ggtgaaacct cagatgagca tttctggttc agcaaacctc aaantgttct ctactngatc
  301 cnctttatcc cccttccaga atgccttttt nangattcnn ntttttcctt nttgganntt
  361 ttgggnnnnc aaacgggntt nggacctccg

GenBank Accession Number N37544
    1 agcaagacga gagtcacact atggattgtt tgttttttta gacagttctt tggatctgtc
   61 accaaagttg attacttagc actaagncat ggtttcatca tggcgcattt tgctcccggt
  121 aacgaatcaa gattcgattt ccgcaagtat attcagagat cattagagaa agacttcaaa
  181 accgttgttg aaatcagtcc ggttatctgg tttgtcgctg tgctattcct cttgaccaat
  241 tcatatggat tacgttctta cctctggtta ccattcattc cactagtcgt aattctaata
  301 gttggaacaa agcttgaagt cataataaca aaattgggtc taaggatcca agaggaaggt
  361 gatgtggtga gaggcgcccc agtggttcag cctggtgatg accncttctg gtttngnaan
  421 cacgnttcaa tnttttccnt antcacttng gcctttttan gggtgaattt caacttcatn
  481 ctttncctgg ggncggatga ttcaatccaa naatnttccc ctgaagnctn caagtttggg
  541 cataggcttt nggtgggntt ttcaganttt nagtttggct tnccc

GenBank Accession Number T88073
    1 tgcattgtta cttatgcttt cggaaagatc aagatgagga cgtggaagtc gtgggaggaa
   61 gagacaaaga caatagagta tcagtattcc aacgatcctg agaggtteag gtttgcnagg
  121 gacacatctt ttgggagaag acatctcaat ttctggagca agacgagagt cacactatgg
  181 attgtttgtt tttttagaca gttctttgga tctgtcacca aagttgatta cttagcacta
  241 agncatggtt tcatcatggc gcattttgct eccggtaacg aatcaagatt cgatttccgc
```

TABLE 5B-continued

```
 301 aagtatattc agagatcatt agngnaagac ttcaaaaccg ttgtttgaaa tcagtccggt
 361 tatctggttt gtcggctgtg ctattccnct tgaccaattc atatggntnc ggtnttncnc
 421 tggtaccatt attcnctagc ggaatntaaa agttggcnga

GenBank Accession Number H76041
   1 attcgtggat ggaaaaagtg ggagcaagan acattatcta atgactatna gtttnctatt
  61 gatcattcaa gacttaggct cactcatgag acttcttttg tnagagaaca tacaagtttc
 121 tggacaacaa cnccttctc ctttaacgtc ggatgcttct ttaggcagtt ctttgtatct
 181 gtngaaagaa ccgactactt gactctgcgc catggattca nctctgccca tttagctcca
 241 ggaagaaagt tcaacttcca gagatatatc aaangatctc tcgaggatga tttcaagttg
 301 gtagttggaa taagnccagt tctttgggca tcatttgtaa tcttccttgc tgttcaatgn
 361 taatggctgg ggaccattgt tttgggcntc ggtaccgcct ntactcanaa ncccaggctt
 421 ttggccaagg ttcaaggaat ttngggacaa tggggtagaa tcgtgggcnc atnngg

GenBank Accession Number D24287
   1 tcntntttnn ttttcgnntn cntccacccc tnnnntnctc nancncnttn nnnttatctc
  61 tnttnttntc ncntntcecn ncaccaccnn ncgacgggcn tggactnngc ccnnngttcg
 121 aggctgccca ctgncgtctg agacctacct tgncatttga cggcacngga cttcanttgc
 181 tgctcacttt atctctacgg gactaggttc aattttcgga aatacatcaa aaggncactg
 241 gaggacgatt ttaagacagt tgttggcatt agtgcacccn tatgggcttc tgcgttggcc
 301 attatgctot tcaatgttca tggatggcat aacttgttct ggttctctac aatnccctt
 361 gntagtaact ttagcagttg gaacaaagct gcaggctata

GenBank Accession Number D24131
   1 cagactacct gactttgagg cacggattca ttgctgctca tttatctcta gggactaggt
  61 tcaattttcg gaaatacatc aaaaggtcac tggaggacga ttttaagaca gttgttggca
 121 ttagtgcacc cttatgggct tctgcgttgg ccattatgct cttnaatgtt catggatggc
 181 ataacttgtt ctggttctct acaatccccc ttgtagtaac tttagcagtt ggaacaaagc
 241 tgcaggctat aattgcaatg atggctgttg aaattaaaga gaggcataca gtaattcaag
 301 gaatgccggt ggtgaactca gtgat
```

References

1. Bayles, et al. (1990). Physiol. Mol. Plant Pathol. 36, 63–72.
2. Becker, et al. (1995). Mol. and Gen. Genet. 249, 65–73.
3. Bennet, et al. (1991). Phil. Trans. R. Soc. London (Biol) 334, 309–345.
4. Bent, et al. (1994). Science 265, 1856–1860.
5. Boyd, et al. (1995). Plant. J., 7, 959–968.
6. Bourque, J. E. (1995). Plant Science 105, 125–149.
7. Burke, et al. (1987). Science 236, 806–812.
8. Cao, et al. (1992). Plant Cell Rep. 11, 58S-S91.
9. Christou, et al. (1991). Bio/Technology 9, 957–962.
10. Chunwongse, et al. (1993). Ther. Appl. Genet., 86, 694–698.
11. Civardi (1994).
12. Cornejo, et al. (1993). Plant Molecular Biology 23, 567–581.
13. Dangl, J. L. (1995). Cell 80, 363–366.
14. Dangl, J. L., et al. (1996). Plant Cell (in press).
15. Datta, et al. (,990). Bio/Technology 8, 736–740.
16. de Feyter, et al. (1996). Molecular and General Genetics 250, 329–338.
17. D'Halluin, et al. (1992). Plant Cell 4, 1495–1505.
18. Dietrich, et al. (1994). Cell 77, 565–577.
19. Doke, N. (1983). Physiol. Plant Pathol., 23, 345–357.
20. Doke, N. and Ohashi, Y. (1988). Physiol. Mol. Plant Path., 32, 163–175.
21. Dooner, H. K. and Kermicle, J. L. (1986). Genetics, 113, 135–143.
22. Dujon, B. (1996). Trends Genet., 12, 263–270.
23. Flavell, R. B. (1994). Proc. Natl. Acad. Sci. USA 91, 3490–3496.
24. Flor, H. H. (1971). Annu. Rev. Phytopathol. 9, 275–296.
25. Freeling, M. (1978). Genetics, 89, 211–224.
26. Freialdenhoven, A., et al. (1996). Plant Cell, 8, 5–14.
27. Frohman, N. A., et al. (1988). Proc. Natl. Acad. Sci., 85, 8998–9002.
28. Fromm, et al. (1990). Bio/Technology 8, 833–839.
29. Fugimoto, et al. (993). Bio/Technology 11, 1151–1155.
30. Giovannoni, J. J., et al. (1991). Nucl. Acids Res., 19, 6553–6558.
31. Gordon-Kamm, et al. (1990). Plant Cell 2, 603–618.
32. Görg, R., et al. (1993). Plant J. 3, 857–866.
33. Grant, et al. (1995). Science 269, 843–846.
34. Greenberg, et al. (1993). The Plant Journal 4, 327–341.
35. Greenberg, et al. (1994). Cell 77, 551–563.
36. Habekuss, A. and Hentrich, W. (1988). *Tag. Ber., Akad. Lanwirtsch.-Wiss. DDR*, Berlin, 272: 229–237.
37. Hammond-Kosack, K. E. and Jones, J. D. G. (1996). The Plant Cell (in press).
38. Hartmann, E., et al. (1989). Proc. Natl. Acad. Sci., 86: 5786–5790.
39. Haselhoff, et al. (1988). Nature 334, 585–491.
40. Heath, M. C. (1980). *Annu. Rev. Phytopathol.*, 18: 211–236.
41. Hentrich, W. (1979). Arch. Züchtungsvorsch., Berlin 9, S. 283–291.
42. Heslop-Harrison, J. S. (1991). J. Cell Sci., 100, 15–21.
43. Hiei, et al. (1994). The Plant Journal 6, 271–282.
44. Hieter, et al. (1990). Cold Spring Harbor, N.Y, Col Spring Harbor Press.
45. Hinze, et al. (1991). Proc. Natl. Acad. Sci. USA 88, 3691–3695.
46. Jabs, T., et al. (1996). Science, 273, 1853–55.
47. Jones, D.T., et al. (1994). Biochemistry, 33, 3038–3049.
48. Jones, et al. (1994). Science 266, 789–793.
49. Jones, J. D. G. (1994). Current Biology 4, 749–751.
50. Jørgensen, J. H. (1977) Induced mutations against plant diseases (Crop Symposium Vienna)533–547.
51. Jørgensen, J. H. (1983). Induced mutations for disease resistance in crop plants Tn (International Atomic Energy Agency, Vienna)73–87.
52. Jørgensen, J. H. (1992). Euphytica 63, 141–152
53. Jørgensen, J. H. (1994). Critical Reviews in Plant Sciences 13, 97–119.
54. Jørgensen, J. H. and Mortensen, K. (1977). Phytopathology, 67, 678–685.

55. Klein, P., et al. (1985). Biochim. Biophys. Acta, 815, 468–476.
56. Koga, H., et al. (1990). Can. J. Bat., 68, 2344–2352.
57. Koornneef, M., et al. (1983). Genet. Res. Camb., 41, 57–68.
58. Kosslak, R., et al. (1996). J. Hered (in press).
59. Kuhn, R. M. and Ludwig. R. A. (1994). Gene, 141, 125–127.
60. Künzel, G. (1982). Theor. Appl. Genet., 64, 25–29.
61. Koziel, et al. (1993). Biotechnology 11, 194–200.
62. Lamb, C. J. (1994). Cell, 76: 419–422.
63. Lawrence, et al. (1995). The Plant Cell 7, 1195–1206.
64. Levine, A., et al. (1994). Cell, 79: 583–593.
65. Li, et al. (1993). Plant Cell Rep. 12, 250–255.
66. Linde-Laursen, I., et al. (1982). Z. Pflanzenzüchtg., 81, 191–219.
67. Lundqvist, U., et al. (1991). Hereditas, 115, 227–239.
68. Martin, et al. (1993). Science 262, 1432–1436.
69. McClintock, B. (1984). Science, 226, 792–801.
70. Mindrinos, et al. (1994). Cell 78, 1089–1099.
71. Moore, et al. (1995). Current Biology 5, 737–739.
72. Mourad, G., et al. (1994). Mol. Gen. Genet., 243, 178–184.
73. Negassa, M. (1985). Hereditas, 102, 113–121.
74. Nigg, et al. (1991). Cell 66, 15–22.
75. Osborne, et al. (1995). Current Opinion in Cell Biology 7, 406–413.
76. Olsen, O., et al. (1993). Proc. Natl. Acad. Sci. USA, 90, 8043–8047.
77. Peng, et al. (1992). Theor Appl Genet 83, 855–863.
78. Peng, et al. (1991). International Rice Research Institute, Manila, Philippines.563–574.
79. Pryor, A. J. (1987). Trends in Genetics 39 157–161.
80. Raff, M. C. (1992). Nature, 356, 397–400.
81. Raff, M. C., et al. (1993). Science, 262, 695–700.
82. Rathore, et al. (1993). Plant Molecular Biology 21, 871–5 884.
83. Rihs, et al. (1991). EMBO J. 10, 633–639.
84. Ryerson, D. E. and Heath, M. C. (1996). Plant Cell, 8, 393–402.
85. Salamini, F., and Lorenzoni, C. (1970). Mol. Gen. Genet., 108, 225–232.
86. Sambrook, J., et al. (1989). Cold Spring Harbor Laboratory Press, New York.
87. Schmidt, R., et al. (1995). Science, 270, 480–483.
88. Sherman, et al. (1986). Cold Spring Harbor, N.Y., Cold Spring Harbor Laboratory Press.
89. Shimamoto, K. 1934). Current Opinion in Biotechnology 5, 158–162.
90. Shimamoto, et al. (1989). Nature 338, 274–276.
91. Shirley, B. W., et al. (1992). Plant Cell, 4, 333–347.
92. Shizuya, et al. (1992). Proc. Natl. Acad. Sci. USA 89, 8794–8797.
93. Siedler, et al. (1991). Molecular and General Genetics 226, 117–181.
94. Sogaard, et al. (1988). Barley Genet. Newslett. 17, 120–134.
95. Somers, et al. (1992). Bio/Technology 10, 1589–1594.
96. Song, et al. (1995). Science 270, 1804–1806.
97. Stakman, E. C. (1915). *J. Ag. Research*, 4: 193–199.
98. Staskawicz, et al. (1995). Science 268, 661–667.
99. Stewart, C. N. and Via, L. E. (1993). *BioTechniques*, 14: 748–750.
100. Szostak, J. W., et al. (1983). *Cell*, 33: 25–35.
101. Tanksley, et al. (1995). Trends in Genetics 11, 63–68.
102. Thomas, C. M., et al. (1995). *Plant J.*, 8: 785–794.
103. Toriyama, et al. (1988). Bio/Technology 6, 1072–1074.
104. Tsuji, et al. (1992). Plant Physiology 98, 1304–1309.
105. Vasil, I. K. (1994). Plant Molecular Biology 25, 925–937.
106. Vasil, et al. (1992). Bio/Technology 10, 667–674.
107. Vos, et al. (1995). Nucleic Acids Research 23, 4407–4414.
108. Walbot, et al. (1983). New York, Plenum Press 431–442.
109. Walters, et al. (1992). Plant Molecular Biology 18, 189–200.
110. Wang, et al. (1995). Plant Journal 7, 525–533.
111. Weeks, et al. (1993). *lant Physiology* 102, 1077–1084:
112. Weymann, et al. (1995). The Plant Cell 7, 2013–2022.
113. White, E. (1996). *Genes & Development*, 10: 1–15.
114. Whitham, et al. (1994). Cell 78, 1011–1115.
115. Wiberg, A. (1974). Hereditas 77, 89–148.
116. Wolter, et al. (1993). Mol. Gen. Genet. 239, 122–128.
117. Wyllie, A.H. (1995). *Current Biology*, 5: 97–104.
118. Zhang, et al. (1988). Plant Cell Rep. 7, 379–384.
119. Zhang, et al. (1991). Plant Cell 3, 1155–1165.
120. Zhang, et al. (1988). Theor Appl Genet 76, 835–840.

What is claimed is:

1. An isolated polynucleotide encoding a polypeptide which comprises the amino acid sequence of SEQ ID NO:1.

2. The isolated polynucleotide according to claim 1, wherein the polynucleotide comprises the nucleotide sequence of SEQ ID NO:2.

3. The isolated polynucleotide according to claim 1 operably linked to a regulatory sequence for expression.

4. An isolated polynucleotide comprising of a nucleotide sequence selected from the group consisting of:

a) the nucleotide sequence encoding SEQ ID NO:2;

b) a nuleotide sequence having at least 95% sequence identity to SEQ ID NO:1, wherein the nucleotide sequence encodes a polypeptide having disease resistance activity;

c) a polynucleotide encoding a poypeptide having at least 95% seguences identity to SEQ ID NO:2, wherein the polypeptide has disease resistance activity; and d) a complement of (a), (b) or (c).

5. The isolated polynucleotide according to claim 4 operably linked to a regulatory sequence for transcription.

6. The isolated polynucleotide according to claim 3 wherein the regulatory sequence comprises an inducible promoter.

7. A plant expressible vector comprising a polynucleotide according to claim 1.

8. A plant cell containing the polynucleotide according to claim 1, wherein said polynucleotide is heterologous.

9. A plant or plant part, which plant or plant part comprises a plate cell containing the polynucleotide according to claim 1, wherein said polynucleotide is heterologous.

* * * * *

SEQUENCE LISTING

```
<160> NUMBER OF SEQ ID NOS: 79

<210> SEQ ID NO 1
<211> LENGTH: 533
<212> TYPE: PRT
<213> ORGANISM: Hordeum vulgare

<400> SEQUENCE: 1

Met Ser Asp Lys Lys Gly Val Pro Ala Arg Glu Leu Pro Glu Thr Pro
  1               5                  10                  15

Ser Trp Ala Val Ala Val Val Phe Ala Ala Met Val Leu Val Ser Val
             20                  25                  30

Leu Met Glu His Gly Leu His Lys Leu Gly His Trp Phe Gln His Arg
         35                  40                  45

His Lys Lys Ala Leu Trp Glu Ala Leu Glu Lys Met Lys Ala Glu Leu
     50                  55                  60
```

-continued

```
Met Leu Val Gly Phe Ile Ser Leu Leu Leu Ile Val Thr Gln Asp Pro
 65                  70                  75                  80

Ile Ile Ala Lys Ile Cys Ile Ser Glu Asp Ala Ala Asp Val Met Trp
                 85                  90                  95

Pro Cys Lys Arg Gly Thr Glu Gly Arg Lys Pro Ser Lys Tyr Val Asp
            100                 105                 110

Tyr Cys Pro Glu Gly Lys Val Ala Leu Met Ser Thr Gly Ser Leu His
        115                 120                 125

Gln Leu His Val Phe Ile Phe Val Leu Ala Val Phe His Val Thr Tyr
    130                 135                 140

Ser Val Ile Thr Ile Ala Leu Ser Arg Leu Lys Met Arg Thr Trp Lys
145                 150                 155                 160

Lys Trp Glu Thr Glu Thr Thr Ser Leu Glu Tyr Gln Phe Ala Asn Asp
                165                 170                 175

Pro Ala Arg Phe Arg Phe Thr His Gln Thr Ser Phe Val Lys Arg His
            180                 185                 190

Leu Gly Leu Ser Ser Thr Pro Gly Ile Arg Trp Val Val Ala Phe Phe
        195                 200                 205

Arg Gln Phe Phe Arg Ser Val Thr Lys Val Asp Tyr Leu Thr Leu Arg
    210                 215                 220

Ala Gly Phe Ile Asn Ala His Leu Ser Gln Asn Ser Lys Phe Asp Phe
225                 230                 235                 240

His Lys Tyr Ile Lys Arg Ser Met Glu Asp Asp Phe Lys Val Val Val
                245                 250                 255

Gly Ile Ser Leu Pro Leu Trp Gly Val Ala Ile Leu Thr Leu Phe Leu
            260                 265                 270

Asp Ile Asn Gly Val Gly Thr Leu Ile Trp Ile Ser Phe Ile Pro Leu
        275                 280                 285

Val Ile Leu Leu Cys Val Gly Thr Lys Leu Glu Met Ile Ile Met Glu
    290                 295                 300

Met Ala Leu Glu Ile Gln Asp Arg Ala Ser Val Ile Lys Gly Ala Pro
305                 310                 315                 320

Val Val Glu Pro Ser Asn Lys Phe Phe Trp Phe His Arg Pro Asp Trp
                325                 330                 335

Val Leu Phe Phe Ile His Leu Thr Leu Phe Gln Asn Ala Phe Gln Met
            340                 345                 350

Ala His Phe Val Trp Thr Val Ala Thr Pro Gly Leu Lys Lys Cys Tyr
        355                 360                 365

His Thr Gln Ile Gly Leu Ser Ile Met Lys Val Val Val Gly Leu Ala
    370                 375                 380

Leu Gln Phe Leu Cys Ser Tyr Met Thr Phe Pro Leu Tyr Ala Leu Val
385                 390                 395                 400

Thr Gln Met Gly Ser Asn Met Lys Arg Ser Ile Phe Asp Glu Gln Thr
                405                 410                 415

Ser Lys Ala Leu Thr Asn Trp Arg Asn Thr Ala Lys Glu Lys Lys Lys
            420                 425                 430

Val Arg Asp Thr Asp Met Leu Met Ala Gln Met Ile Gly Asp Ala Thr
        435                 440                 445

Pro Ser Arg Gly Ser Ser Pro Met Pro Ser Arg Gly Ser Ser Pro Val
    450                 455                 460

His Leu Leu His Lys Gly Met Gly Arg Ser Asp Asp Pro Gln Ser Ala
465                 470                 475                 480
```

-continued

```
Pro Thr Ser Pro Arg Thr Gln Gln Glu Ala Arg Asp Met Tyr Pro Val
                485                 490                 495

Val Val Ala His Pro Val His Arg Leu Asn Pro Asn Asp Arg Arg Arg
            500                 505                 510

Ser Ala Ser Ser Ser Ala Leu Glu Ala Asp Ile Pro Ser Ala Asp Phe
        515                 520                 525

Ser Phe Ser Gln Gly
    530
```

<210> SEQ ID NO 2
<211> LENGTH: 1602
<212> TYPE: DNA
<213> ORGANISM: Hordeum vulgare

<400> SEQUENCE: 2

```
atgtcggaca aaaaaggggt gccggcgcgg gagctgccgg agacgccgtc gtgggcggtg     60

gcggtggtct tcgccgccat ggtgctcgtg tccgtcctca tggaacacgg cctccacaag    120

ctcggccatt ggttccagca ccggcacaag aaggccctgt gggaggcgct ggagaagatg    180

aaggcggagc tcatgctggt gggcttcata tccctgctcc tcatcgtcac gcaggacccc    240

atcatcgcca agatatgcat ctccgaggat gccgccgacg tcatgtggcc ctgcaagcgc    300

ggcaccgagg gccgcaagcc cagcaagtac gttgactact gcccggaggg caaggtggcg    360

ctcatgtcca cgggcagctt gcaccagctg cacgtcttca tcttcgtgct cgcggtcttc    420

catgtcacct acagcgtcat caccatagct ctaagccgtc tcaaaatgag aacatggaag    480

aaatgggaga cagagaccac ctccttggaa taccagttcg caaatgatcc tgcacggttc    540

cggttcacgc accagacgtc gttcgtgaag cgccacctgg gcctctccag cacccctggc    600

atcagatggg tggtggcctt cttcaggcag ttcttcaggt cagtcaccaa ggtggactac    660

ctgaccttga gggcaggctt catcaacgcg catttgtcgc aaaacagcaa gttcgacttc    720

cacaagtaca tcaagaggtc gatggaggac gacttcaagg tcgtcgtcgg catcagcctc    780

ccgctgtggg gtgtggcgat cctcaccctc ttccttgaca tcaatggggt tggcacgctc    840

atctggattt ctttcatccc tctcgtgatc ctcttgtgtg ttggaaccaa gctggagatg    900

atcatcatgg agatggccct ggagatccag gaccgggcga gcgtcatcaa gggggccccc    960

gtggtcgagc ccagcaacaa gttcttctgg ttccaccgcc ccgactgggt cctcttcttc   1020

atacacctga cgttgttcca gaacgcgttt cagatggcgc attttgtgtg gacagtggcc   1080

acgcccggct tgaagaaatg ctaccacacg cagatcgggc tgagcatcat gaaggtggtg   1140

gtggggctag ctctccagtt cctctgcagc tatatgacct tcccccctcta cgcgctcgtc  1200

acacagatgg gatcaaacat gaagaggtcc atcttcgacg agcagacgtc caaggcgctc   1260

accaactggc ggaacacggc caaggagaag aagaaagtcc gagacacgga catgctgatg   1320

gctcagatga tcggcgacgc aacaccgagc cgaggctcgt cgccgatgcc gagccggggc   1380

tcatcacccg tgcacctgct tcacaagggc atggggcggt cggacgaccc ccagagcgcg   1440

cccacctcgc caaggaccca gcaggaggct agggacatgt acccggttgt ggtggcgcac   1500

ccggtgcaca gactaaatcc taacgacagg aggaggtccg cctcgtcgtc ggccctcgaa   1560

gccgacatcc ccagtgcaga tttttccttc agccagggat ga                      1602
```

<210> SEQ ID NO 3
<211> LENGTH: 2098
<212> TYPE: DNA
<213> ORGANISM: Hordeum vulgare -continued

<400> SEQUENCE: 3

```
gcggagctca tgctggtggg cttcatatcc ctgctcctca tcgtcacgca ggaccccatc     60
atcgccaaga tatgcatctc cgaggatgcc gccgacgtca tgtggccctg caagcgcggc    120
accgagggcc gcaagcccag caagtacgtt gactactgcc cggaggtgag cagcagagcc    180
cggaccagca gcttcacgat gatgaagaaa tcaataccga actttttctt gttttcttct    240
gattgtcgtc ttggcttggc ttaattggtg tgtgtgtgtg tgtttgcagg gcaaggtggc    300
gctcatgtcc acgggcagct tgcaccagct gcacgtcttc atcttcgtgc tcgcggtctt    360
ccatgtcacc tacagcgtca tcaccatagc tctaagccgt ctcaaagtga gcctttgctt    420
cttcttcttc ttcttttacc gcacgtctgt ctgtcaggcg tacctacctg ttcatcaggc    480
ttgagtaaaa ctgttccata atctgctccg gcataatcct ctcctcctgc agatgagaac    540
atggaagaaa tgggagacag agaccacctc cttggaatac cagttcgcaa atggtcagga    600
tcccccactc tgcaatctcc ccttcttcga aaccaaacct gatgatccat ttaaagacgc    660
aggcacgatc agagtgagtg aactgatgta tgttcatttt ttgtgtcctt tcagatcctg    720
cacggttccg gttcacgcac cagacgtcgt tcgtgaagcg ccacctgggc ctctccagca    780
cccctggcat cagatgggtg gtgagttttt tagcttctta tctgcccctc atctgtgtgt    840
aatgtttggc gtatggagtc aggtgattta ccttgcctgt gatgtttgtt gccttgtcag    900
gtggccttct tcaggcagtt cttcaggtca gtcaccaagg tggactacct gaccttgagg    960
gcaggcttca tcaacgtacg tgcctcccct tctagctccg ccattgctgc cgcgatgtag   1020
cagcaaagct tctcaagtta tccttctgac gctaaagttc ccatgttttt tcctcaaatt   1080
attctgcgca ggcgcatttg tcgcaaaaca gcaagttcga cttccacaag tacatcaaga   1140
ggtcgatgga ggacgacttc aaggtcgtcg tcggcatcag gtacgttcca ttccttcctc   1200
tgcaccacac cacaccccat ggatagattt taacaattgc tgtcaggttc cacatgataa   1260
caatatacta tgaacttggt ctttgctcct tgtccttgca cgatcatgac acatttggcc   1320
tgttttcgca gcctcccgct gtggggtgtg gcgatcctca ccctcttcct tgacatcaat   1380
ggtatggacc ttctcctctc cggtttctct attgctttgc agctaaataa aacacttgca   1440
attcgtctcg tgatcaccgc tcatttttca accatttctt tttctactca taggggttgg   1500
cacgctcatc tggatttctt tcatccctct cgtggtaagt gcagatttct ccatcgaaag   1560
caacagcaaa cccaatttga tcgcaatgga aacccacacc taatattaac tcaaaatgtc   1620
aattgtcggt gcgtcttcct caacagatcc tcttgtgtgt tggaaccaag ctggagatga   1680
tcatcatgga gatggccctg gagatccagg accgggcgag cgtcatcaag gggccccccg   1740
tggtcgagcc cagcaacaag ttcttctggt tccaccgccc cgactgggtc ctcttcttca   1800
tacacctgac gttgttccag aacgcgtttc agatggcgca ttttgtgtgg acagtggtac   1860
gccaccgatg aacttgtcag ttaacatggg tgtcaaggca ccgagtgccg ctgatgaact   1920
gctctgacgg agatttactt gtgttgtagg ccacgcccgg cttgaagaaa tgctaccaca   1980
cgcagatcgg gctgagcatc atgaaggtgg tggtggggct agctctccag ttcctctgca   2040
gctatatgac cttccccctc tacgcgctcg tcacacaggt aataaaaccg tccaggaa     2098
```

<210> SEQ ID NO 4
<211> LENGTH: 2177
<212> TYPE: DNA
<213> ORGANISM: Oryza sativa
<220> FEATURE:

-continued

<221> NAME/KEY: misc_feature
<222> LOCATION: (4, 27, 66, 119, 136, 152, 155, 192)
<223> OTHER INFORMATION: n is a or g or c or t
<220> FEATURE:
<221> NAME/KEY: misc_feature
<222> LOCATION: (213, 241, 243, 246, 250, 456)
<223> OTHER INFORMATION: n is a or g or c or t

<400> SEQUENCE: 4

```
gcanagctga tgctgctggg cttcatntcc ctgcttctca ccgtggcaca ggcgcccatc     60
tccaanatct gcatccccaa gtcggctgcc aacatcttgt tgccgtgcaa ggcaggccna    120
gatgccatcg aagaanaagc agcaagtggt cnccngtcct tggccggcgc cggcggcggg    180
gactactgct cnaaattcga tgtgagaata acnccagctg ccggcaagca caacctcgat    240
ncnatnactn atttaactat aattgatttt tcttgggttt tctgcagggc aaggtggcgc    300
tgatgtcggc aaagagcatg caccagctgc acattttcat cttcgtgctc gccgtgttcc    360
atgttaccta ctgcatcatc accatgggtt tagggcgcct caaagtgagt ttgtcgttct    420
gtccctcatg cacatgtttt ctctagttct agcaanattg tcagtccttc aaatggattg    480
tttcgacaag aaacccaatt tattaatttg ccagttaaat atataataat tgatctttct    540
tggttttaga tgaagaaatg gaagaagtgg gagtcacaga ccaactcatt ggagtatcag    600
ttcgcaatcg gtagtgaatt aagaatctcc ctaactattt catttcagaa cctttatgat    660
aatgtcttga aagaggagga gcaaatcagc tgaaaaatat gatcgatcca tgcagatcct    720
tcacgattca ggttcacgca tcagacgtcg ttcgtgaagc ggcatctggg atcattctca    780
agcacccctg ggctcagatg gatcgtgagt tatcaatctc cgaatacatg cttgtttttt    840
attcttgcaa ctggcctagc tgttccaatt caatccatat tttttgaaaa aaaaaatatt    900
catgccgtgt ttgttgttag gtagcattct tcaggcagtt ctttgggtcc gtcaccaagg    960
tggactacct gaccatgcgg caaggcttca tcaatgtata tactaatcaa acctgaccaa   1020
ttcaacattg atgatgcaaa cagaagacca ggtttttttt ttccgagttg tgcattgaag   1080
ttaatggttt tagcttcttc tcttttgcag gcgccatttg tcgcagaata gcaagttcga   1140
cttccacaaa tacatcaaga ggtctttgga ggacgacttc aaagttgtcg ttggcatcag   1200
gtccgtcctc gctttattaa ttataggact cttatattca acattttttt tataaagaaa   1260
catatttagt ctccagttgt gtatgtgtat gtggatcttg acacatttgg ctggttttgc   1320
agcctccctc tgtggttcgt cggaatcctt gtactcttcc tcgatatcca cggtaatcct   1380
tgtcctattt cattcttttt tttactctca aaaccttgtt ctgaattggt cttataatca   1440
ccatcgattt tttttcaact ttttccccgc gtgtaggtct tggcacactt atttggatct   1500
cttttgttcc tctcatcgta agagcgaaat ttcccctgtc caaagaaaca gttaacataa   1560
ttaattatgc tttaatttat catgaaaatt aatatgatca tataactaat gaacaaacat   1620
tcatgtgaat gccaccgttg tctcagatcg tcttgttagt tgggaccaag ctagagatgg   1680
tgatcatgga gatggcccaa gagatacagg acagggccac tgtgatccag ggagcaccta   1740
tggttgaacc aagcaacaag tacttctggt tcaaccgccc tgactgggtc ttgttcttca   1800
tacacctgac actcttccca tgtacatgtt taaaaccgac ggacggatcg atcgatcacc   1860
agaacgcatt ttcagatggc gcattcgtat ggactatggt gtgtatgcta cttgcttagt   1920
tgttgccatt atcagttctt aagcaaatta agtgtgatgc atgcactgac taatgagaca   1980
aaaaatgaca cagcttgttc atcgatctgg ttgttttgtg tgtgacaggc aacacctggt   2040
ctgaagaaat gcttccatga aaatatttgg ctgagcatcg tggaagtcat tgtggggatc   2100
```

-continued tctcttcagg tgctatgcag ctagatcacc ttcccgctct acgcgctcgt cacacaggtg 2160
aacaagcaat tcacaaa 2177

<210> SEQ ID NO 5
<211> LENGTH: 2431
<212> TYPE: DNA
<213> ORGANISM: Hordeum vulgare

<400> SEQUENCE: 5
gagctcatgc tggtgggctt catatccctg ctcctcatcg tcacgcagga ccccatcatc 60
gccaagatat gcatctccga ggatgccgcc gacgtcatgt ggccctgcaa gcgcggcacc 120
gagggccgca agcccagcaa gtacgttgac tactgcccgg aggtgagcag cagagcccgg 180
accagcagct tcacgatgat gaagaaatca ataccgaact ttttcttgtt ttcttctgat 240
tgtcgtcttg gcttggctta attggtgtgt gtgtgtgtgt ttgcagggca aggtggcgct 300
catgtccacg ggcagcttgc accagctgca cgtcttcatc ttcgtgctcg cggtcttcca 360
tgtcacctac agcgtcatca ccatagctct aagccgtctc aaagtgagcc tttgcttctt 420
cttcttcttc ttttaccgca cgtctgtctg tcaggcgtac ctacctgttc atcaggcttg 480
agtaaaactg ttccataatc tgctccggca taatcctctc ctcctgcaga tgagaacatg 540
gaagaaatgg gagacagaga ccacctcctt ggaataccag ttcgcaaatg gtcaggatcc 600
cccactctgc aatctcccct tcttcgaaac caaacctgat gatccattta aagacgcagg 660
cacgatcaga gtgagtgaac tgatgtatgt tcatttttg tgtcctttca gatcctgcac 720
ggttccggtt cacgcaccag acgtcgttcg tgaagcgcca cctgggcctc tccagcaccc 780
ctggcatcag atgggtggtg agttttttag cttcttatct ggcctgtgat gtttgttgcc 840
ttgtcaggtg gccttcttca ggcagttctt caggtcagtc accaaggtgg actacctgac 900
cttgagggca ggcttcatca acgtacgtgc ctccccttct agctccgcca ttgctgccgc 960
gatgtagcag ccaaattatt ctgcgcaggc gcatttgtcg caaaacagca agttcgactt 1020
ccacaagtac atcaagaggt cgatggagga cgacttcaag gtcgtcgtcg gcatcaggta 1080
cgttccattc cttcctctgc accacaccac accccatgga tagattttaa caattgctgt 1140
caggttccac atgataacaa tatactatga acttggtctt tgctccttgt ccttgcacga 1200
tcatgacaca tttggcctgt tttcgcagcc tcccgctgtg gggtgtggcg atcctcaccc 1260
tcttccttga catcaatggt atggaccttc tcctctccgg tttctctatt gctttgcagc 1320
taaataaaac acttgcaatt cgtctcgtga tcaccgctca tttttcaacc atttcttttt 1380
ctactcatag gggttggcac gctcatctgg atttctttca tccctctcgt ggtaagtgca 1440
gatttctcca tcgaaagcaa cagcaaaccc aatttgatcg caatggaaac ccacacctaa 1500
tattaactca aaatgtcaat tgtcggtgcg tcttcctcaa cagatcctct tgtgtgttgg 1560
aaccaagctg gagatgatca tcatggagat ggccctggag atccaggacc gggcgagcgt 1620
catcaagggg gcccccgtgg tcgagcccag caacaagttc ttctggttcc accgccccga 1680
ctgggtcctc ttcttcatac acctgacgtt gttccagaac gcgtttcaga tggcgcattt 1740
tgtgtggaca gtggtacgcc accgatgaac ttgtcagtta acatgggtgt caaggcaccg 1800
agtgccgctg atgaactgct ctgacggaga tttacttgtg ttgtaggcca cgcccggctt 1860
gaagaaatgc taccacacgc agatcgggct gagcatcatg aaggtggtgg tggggctagc 1920
tctccagttc ctctgcagct atatgacctt ccccctctac gcgctcgtca cacaggtaat 1980

-continued

```
aaaaccgtaa tcatctgtgt gtgctggctt tgtatgcaga tgggatcaaa catgaagagg   2040

tccatcttcg acgagcagac gtccaaggcg ctcaccaact ggcggaacac ggccaaggag   2100

aagaagaaag tccgagacac ggacatgctg atggctcaga tgatcggcga cgcaacaccg   2160

agccgaggct cgtcgccgat gccgagccgg ggctcatcac ccgtgcacct gcttcacaag   2220

ggcatggggc ggtcggacga cccccagagc gcgcccacct cgccaaggac ccagcaggag   2280

gctagggaca tgtacccggt tgtggtggcg cacccggtgc acagactaaa tcctaacgac   2340

aggaggaggt ccgcctcgtc gtcggccctc gaagccgaca tccccagtgc agatttttcc   2400

ttcagccagg gatgagacaa gtttctgtat t                                  2431
```

<210> SEQ ID NO 6
<211> LENGTH: 2281
<212> TYPE: DNA
<213> ORGANISM: Hordeum vulgare
<220> FEATURE:
<221> NAME/KEY: misc_feature
<222> LOCATION: (7, 90, 93, 115, 177, 183, 217, 249, 254, 272, 356, 357)
<223> OTHER INFORMATION: n is a or g or c or t
<220> FEATURE:
<221> NAME/KEY: misc_feature
<222> LOCATION: (364, 1017, 1037, 1041, 1458, 1616, 1641, 1861, 1879)
<223> OTHER INFORMATION: n is a or g or c or t
<220> FEATURE:
<221> NAME/KEY: misc_feature
<222> LOCATION: (1923, 2050)
<223> OTHER INFORMATION: n is a or g or c or t

<400> SEQUENCE: 6

```
gagctcntgc tggtgggctt catatccctg ctcctcatcg tcacgcagga tcccgtctcc     60

aggatctgca tctccaagga ggccggcgan aanatgctcc cgtgcaagcc ttacnacggc    120

gccggcggtg gcaaaggcaa tgacaatcac cggaggcttc tctggctcca aggcganagc    180

ganacccacc gccggttcct ggctgccccg gccggantgg acgtctgcgc caaacaggtg    240

agcacctanc gtcnccacaa accacaaact anctaatgag catggacctg aatttcttct    300

cttcttggct tggcttgact aaattggttg tgcacggcaa ggtggcgctg atgtcnncgg    360

gaancatgca ccaactgcac atattcatct tcgtgctcgc cgtcttccac gtcttgtaca    420

gcgtcgtcac catgacccta agccgtctca aagtgagcat catactcgag ctgtttgtca    480

ataatccttg gtttccaatc caattccaaa gctggcactg atcctgctcc ggcttcctgc    540

agatgaagca atggaagaag tgggagtcgg agaccgcctc gctggagtat cagttcgcga    600

atggtcagct tccacttttc ttactgaaac cggatgcatt tacaacaaac gcacgcacga    660

tcaatcatca cagtgtgagc cgatacgttg aacccgattg aaatcctccg cagatcccat    720

cgccggtgcc ggttcacgca ccagacgacg ttgggtgagg cggcacctgg gcctctccag    780

cacccccggc gtcagatggg tggtggcctt cttcaggcag ttcttcacgt cggtgaccaa    840

ggtggactac ctgaccttgc ggcagggctt catcaacgcg catctctcgc agggcaacag    900

gttcgacttc cacaagtaca tcaagaggtc gttggaggac gacttcaaag tcgtcgtccg    960

catcaggtac gcgccattcc tttctctgca caaattaata catccaccac cacatangta   1020

gatagataga tcgatanata nattatacaa gtgccggtac gtacgtacgt ctcatatgat   1080

cttgacacat ctgtcctctt gccgcaatct caagctctgg ttcgtggcgg tcctcatcct   1140

cttccttgat ttcgacggta gccgccttgt ccatgccctg ctcgccctct cctccgcttc   1200

tctccataat ttgtgaactt gtcccgtata taaccacacc accgtcgtct tctcgcaggg   1260

gatcggcact cttctctgga tgtccgtggt tcctctcgtg gtaagtccac aatttgaata   1320
```

-continued

```
gacaacctgt ccaattgtga tgtacagtac ctccaaactt aattaacatg tcatttgctg   1380
atgtcttgcg tgtaacatta gatcctcttg tgggttggga ccaagctgga gatggtgatc   1440
atggagatgg cccagganat ccatgaccgg gagagcgtcg tcaagggtgc tcccgccgtc   1500
gagcccagca acaagtactt ctggttcaac cggcctgact gggtcctctt cctcatgcac   1560
ctcacactct tccagaacgc gtttcagatg gctcatttcg tgtggacagt ggtacntaca   1620
agtacttgtc acttcactta ngctaactcc aacaaacgaa gacacaaaac tcaatccaac   1680
gcgcggtagc aaacgaacgt ttttccgtac gttttcgtcc gctttcgccc catcccagcc   1740
caaattcgtt gacgttgttg catcgcaggc cacgcccggc ttgaagaaat gctaccacga   1800
gaaaatggca atgagcatcg ccaaggtcgt gctgggggta gccgcccaga tcttgtgcag   1860
ntacatcacc ttcccgctnt acgcgctcgt cacgcagatg ggctcacaca tgaagagaag   1920
cancttcgac gagcagacgg ccaaggcggc tgaccaactg gcgaaagatg gccaaggaga   1980
agaagaaggc ccgagacgcg gccatgctga tggcgcagat gggcggcggc gcgacgccga   2040
gcgtcggctn gtcgccggtg cacctgctcc acaaggccgg ggcgcggtcc gacgaccccc   2100
agagcgtgcc ggcgtccccg agggccgaga aggaaggcgg cggcgtgcag catccggcgc   2160
gcaaggtacc tccttgtgac gggtggaggt cggcctcgtc gccggcgctc gacgctcaca   2220
tccccggtgc agattttggc ttcagcacgc aacgttgacc gatcagacaa gttccttttt   2280
t                                                                    2281
```

<210> SEQ ID NO 7
<211> LENGTH: 1917
<212> TYPE: DNA
<213> ORGANISM: Hordeum vulgare

<400> SEQUENCE: 7

```
ggctgctccg ccagcaaacc agacacacag cagcgtacct gcgtacgtag cgtgcgcttt     60
cttttttttc ctttcgcctc tcttgcttgc tccggccggc cacgtcgata gccggccacg    120
gccaggcacc tcgcggttgc gtcgcgtgca tctgcgtgtg cgtacctggt agaggcggcc    180
gtctgcttgc tccgggcaag gaaggaggtt gcggcggtcg accgatgtcg gacaaaaaag    240
gggtgccggc gcgggagctg ccggagacgc cgtcgtgggc ggtggcggtg gtcttcgccg    300
ccatggtgct cgtgtccgtc ctcatggaac acggcctcca caagctcggc cattggttcc    360
agcaccggca caagaaggcc ctgtgggagg cgctggagaa gatgaaggcg gagctcatgc    420
tggtgggctt catatccctg ctcctcatcg tcacgcagga ccccatcatc gccaagatat    480
gcatctccga ggatgccgcc gacgtcatgt ggccctgcaa gcgcggcacc gagggccgca    540
agcccagcaa gtacgttgac tactgcccgg agggcaaggt ggcgctcatg tccacgggca    600
gcttgcacca gctgcacgtc ttcatcttcg tgctcgcggt cttccatgtc acctacagcg    660
tcatcaccat agctctaagc cgtctcaaaa tgagaacatg gaagaaatgg gagacagaga    720
ccacctcctt ggaataccag ttcgcaaatg atcctgcacg gttccggttc acgcaccaga    780
cgtcgttcgt gaagcgccac ctgggcctct ccagcacccc tggcatcaga tgggtggtgg    840
ccttcttcag gcagttcttc aggtcagtca ccaaggtgga ctacctgacc ttgagggcag    900
gcttcatcaa cgcgcatttg tcgcaaaaca gcaagttcga cttccacaag tacatcaaga    960
ggtcgatgga ggacgacttc aaggtcgtcg tcggcatcag cctcccgctg tggggtgtgg   1020
cgatcctcac cctcttcctt gacatcaatg ggttggcac gctcatctgg atttctttca   1080
```

-continued

```
tccctctcgt gatcctcttg tgtgttggaa ccaagctgga gatgatcatc atggagatgg   1140

ccctggagat ccaggaccgg gcgagcgtca tcaaggggc ccccgtggtc gagcccagca   1200

acaagttctt ctggttccac cgccccgact gggtcctctt cttcatacac ctgacgttgt   1260

tccagaacgc gtttcagatg gcgcattttg tgtggacagt ggccacgccc ggcttgaaga   1320

aatgctacca cacgcagatc gggctgagca tcatgaaggt ggtggtgggg ctagctctcc   1380

agttcctctg cagctatatg accttccccc tctacgcgct cgtcacacag atgggatcaa   1440

acatgaagag gtccatcttc gacgagcaga cgtccaaggc gctcaccaac tggcggaaca   1500

cggccaagga gaagaagaaa gtccgagaca cggacatgct gatggctcag atgatcggcg   1560

acgcaacacc gagccgaggc tcgtcgccga tgccgagccg gggctcatca cccgtgcacc   1620

tgcttcacaa gggcatgggg cggtcggacg acccccagag cgcgcccacc tcgccaagga   1680

cccagcagga ggctagggac atgtacccgg ttgtggtggc gcacccggtg cacagactaa   1740

atcctaacga caggaggagg tccgcctcgt cgtcggccct cgaagccgac atccccagtg   1800

cagattttc cttcagccag ggatgagaca agtttctgta ttcatgttag tcccaatgta   1860

tagccaacat aggatgtgat gattcgtaca ataagaaata caattttta ctgagtc      1917
```

<210> SEQ ID NO 8
<211> LENGTH: 533
<212> TYPE: PRT
<213> ORGANISM: Hordeum vulgare

<400> SEQUENCE: 8

```
Met Ser Asp Lys Lys Gly Val Pro Ala Arg Glu Leu Pro Glu Thr Pro
  1               5                  10                  15

Ser Trp Ala Val Ala Val Val Phe Ala Ala Met Val Leu Val Ser Val
             20                  25                  30

Leu Met Glu His Gly Leu His Lys Leu Gly His Trp Phe Gln His Arg
         35                  40                  45

His Lys Lys Ala Leu Trp Glu Ala Leu Glu Lys Met Lys Ala Glu Leu
     50                  55                  60

Met Leu Val Gly Phe Ile Ser Leu Leu Leu Ile Val Thr Gln Asp Pro
 65                  70                  75                  80

Ile Ile Ala Lys Ile Cys Ile Ser Glu Asp Ala Ala Asp Val Met Trp
                 85                  90                  95

Pro Cys Lys Arg Gly Thr Glu Gly Arg Lys Pro Ser Lys Tyr Val Asp
            100                 105                 110

Tyr Cys Pro Glu Gly Lys Val Ala Leu Met Ser Thr Gly Ser Leu His
        115                 120                 125

Gln Leu His Val Phe Ile Phe Val Leu Ala Val Phe His Val Thr Tyr
    130                 135                 140

Ser Val Ile Thr Ile Ala Leu Ser Arg Leu Lys Met Arg Thr Trp Lys
145                 150                 155                 160

Lys Trp Glu Thr Glu Thr Thr Ser Leu Glu Tyr Gln Phe Ala Asn Asp
                165                 170                 175

Pro Ala Arg Phe Arg Phe Thr His Gln Thr Ser Phe Val Lys Arg His
            180                 185                 190

Leu Gly Leu Ser Ser Thr Pro Gly Ile Arg Trp Val Val Ala Phe Phe
        195                 200                 205

Arg Gln Phe Phe Arg Ser Val Thr Lys Val Asp Tyr Leu Thr Leu Arg
    210                 215                 220

Ala Gly Phe Ile Asn Ala His Leu Ser Gln Asn Ser Lys Phe Asp Phe
```

-continued

```
225                 230                 235                 240

His Lys Tyr Ile Lys Arg Ser Met Glu Asp Asp Phe Lys Val Val Val
                245                 250                 255

Gly Ile Ser Leu Pro Leu Trp Gly Val Ala Ile Leu Thr Leu Phe Leu
            260                 265                 270

Asp Ile Asn Gly Val Gly Thr Leu Ile Trp Ile Ser Phe Ile Pro Leu
        275                 280                 285

Val Ile Leu Leu Cys Val Gly Thr Lys Leu Glu Met Ile Ile Met Glu
    290                 295                 300

Met Ala Leu Glu Ile Gln Asp Arg Ala Ser Val Ile Lys Gly Ala Pro
305                 310                 315                 320

Val Val Glu Pro Ser Asn Lys Phe Phe Trp Phe His Arg Pro Asp Trp
                325                 330                 335

Val Leu Phe Phe Ile His Leu Thr Leu Phe Gln Asn Ala Phe Gln Met
            340                 345                 350

Ala His Phe Val Trp Thr Val Ala Thr Pro Gly Leu Lys Lys Cys Tyr
        355                 360                 365

His Thr Gln Ile Gly Leu Ser Ile Met Lys Val Val Val Gly Leu Ala
    370                 375                 380

Leu Gln Phe Leu Cys Ser Tyr Met Thr Phe Pro Leu Tyr Ala Leu Val
385                 390                 395                 400

Thr Gln Met Gly Ser Asn Met Lys Arg Ser Ile Phe Asp Glu Gln Thr
                405                 410                 415

Ser Lys Ala Leu Thr Asn Trp Arg Asn Thr Ala Lys Glu Lys Lys Lys
            420                 425                 430

Val Arg Asp Thr Asp Met Leu Met Ala Gln Met Ile Gly Asp Ala Thr
        435                 440                 445

Pro Ser Arg Gly Ser Ser Pro Met Pro Ser Arg Gly Ser Ser Pro Val
    450                 455                 460

His Leu Leu His Lys Gly Met Gly Arg Ser Asp Asp Pro Gln Ser Ala
465                 470                 475                 480

Pro Thr Ser Pro Arg Thr Gln Gln Glu Ala Arg Asp Met Tyr Pro Val
                485                 490                 495

Val Val Ala His Pro Val His Arg Leu Asn Pro Asn Asp Arg Arg Arg
            500                 505                 510

Ser Ala Ser Ser Ser Ala Leu Glu Ala Asp Ile Pro Ser Ala Asp Phe
        515                 520                 525

Ser Phe Ser Gln Gly
    530
```

<210> SEQ ID NO 9
<211> LENGTH: 7175
<212> TYPE: DNA
<213> ORGANISM: Oryza sativa

<400> SEQUENCE: 9

```
gaattcaatt aaggacaaca acggatgata ggcttaagct agagaggatt catatggatt     60

aattaactgt acttaagttg aggtaaaact ctatcgattg ctttggacac cggctctccc    120

atgatctgcc aagttgagcc ggcctaccta attttcttcg aaagcacaca acaaacgaag    180

gtaaccacta atctagacac cacgcctaag ttatcaatta ctactctagt ctcgcgtaga    240

aacttcattc tttatggaga gtgctagtac tagagtactt aatataatag taagcgacaa    300

acccacgacg atgagaatgt acctcactta cgtaagtcaa taagtcgaaa aggaaatctt    360
```

-continued

```
gaacacttac tttattaaag aagtattccc cgaggtacag gagaggagag cacgccaata    420
actccagcac tcctccgaaa cctttctcac tctctaccct ttttctccac acaactaaaa    480
tgatgtctaa tgtatgaaag tgagttgtac tctattttgt tgtgtgtttg gaagtgaaat    540
tagctcatcc ttttatagca acttaatggt cggttgtagg ttggtagtta agtcggtaaa    600
cactcacaac caccatcgtc aaccaatagg agatcgccac atgatcgaaa gctgacagtt    660
aggggtgcca accctgtttt gtccgaacca agcaaacaac ctctatctag gacctctctt    720
ctatgtctga caagtcggcc catatggcgg tgcactatgg attaggtcaa tttcagtcgt    780
tttggactgt catgtgggcc cttccaatcc ttgtgctccc atatgattgg tcgaaggtac    840
atttaattcc tgggtgagtg ctagaactaa tatgatagat gtgctccggc tcctgggaaa    900
gaggccactt gacatacttg ggtagtgcc  ccaagggtat tccctatcgc tttttcataa    960
ttttctctct ccaaaatcgg acggaaacaa taaaaaagag aggcgatgtt catcggcaaa   1020
tatctatttt tttgatagtg tcttccctta aaacttgatt tttgcgaaga cttccggcta   1080
aaaccatgaa atcagagttc cttgtaacaa atttaatttg cctaaataca aaaaagatcg   1140
aatggagata gcattaaact tgctccatac gaatcatatt agttggaccg taactcatag   1200
aaaaagttgc aagttggttg acctatcaac cctcttatgt tgacccgtaa cctgttatgc   1260
attaaggatt aagtaccggc agatcgtcac tactcacgaa tgcacaaatt tccggtaacg   1320
taggatggga tgagttggtc agaaacgggt caccacgtcg cccaacctgc cgcgatcgag   1380
ccattggccg gcgatgcacg cgctttgaca cagccgcccg ccgccccccg gcccgccccc   1440
gtttttaata aaaaccggcc gccccctgtc aaaggtgtca aagtgtcaag tgcatcagag   1500
ctaagctagc ggtcacccag tcagctcacc ccgagacgca ccaggggatc tatcggatca   1560
tggcaggtgg gagatcggga tcgcgggagt tgccggagac gccgacgtgg gcggtggccg   1620
tcgtctgcgc cgtcctcgtg ctcgtctccg ccgccatgga gcacggcctc cacaacctca   1680
gccatgtacg cgcgcgcgca cgcggtgtgc tcatctctcg agttaatttg gttgttgttg   1740
ttgttgtgtt cttgtgacat ctcaattaac atccgatcgt ggtcgatcga tcgccctgtg   1800
gtggcgatac tgcttgcatt gcagtggttc cgtaggcggc agaagaaggc catgggcgac   1860
gccctcgaca agatcaaagc aggtcaccct cagcctcagc tcaccctcag cctccatctc   1920
taaatatttg acgccgttga cttttttaaa tatgtttgac cattcgtctt atttaaaaaa   1980
tttaagtaat tattaattct ttttctacca tttgattcat tgctaaatat actattatgt   2040
atacatatag ttttacatat ttcactaaag tttttaaata agacgaatgg tcaaacatgt   2100
ttaaaaaagt caacggcgtc aaacatttag gaagaagaga atattatatt gctgctcccc   2160
tctagccact ttgctgcctc cctcgtcatt ttttcaagta ttttacgcaa gactggtcct   2220
ccaaatcaaa cgtcacaaat aagccattta tagtttcctt tcgcttttta aggggggacta  2280
cttgtattta atcatggagg aaactaccag tcggatgtcc gattacttaa aaaaaaattc   2340
gggggactaa tttttttggc tgatcatcgg tgaaatatta ggttatatat gttgaaaaaa   2400
aatcagccac aaacaatgaa atattttgtg aaacacatat tagacacgtt gaaacgtatc   2460
attgttacgt ataaaacatc gaatgttaac agattaaaac atatgttttt ttttaatcag   2520
aatataatca tgcgatatat tattgtaaag atataattac aacgaataca acagtgcgat   2580
cggattatat atatattagt agtttaagag aaaaatcatt ttgaagatta ctagatacat   2640
acacgtatag atggatgaag tggagagaga ttagagataa gtagttatat gaattttgtg   2700
aaacacactt aagacatatg ttcaaacata ctgctattat gtatgaaata ttgagtttta   2760
```

-continued acggtttaaa acacatattc ttttaattag aatgtaataa tgtgatatct tgttgtaaaa 2820
tttaattaca tctaatataa cggtgtgatt agattgtatg ttggataaca tgcccatcgg 2880
ttggcttatt tagggaataa gccaaatggt atatttgcaa acgaaaaata atttgtaaat 2940
aaaactttta tgtatgtatt cttaacgatc tagcagcaaa ggctgaaaaa taaacttcga 3000
tgaaaaatct caaaatcaac tcttaaaatt taaattttgg cttataagta tagttcctaa 3060
ctagtttaga agaaaaaata tttaaagcgg ggaagaggaa aaggaataaa ctaatagcta 3120
aattattgca tgcatgtagc gatttgagga cgaccgagtt gttttgtctg gatcagccga 3180
ccgagacaga gcaatcttct ttaatcataa ataaccagaa aaaccatacc agttcatcac 3240
aatggaccga gtcagagtca ttacatattt ttcattgttg cgcacaggat tcaccatgtt 3300
cttatgggaa atatttttaa ctctcaaatg gttatgattt tgaactctca tttttgagag 3360
agaattaaca agcgagcgag caatcaggcc aaaaagggag aaagaaaatt atttttgtta 3420
attttttttt aaggtagggt ggaggagtca ttacatgatt tttttttata ttccctcgtt 3480
gattatatgc tgttcaaatg gttatgattt ttttaaaaga taacaacaat acaaattagt 3540
atgtgataga tcatttcacg agcatatagg attaaattta acttctgtaa attacaaaac 3600
aaacaagttt aactgttaat atacattaaa tttgtttttt tcaacttagg aattgaattt 3660
tatgtatata tttgtaaaat gatatattaa tttatttttt taaaaaaata attatttaga 3720
taacacgcaa actagaaaac caccgcagaa gttctcatat ttcttgtcct atctgcactt 3780
gcagagctga tgctgctggg cttcatatcc ctgcttctca ccgtggcaca ggcgcccatc 3840
tccaagatct gcatccccaa gtcggctgcc aacatcttgt tgccgtgcaa ggcaggccaa 3900
gatgccatcg aagaaagaag cagcaagtgg tcgccggtcc ttggccggcg ccggcggcgg 3960
ggactactgc tcgaaattcg atgtgagaat aacaccagct gccggcaagc acaacctcga 4020
tgcaataact aatttaacta taattgattt ttcttgggtt ttctgcaggg caaggtggcg 4080
ctgatgtcgg caaagagcat gcaccagctg cacattttca tcttcgtgct cgccgtgttc 4140
catgttacct actgcatcat caccatgggt ttagggcgcc tcaaagtgag tttgtcgttc 4200
tgtccctcat gcacatgttt tctctagttc tagcaagatt gtcagtcctt caaatggatt 4260
gtttcgacaa gaaacccaat ttattaattt gccagtaaat atataataat tgatctttct 4320
tggttttaga tgaagaaatg gaagaagtgg gagtcacaga ccaactcatt ggagtatcag 4380
ttcgcaatcg gtagtgaatt aagaatctcc ctaactattt catttcagaa cctttatgat 4440
aatgtcttga aagaggagga gcaaatcagc tgaaaaatat gatcgatcca tgcagatcct 4500
tcacgattca ggttcacgca tcagacgtcg ttcgtgaagc ggcatctggg atcattctca 4560
agcacccctg ggctcagatg gatcgtgagt tatcaatctc cgaatacatg cttgtttttt 4620
attcttgcaa ctggcctagc tgttccaatt caatccatat tttttgaaaa aaaaaatatt 4680
catgccgtgt ttgttgttag gtagcattct tcaggcagtt ctttgggtcc gtcaccaagg 4740
tggactacct gaccatgcgg caaggcttca tcaatgtata tactaatcaa acctgaccaa 4800
ttcaacattg atgatgcaaa cagagaccag gttttttttt tcgagtgtgc attgagtaat 4860
ggttttagct tcttctcttt tgcaggcgca tttgtcgcag aatagcaagt tcgacttcca 4920
caaatacatc aagaggtctt tggaggacga cttcaaagtt gtcgttggca tcaggtccgt 4980
cctcgcttta ttaattatag gactcttata ttcaacattt tttttataaa gaaacatatt 5040
tagtctccag ttgtgtatgt gtatgtggat cttgacacat ttggctggtt ttgcagcctc 5100

-continued

```
cctctgtggt tcgtcggaat ccttgtactc ttcctcgata tccacggtaa tccttgtcct   5160
atttcattct ttttttact ctcaaaacct tgttctgaat tggtcttata atcaccatcg   5220
attttttttc aactttttcc ccgcgtgtag gtcttggcac acttatttgg atctcttttg   5280
ttcctctcat cgtaagagcg aaatttccct gtccaaagaa acagttaaca taattaatta   5340
tgctttaatt tatcatgaaa attaatatga tcatataact aatgaacaaa cattcatgtg   5400
aatgccaccg ttgtctcaga tcgtcttgtt agttgggacc aagctagaga tggtgatcat   5460
ggagatggcc caagagatac aggacagggc cactgtgatc cagggagcac ctatggttga   5520
accaagcaac aagtacttct ggttcaaccg ccctgactgg gtcttgttct tcatacacct   5580
gacactcttc catgtacatg tttaaaacct aaaccttgct gctcaactac aaatagtact   5640
ttatctttca caattaacac ctaattaact aacatagcat ccatccattt gtggctactg   5700
atcgatggga cgacggatcg atcatcacca gaacgcattt cagatggcgc atttcgtatg   5760
gactatggtg tgtatgctac ttgcttagtt gttgccatta tcagttctta agcaaattaa   5820
gtgtgatgca tgcactgact aatgagacaa aaaatgacac agcttgttca tcgatctggt   5880
tgttttgtgt gtgacaggca acacctggtc tgaagaaatg cttccatgaa aatatttggc   5940
tgagcatcgt ggaagtcatt gtggggatct ctcttcaggt gctatgcagc tacatcacct   6000
tcccgctcta cgcgctcgtc acacaggtga acaagccatt cacaaattct attagccgtt   6060
tcttaattga tgacactgtt aatttttaga cacacgtttt gaccatttgt cttattaaaa   6120
atatttatgt aattatcatt tgagttgttt tatcactaaa agtacttttt aaataattta   6180
tattttgcat ttgtacaatt cttttaataa gataatggtc aaacatgtgt ccaaaagtta   6240
acagcatcat ctattaagaa aaggaggggt tttttttttt tggaattttg caaaatttgt   6300
tcaaaatcag tccaaaacct tttttttttt cgaaatttca gtttcactac cagtccccat   6360
aaaatgtctt ttctttattt ccacaagatt gaacccatga gatgcccttt gtgttggtat   6420
gtgttttggc catcacttgc agatgggatc gaacatgaag aagacaattt tcgaggagca   6480
aacgatgaag gcgctgatga actggaggaa gaaggcgatg gagaagaaga aggtccggga   6540
cgccgacgcg ttcctggcgc agatgagcgt cgacttcgcg acgccggcgt cgagccggtc   6600
cgcgtcgccg gtgcacctgc tgcaggtcac agggcgggtc ggacgcccgc cgagcccaat   6660
cacggtggcc tcaccaccgg caccggaggg gacatgtacc cggtgccggc ggcggctgcg   6720
tctcgccagc tgctagacga cccgccggac aggaggtgga tggcatcctc gtcggccgac   6780
atcgccgatt ctgatttttc cttcagcgca caacggtgac gggggcgatc ggtttctgta   6840
ttgatgctgt accaaacata ggagtttaat atatatataa ttgttacggt aaaatctaat   6900
tattgtgcgc gcacttatat tagtcttata gcgcgactgg ttcgtgatta gacaaggtga   6960
tgcatgctgt ttagttataa aggatatcag cgcagctaaa aaaacttact ccctacttaa   7020
tagatgacct cgttgatttt taacattatt cgtcttattt aaaaaattta tgcaaatgtt   7080
taaaacataa atcatgctta aagtactttt agtgataaaa caacttacaa caaaataaat   7140
tatagttacc taattttttt taataaatcg aatgg                              7175
```

```
<210> SEQ ID NO 10
<211> LENGTH: 4105
<212> TYPE: DNA
<213> ORGANISM: Hordeum vulgare

<400> SEQUENCE: 10

ttataccatg tgagaaaggc tggaagcata tgctcttagc agggacgcgt gcatgtttat     60
```

-continued ataggaggca taagccgaag agatatacat gaggagaggt ttaagatcag tctatcttat 120
ttacagttta aacacaagga gatagaaaga gatcctaacc tacacatgtt atacaagtca 180
cgtataatac aagagttatt tcgtctaaca ccctcccctc tgatatgata agtcgccggg 240
agagagagag agtgtgtggc tgccctcgct gcactgcacg cacatgttta cttctccgac 300
tgaaaccacg gtgaaaccgg cggcggtgtc gcactcccct gactttcctc gccggggtcc 360
cgtccggaca attaaaccgt ctgtacctgc cgggcgtcga cccgatcgtg atgtggcgcc 420
gctttgtctg cagcgagctg cgtggccgat ggcaacaaaa ctgcggtcac atacatgcat 480
accccgcata ccccgacgct caccagtaag taggctgtgg tgcggcacca cgggctcgcc 540
gccattcatg ccatgcatgg gccacccgcc ggcgaaaccg cggcgctgct gcctgccacc 600
ccgccgccgt tgacgaagac ttcgcccggc catccataaa agcatgcatg gcttgctctc 660
accggtccgg ccacacacac cacacttcac ttcgccattc gcaccaccga gagcgtagcg 720
taacgtgtgt ttgaagtcct accattaatt ttgctggatc gatggctggg ccggcgggag 780
gtcgggagct gtcggacacg ccgacgtggg cggtggcggt agtctgcgcc gtcatgatac 840
tcgtctccgt cgccatggag cacgcgctcc acaagctcgg ccacgtacgt gctctcggtt 900
cactagtgct taactgtttt tgatgttttc gggcgtgttt ggtagcctgc atggagagtg 960
tatgagccca aaagttccct ccccgaccca cttttcgctg tttggtaggg tgtatgggct 1020
gaggagagca tgcatcaact gatgcaaaaa gggcctcagc atagctgagc ccagcacccc 1080
cgcagaggcg agctgaggcg agttatgctg agcccatgca ccctcgcccc gtcgccccgt 1140
cgccccgtcg ctcccccct gcacctcttc ctcctccctc ttcctaccaa acacagtctc 1200
atccaaacat gtaacaacac atgcatgacc accaaacaac tgaagatgaa tgtattcatc 1260
atgtctatac ttaccatgca tcaacaggga acaactatgc tagggtgaga acagctgcca 1320
aacacacccg tgcacctact catgctgtgc cggcgctggc gtacgtgtgc agtggttcca 1380
caagtggcgc aagaaggccc tgggggaggc gctggagaag atgaaggcgg agctcatgct 1440
ggtgggcttc atatccctgc tcctcatcgt cacgcaggat cccgtctcca ggatctgcat 1500
ctccaaggag gccggcgaga agatgctccc gtgcaagcct tacgacggcg ccggcggtgg 1560
caaaggcaag gacaatcacc ggaggcttct ctggctccaa ggcgagagcg agacccaccg 1620
ccggttcctg gctgccccgg ccggagtgga cgtctgcgcc aaacaggtga gcacctagcg 1680
tcgccacaaa ccacaaacta gctaatgagc atggacctga atttcttctc ttcttggctt 1740
ggcttgacta aattggttgt gcagggcaag gtggcgctga tgtcagcggg aagcatgcac 1800
caactgcaca tattcatctt cgtgctcgcc gtcttccacg tcttgtacag cgtcgtcacc 1860
atgaccctaa gccgtctcaa agtgagcatc atactcgagc tgtttgtcaa taatccttgg 1920
tttccaatcc aattccaaag ctggcactga tcctgctccg gcttcctgca gatgaagcaa 1980
tggaagaagt gggagtcgga gaccgcctcg ctggagtatc agttcgcgaa tggtcagctt 2040
caacttttct tactgaaacc ggatgcattt acaacaaacg cacgcacgat caatcatcac 2100
agtgtgagcc gatacgttga accgattgaa tcctcgcaga tccatcgcgg tgccggttca 2160
cgcaccagac gacgttggtg aggcggcacc tgggcctctc cagcaccccc ggcgtcagat 2220
gggtggtggc cttcttcagg cagttcttca cgtcggtgac caaggtggac tacctgacct 2280
tgcggcaggg cttcatcaac gcgcatctct cgcagggcaa caggttcgac ttccacaagt 2340
acatcaagag gtcgttggag gacgacttca aagtcgtcgt ccgcatcagg tacgcgccat 2400

-continued

```
tcctttctct gcacaaatta atacatccac caccacatag gtagatagat agatcgatag   2460
atagattata caagtgccgg tacgtacgta cgtctcatat gatcttgaca catctgtcct   2520
cttgccgcag tctcaagctc tggttcgtgg cggtcctcat cctcttcctt gatttcgacg   2580
gtagccgcct tgtccatgcc ctgctcgccc tctcctccgc ttctctccat aatttgtgaa   2640
cttgtcccgt atataaccac accaccgtcg tcttctcgca gggatcggca ctcttctctg   2700
gatgtccgtg gttcctctcg tggtaagtcc acaatttgaa tagacaacct gtccaattgt   2760
gatgtacagt acctccaaac ttaattaaca tgtcatttgc tgatgtcttg cgtgtaacat   2820
tagatcctct tgtgggttgg gaccaagctg gagatggtga tcatggagat ggcccaggag   2880
atccatgacc gggagagcgt cgtcaagggt gctcccgccg tcgagcccag caacaagtac   2940
ttctggttca accggcctga ctgggtcctc ttcctcatgc acctcacact cttccagaac   3000
gcgtttcaga tggctcattt cgtgtggaca gtggtacgta caagtacttg tcacttcact   3060
taggctaact ccaacaaacg accccaaatt aatggtccgt cgcgtctgtt tggggtatgt   3120
ttggggtaaa cggacacaaa actcaatcca acgcgcggta gcaaacgaac gtttttccgt   3180
acgttttcgt ccgctttcgc cccatcccag cccaaattcg ttgacgttgt tgcatcgcag   3240
gccacgcccg gcttgaagaa atgctaccac gagaaaatgg caatgagcat cgccaaggtc   3300
gtgctggggg tagccgccca gatcttgtgc agctacatca ccttcccgct ctacgcgctc   3360
gtcacgcaga tgggctcaca catgaagaga agcatcttcg acgagcagac ggccaaggcg   3420
ctgaccaact ggcgaaagat ggccaaggag aagaagaagg cccgagacgc ggccatgctg   3480
atggcgcaga tgggcggcgg cgcgacgccg agcgtcggct cgtcgccggt gcacctgctc   3540
cacaaggccg gggcgcggtc cgacgacccc cagagcgtgc cggcgtcccc gagggccgag   3600
aaggaaggcg gcggcgtgca gcatccggcg cgcaaggtac ctccttgtga cgggtggagg   3660
tcggcctcgt cgccggcgct cgacgctcac atccccggtg cagattttgg cttcagcacg   3720
caacgttgac cgatcagaca agttcctttt tttttcggtg aatagaagcg tatcatttca   3780
ttgatagaca gtagaaatta caggaatggc tgtcctacta ctatgtacac aagggcacag   3840
caaaggatca ttgatcttgt tacaagagca gtagaaaggg attgctctcc attgatcttg   3900
ttaagttgta tgtcacaaat tgttgcagaa aaaagtgtat gtcatcccaa ccaagagctg   3960
agtttgtgat gattcgtgca ataagaattg caagtttcac cgagtcaaaa atgaagcttc   4020
taagtacgca ccaaccaacg gactctttca tctcaacaaa agaactgtaa atggcaataa   4080
ttctgataac atcggaaggg agctc                                         4105
```

<210> SEQ ID NO 11
<211> LENGTH: 1611
<212> TYPE: DNA
<213> ORGANISM: Oryza sativa

<400> SEQUENCE: 11

```
atggcaggtg ggagatcggg atcgcgggag ttgccggaga cgccgacgtg ggcggtggcc     60
gtcgtctgcg ccgtcctcgt gctcgtctcc gccgccatgg agcacggcct ccacaacctc    120
agccataaaa ccaccgcaga agttctcata tttcttgtcc tatctgcact tgcagagctg    180
atgctgctgg gcttcatatc cctgcttctc accgtggcac aggcgcccat ctccaagatc    240
tgcatcccca agtcggctgc caacatcttg ttgccgtgca aggcaggcca agatgccatc    300
gaagaagaag cagcaagtgg tcgccggtcc ttggccggcg ccggcggcgg ggactactgc    360
tcgaaattcg atggcaaggt ggcgctgatg tcggcaaaga gcatgcacca gctgcacatt    420
```

-continued

```
ttcatcttcg tgctcgccgt gttccatgtt acctactgca tcatcaccat gggtttaggg    480
cgcctcaaaa tgaagaaatg gaagaagtgg gagtcacaga ccaactcatt ggagtatcag    540
ttcgcaatcg atccttcacg attcaggttc acgcatcaga cgtcgttcgt gaagcggcat    600
ctgggatcat tctcaagcac ccctgggctc agatggatcg tagcattctt caggcagttc    660
tttgggtccg tcaccaaggt ggactacctg accatgcggc aaggcttcat caatgcgcat    720
ttgtcgcaga atagcaagtt cgacttccac aaatacatca agaggtcttt ggaggacgac    780
ttcaaagttg tcgttggcat cagcctccct ctgtggttcg tcggaatcct tgtactcttc    840
ctcgatatcc acggtcttgg cacacttatt tggatctctt ttgttcctct catcatcgtc    900
ttgttagttg ggaccaagct agagatggtg atcatggaga tggcccaaga gatacaggac    960
agggccactg tgatccaggg agcacctatg gttgaaccaa gcaacaagta cttctggttc   1020
aaccgccctg actgggtctt gttcttcata cacctgacac tcttccataa cgcatttcag   1080
atggcgcatt tcgtatggac tatggcaaca cctggtctga agaaatgctt ccatgaaaat   1140
atttggctga gcatcgtgga agtcattgtg ggatctctc ttcaggtgct atgcagctac   1200
atcaccttcc cgctctacgc gctcgtcaca cagatgggat cgaacatgaa gaagacaatt   1260
ttcgaggagc aaacgatgaa ggcgctgatg aactggagga agaaggcgat ggagaagaag   1320
aaggtccggg acgccgacgc gttcctggcg cagatgagcg tcgacttcgc gacgccggcg   1380
tcgagccggt ccgcgtcgcc ggtgcacctg ctgcaggtca cagggcgggt cggacgcccg   1440
ccgagcccaa tcacggtggc ctcaccaccg gcaccggagg aggacatgta cccggtgccg   1500
gcggcggctg cgtctcgcca gctgctagac gacccgccgg acaggaggtg gatggcatcc   1560
tcgtcggccg acatcgccga ttctgatttt tccttcagcg cacaacggtg a            1611
```

<210> SEQ ID NO 12
<211> LENGTH: 1635
<212> TYPE: DNA
<213> ORGANISM: Hordeum vulgare

<400> SEQUENCE: 12

```
atggctgggc cggcgggagg tcgggagctg tcggacacgc cgacgtgggc ggtggcggta     60
gtctgcgccg tcatgatact cgtctccgtc gccatggagc acgcgctcca caagctcggc    120
cactggttcc acaagtggcg caagaaggcc ctgggggagg cgctggagaa gatgaaggcg    180
gagctcatgc tggtgggctt catatccctg ctcctcatcg tcacgcagga tcccgtctcc    240
aggatctgca tctccaagga ggccggcgag aagatgctcc cgtgcaagcc ttacgacggc    300
gccggcggtg gcaaaggcaa ggacaatcac cggaggcttc tctggctcca aggcgagagc    360
gagacccacc gccggttcct ggctgccccg gccggagtgg acgtctgcgc caaacagggc    420
aaggtggcgc tgatgtcagc gggaagcatg caccaactgc acatattcat cttcgtgctc    480
gccgtcttcc acgtcttgta cagcgtcgtc accatgaccc taagccgtct caaaatgaag    540
caatggaaga agtgggagtc ggagaccgcc tcgctggagt atcagttcgc gaatgatcca    600
tcgcggtgcc ggttcacgca ccagacgacg ttggtgaggc ggcacctggg cctctccagc    660
acccccggcg tcagatgggt ggtggccttc ttcaggcagt tcttcacgtc ggtgaccaag    720
gtggactacc tgaccttgcg gcagggcttc atcaacgcgc atctctcgca gggcaacagg    780
ttcgacttcc acaagtacat caagaggtcg ttggaggacg acttcaaagt cgtcgtccgc    840
atcagtctca agctctggtt cgtggcggtc ctcatcctct tccttgattt cgacgggatc    900
```

-continued

```
ggcactcttc tctggatgtc cgtggttcct ctcgtgatcc tcttgtgggt tgggaccaag    960
ctggagatgg tgatcatgga gatggcccag gagatccatg accgggagag cgtcgtcaag   1020
ggtgctcccg ccgtcgagcc cagcaacaag tacttctggt tcaaccggcc tgactgggtc   1080
ctcttcctca tgcacctcac actcttccag aacgcgtttc agatggctca tttcgtgtgg   1140
acagtggcca cgcccggctt gaagaaatgc taccacgaga aaatggcaat gagcatcgcc   1200
aaggtcgtgc tgggggtagc cgcccagatc ttgtgcagct acatcacctt cccgctctac   1260
gcgctcgtca cgcagatggg ctcacacatg aagagaagca tcttcgacga gcagacggcc   1320
aaggcgctga ccaactggcg aaagatggcc aaggagaaga agaaggcccg agacgcggcc   1380
atgctgatgg cgcagatggg cggcggcgcg acgccgagcg tcggctcgtc gccggtgcac   1440
ctgctccaca aggccggggc gcggtccgac gacccccaga gcgtgccggc gtccccgagg   1500
gccgagaagg aaggcggcgg cgtgcagcat ccggcgcgca aggtacctcc ttgtgacggg   1560
tggaggtcgg cctcgtcgcc ggcgctcgac gctcacatcc ccggtgcaga ttttggcttc   1620
agcacgcaac gttga                                                    1635
```

<210> SEQ ID NO 13
<211> LENGTH: 1880
<212> TYPE: DNA
<213> ORGANISM: Arabidopsis thaliana

<400> SEQUENCE: 13

```
gttggtacat aaaagactct tcctttgtct gttttttgtt cccagattca tctttactta     60
ttgactaaat tctctctggt gtgagaagta aaatgggtca cggaggagaa gggatgtcgc    120
ttgaattcac tccgacgtgg gtcgtcgccg gagtttgtac ggtcatcgtc gcgatttcac    180
tggcggtgga gcgtttgctt cactatttcg gtactgttct taagaagaag aagcaaaaac    240
ccctttacga agcccttcaa aaggttaaag aagagctgat gttgttaggg tttatatcgc    300
tgttactgac ggtattccaa gggctcattt ccaaattctg tgtgaaagaa aatgtgctta    360
tgcatatgct tccatgttct ctcgattcaa gacgagaagc tggggcaagt gaacataaaa    420
acgttacagc aaaagaacat tttcagactt ttttacctat tgttggaacc actaggcgtc    480
tacttgctga acatgctgct gtgcaagttg gttactgtag cgaaaagggt aaagtaccat    540
tgctttcgct tgaggcattg caccatctac atattttcat cttcgtcctc gccatatccc    600
atgtgacatt ctgtgtcctt accgtgattt ttggaagcac aaggattcac caatggaaga    660
aatgggagga ttcgatcgca gatgagaagt ttgaccccga aacagctctc aggaaaagaa    720
gggtcactca tgtacacaac catgctttta ttaaagagca ttttcttggt attggcaaag    780
attcagtcat cctcggatgg acgcaatcct ttctcaagca attctatgat tctgtgacga    840
aatcagatta cgtgacttta cgtcttggtt tcattatgac acattgtaag ggaaacccca    900
agcttaattt ccacaagtat atgatgcgcg ctctagagga tgatttcaaa caagttgttg    960
gtattagttg gtatctttgg atctttgtcg tcatcttttt gctgctaaat gttaacggat   1020
ggcacacata tttctggata gcatttattc cctttgcttt gcttcttgct gtgggaacaa   1080
agttggagca tgtgattgca cagttagctc atgaagttgc agagaaacat gtagccattg   1140
aaggagactt agtggtgaaa ccctcagatg agcatttctg gttcagcaaa cctcaaattg   1200
ttctctactt gatccatttt atcctcttcc agaatgcttt tgagattgcg tttttctttt   1260
ggatttgggt tacatacggc ttcgactcgt gcattatggg acaggtgaga tacattgttc   1320
caagattggt tatcggggtc ttcattcaag tgctttgcag ttacagtaca ctgcctcttt   1380
```

-continued

```
acgccatcgt ctcacagatg ggaagtagct tcaagaaagc tatattcgag gagaatgtgc   1440
aggttggtct tgttggttgg gcacagaaag tgaaacaaaa gagagaccta aaagctgcag   1500
ctagtaatgg agacgaagga agctctcagg ctggtcctgg tcctgattct ggttctggtt   1560
ctgctcctgc tgctggtcct ggtgcaggtt ttgcaggaat tcagctcagc agagtaacaa   1620
gaaacaacgc aggggacaca aacaatgaga ttacacctga tcataacaac tgagcagaga   1680
tattatcttt tccatttaga ggatcatcat cagattttag cttcaaggtc cggttttgtg   1740
gtttatacat aagttatagt gacttgattt ttttgttttg ttacaaagtt accatctttg   1800
gattagaatt gggaaattga atctgtttgt atattgtatt atttggaaca ttgtggatgc   1860
ccatggatat gtttctgttc                                                 1880
```

<210> SEQ ID NO 14
<211> LENGTH: 536
<212> TYPE: PRT
<213> ORGANISM: Oryza sativa

<400> SEQUENCE: 14

```
Met Ala Gly Gly Arg Ser Gly Ser Arg Glu Leu Pro Glu Thr Pro Thr
  1               5                  10                  15

Trp Ala Val Ala Val Val Cys Ala Val Leu Val Leu Val Ser Ala Ala
             20                  25                  30

Met Glu His Gly Leu His Asn Leu Ser His Lys Thr Thr Ala Glu Val
         35                  40                  45

Leu Ile Phe Leu Val Leu Ser Ala Leu Ala Glu Leu Met Leu Leu Gly
     50                  55                  60

Phe Ile Ser Leu Leu Leu Thr Val Ala Gln Ala Pro Ile Ser Lys Ile
 65                  70                  75                  80

Cys Ile Pro Lys Ser Ala Ala Asn Ile Leu Leu Pro Cys Lys Ala Gly
                 85                  90                  95

Gln Asp Ala Ile Glu Glu Glu Ala Ala Ser Gly Arg Arg Ser Leu Ala
            100                 105                 110

Gly Ala Gly Gly Gly Asp Tyr Cys Ser Lys Phe Asp Gly Lys Val Ala
        115                 120                 125

Leu Met Ser Ala Lys Ser Met His Gln Leu His Ile Phe Ile Phe Val
    130                 135                 140

Leu Ala Val Phe His Val Thr Tyr Cys Ile Ile Thr Met Gly Leu Gly
145                 150                 155                 160

Arg Leu Lys Met Lys Lys Trp Lys Lys Trp Glu Ser Gln Thr Asn Ser
                165                 170                 175

Leu Glu Tyr Gln Phe Ala Ile Asp Pro Ser Arg Phe Arg Phe Thr His
            180                 185                 190

Gln Thr Ser Phe Val Lys Arg His Leu Gly Ser Phe Ser Ser Thr Pro
        195                 200                 205

Gly Leu Arg Trp Ile Val Ala Phe Phe Arg Gln Phe Phe Gly Ser Val
    210                 215                 220

Thr Lys Val Asp Tyr Leu Thr Met Arg Gln Gly Phe Ile Asn Ala His
225                 230                 235                 240

Leu Ser Gln Asn Ser Lys Phe Asp Phe His Lys Tyr Ile Lys Arg Ser
                245                 250                 255

Leu Glu Asp Asp Phe Lys Val Val Val Gly Ile Ser Leu Pro Leu Trp
            260                 265                 270

Phe Val Gly Ile Leu Val Leu Phe Leu Asp Ile His Gly Leu Gly Thr
```

-continued

```
        275                 280                 285

Leu Ile Trp Ile Ser Phe Val Pro Leu Ile Ile Val Leu Leu Val Gly
    290                 295                 300

Thr Lys Leu Glu Met Val Ile Met Glu Met Ala Gln Glu Ile Gln Asp
305                 310                 315                 320

Arg Ala Thr Val Ile Gln Gly Ala Pro Met Val Glu Pro Ser Asn Lys
                325                 330                 335

Tyr Phe Trp Phe Asn Arg Pro Asp Trp Val Leu Phe Phe Ile His Leu
            340                 345                 350

Thr Leu Phe His Asn Ala Phe Gln Met Ala His Phe Val Trp Thr Met
        355                 360                 365

Ala Thr Pro Gly Leu Lys Lys Cys Phe His Glu Asn Ile Trp Leu Ser
    370                 375                 380

Ile Val Glu Val Ile Val Gly Ile Ser Leu Gln Val Leu Cys Ser Tyr
385                 390                 395                 400

Ile Thr Phe Pro Leu Tyr Ala Leu Val Thr Gln Met Gly Ser Asn Met
                405                 410                 415

Lys Lys Thr Ile Phe Glu Glu Gln Thr Met Lys Ala Leu Met Asn Trp
            420                 425                 430

Arg Lys Lys Ala Met Glu Lys Lys Lys Val Arg Asp Ala Asp Ala Phe
        435                 440                 445

Leu Ala Gln Met Ser Val Asp Phe Ala Thr Pro Ala Ser Ser Arg Ser
    450                 455                 460

Ala Ser Pro Val His Leu Leu Gln Val Thr Gly Arg Val Gly Arg Pro
465                 470                 475                 480

Pro Ser Pro Ile Thr Val Ala Ser Pro Pro Ala Pro Glu Glu Asp Met
                485                 490                 495

Tyr Pro Val Pro Ala Ala Ala Ala Ser Arg Gln Leu Leu Asp Asp Pro
            500                 505                 510

Pro Asp Arg Arg Trp Met Ala Ser Ser Ser Ala Asp Ile Ala Asp Ser
        515                 520                 525

Asp Phe Ser Phe Ser Ala Gln Arg
    530                 535


<210> SEQ ID NO 15
<211> LENGTH: 544
<212> TYPE: PRT
<213> ORGANISM: Hordeum vulgare

<400> SEQUENCE: 15

Met Ala Gly Pro Ala Gly Gly Arg Glu Leu Ser Asp Thr Pro Thr Trp
  1               5                  10                  15

Ala Val Ala Val Val Cys Ala Val Met Ile Leu Val Ser Val Ala Met
             20                  25                  30

Glu His Ala Leu His Lys Leu Gly His Trp Phe His Lys Trp Arg Lys
         35                  40                  45

Lys Ala Leu Gly Glu Ala Leu Glu Lys Met Lys Ala Glu Leu Met Leu
     50                  55                  60

Val Gly Phe Ile Ser Leu Leu Leu Ile Val Thr Gln Asp Pro Val Ser
 65                  70                  75                  80

Arg Ile Cys Ile Ser Lys Glu Ala Gly Glu Lys Met Leu Pro Cys Lys
                 85                  90                  95

Pro Tyr Asp Gly Ala Gly Gly Gly Lys Gly Lys Asp Asn His Arg Arg
            100                 105                 110
```

-continued

```
Leu Leu Trp Leu Gln Gly Glu Ser Glu Thr His Arg Arg Phe Leu Ala
        115                 120                 125

Ala Pro Ala Gly Val Asp Val Cys Ala Lys Gln Gly Lys Val Ala Leu
    130                 135                 140

Met Ser Ala Gly Ser Met His Gln Leu His Ile Phe Ile Phe Val Leu
145                 150                 155                 160

Ala Val Phe His Val Leu Tyr Ser Val Val Thr Met Thr Leu Ser Arg
                165                 170                 175

Leu Lys Met Lys Gln Trp Lys Lys Trp Glu Ser Glu Thr Ala Ser Leu
            180                 185                 190

Glu Tyr Gln Phe Ala Asn Asp Pro Ser Arg Cys Arg Phe Thr His Gln
        195                 200                 205

Thr Thr Leu Val Arg Arg His Leu Gly Leu Ser Ser Thr Pro Gly Val
    210                 215                 220

Arg Trp Val Val Ala Phe Phe Arg Gln Phe Phe Thr Ser Val Thr Lys
225                 230                 235                 240

Val Asp Tyr Leu Thr Leu Arg Gln Gly Phe Ile Asn Ala His Leu Ser
                245                 250                 255

Gln Gly Asn Arg Phe Asp Phe His Lys Tyr Ile Lys Arg Ser Leu Glu
            260                 265                 270

Asp Asp Phe Lys Val Val Val Arg Ile Ser Leu Lys Leu Trp Phe Val
        275                 280                 285

Ala Val Leu Ile Leu Phe Leu Asp Phe Asp Gly Ile Gly Thr Leu Leu
    290                 295                 300

Trp Met Ser Val Val Pro Leu Val Ile Leu Leu Trp Val Gly Thr Lys
305                 310                 315                 320

Leu Glu Met Val Ile Met Glu Met Ala Gln Glu Ile His Asp Arg Glu
                325                 330                 335

Ser Val Val Lys Gly Ala Pro Ala Val Glu Pro Ser Asn Lys Tyr Phe
            340                 345                 350

Trp Phe Asn Arg Pro Asp Trp Val Leu Phe Leu Met His Leu Thr Leu
        355                 360                 365

Phe Gln Asn Ala Phe Gln Met Ala His Phe Val Trp Thr Val Ala Thr
    370                 375                 380

Pro Gly Leu Lys Lys Cys Tyr His Glu Lys Met Ala Met Ser Ile Ala
385                 390                 395                 400

Lys Val Val Leu Gly Val Ala Ala Gln Ile Leu Cys Ser Tyr Ile Thr
                405                 410                 415

Phe Pro Leu Tyr Ala Leu Val Thr Gln Met Gly Ser His Met Lys Arg
            420                 425                 430

Ser Ile Phe Asp Glu Gln Thr Ala Lys Ala Leu Thr Asn Trp Arg Lys
        435                 440                 445

Met Ala Lys Glu Lys Lys Lys Ala Arg Asp Ala Ala Met Leu Met Ala
    450                 455                 460

Gln Met Gly Gly Gly Ala Thr Pro Ser Val Gly Ser Ser Pro Val His
465                 470                 475                 480

Leu Leu His Lys Ala Gly Ala Arg Ser Asp Asp Pro Gln Ser Val Pro
                485                 490                 495

Ala Ser Pro Arg Ala Glu Lys Glu Gly Gly Gly Val Gln His Pro Ala
            500                 505                 510

Arg Lys Val Pro Pro Cys Asp Gly Trp Arg Ser Ala Ser Ser Pro Ala
        515                 520                 525

Leu Asp Ala His Ile Pro Gly Ala Asp Phe Gly Phe Ser Thr Gln Arg
```

-continued 530 535 540

<210> SEQ ID NO 16
<211> LENGTH: 526
<212> TYPE: PRT
<213> ORGANISM: Arabidopsis thaliana

<400> SEQUENCE: 16

Met Gly His Gly Gly Glu Gly Met Ser Leu Glu Phe Thr Pro Thr Trp
1 5 10 15

Val Val Ala Gly Val Cys Thr Val Ile Val Ala Ile Ser Leu Ala Val
20 25 30

Glu Arg Leu Leu His Tyr Phe Gly Thr Val Leu Lys Lys Lys Lys Gln
35 40 45

Lys Pro Leu Tyr Glu Ala Leu Gln Lys Val Lys Glu Glu Leu Met Leu
50 55 60

Leu Gly Phe Ile Ser Leu Leu Leu Thr Val Phe Gln Gly Leu Ile Ser
65 70 75 80

Lys Phe Cys Val Lys Glu Asn Val Leu Met His Met Leu Pro Cys Ser
85 90 95

Leu Asp Ser Arg Arg Glu Ala Gly Ala Ser Glu His Lys Asn Val Thr
100 105 110

Ala Lys Glu His Phe Gln Thr Phe Leu Pro Ile Val Gly Thr Thr Arg
115 120 125

Arg Leu Leu Ala Glu His Ala Ala Val Gln Val Gly Tyr Cys Ser Glu
130 135 140

Lys Gly Lys Val Pro Leu Leu Ser Leu Glu Ala Leu His His Leu His
145 150 155 160

Ile Phe Ile Phe Val Leu Ala Ile Ser His Val Thr Phe Cys Val Leu
165 170 175

Thr Val Ile Phe Gly Ser Thr Arg Ile His Gln Trp Lys Lys Trp Glu
180 185 190

Asp Ser Ile Ala Asp Glu Lys Phe Asp Pro Glu Thr Ala Leu Arg Lys
195 200 205

Arg Arg Val Thr His Val His Asn His Ala Phe Ile Lys Glu His Phe
210 215 220

Leu Gly Ile Gly Lys Asp Ser Val Ile Leu Gly Trp Thr Gln Ser Phe
225 230 235 240

Leu Lys Gln Phe Tyr Asp Ser Val Thr Lys Ser Asp Tyr Val Thr Leu
245 250 255

Arg Leu Gly Phe Ile Met Thr His Cys Lys Gly Asn Pro Lys Leu Asn
260 265 270

Phe His Lys Tyr Met Met Arg Ala Leu Glu Asp Asp Phe Lys Gln Val
275 280 285

Val Gly Ile Ser Trp Tyr Leu Trp Ile Phe Val Val Ile Phe Leu Leu
290 295 300

Leu Asn Val Asn Gly Trp His Thr Tyr Phe Trp Ile Ala Phe Ile Pro
305 310 315 320

Phe Ala Leu Leu Leu Ala Val Gly Thr Lys Leu Glu His Val Ile Ala
325 330 335

Gln Leu Ala His Glu Val Ala Glu Lys His Val Ala Ile Glu Gly Asp
340 345 350

Leu Val Val Lys Pro Ser Asp Glu His Phe Trp Phe Ser Lys Pro Gln
355 360 365

-continued

```
Ile Val Leu Tyr Leu Ile His Phe Ile Leu Phe Gln Asn Ala Phe Glu
    370                 375                 380

Ile Ala Phe Phe Phe Trp Ile Trp Val Thr Tyr Gly Phe Asp Ser Cys
385                 390                 395                 400

Ile Met Gly Gln Val Arg Tyr Ile Val Pro Arg Leu Val Ile Gly Val
                405                 410                 415

Phe Ile Gln Val Leu Cys Ser Tyr Ser Thr Leu Pro Leu Tyr Ala Ile
            420                 425                 430

Val Ser Gln Met Gly Ser Ser Phe Lys Lys Ala Ile Phe Glu Glu Asn
        435                 440                 445

Val Gln Val Gly Leu Val Gly Trp Ala Gln Lys Val Lys Gln Lys Arg
    450                 455                 460

Asp Leu Lys Ala Ala Ala Ser Asn Gly Asp Glu Gly Ser Ser Gln Ala
465                 470                 475                 480

Gly Pro Gly Pro Asp Ser Gly Ser Gly Ser Ala Pro Ala Ala Gly Pro
                485                 490                 495

Gly Ala Gly Phe Ala Gly Ile Gln Leu Ser Arg Val Thr Arg Asn Asn
            500                 505                 510

Ala Gly Asp Thr Asn Asn Glu Ile Thr Pro Asp His Asn Asn
        515                 520                 525


<210> SEQ ID NO 17
<211> LENGTH: 544
<212> TYPE: PRT
<213> ORGANISM: Hordeum vulgare

<400> SEQUENCE: 17

Met Ala Gly Pro Ala Gly Gly Arg Glu Leu Ser Asp Thr Pro Thr Trp
  1               5                  10                  15

Ala Val Ala Val Val Cys Ala Val Met Ile Leu Val Ser Val Ala Met
             20                  25                  30

Glu His Ala Leu His Lys Leu Gly His Trp Phe His Lys Trp Arg Lys
         35                  40                  45

Lys Ala Leu Gly Glu Ala Leu Glu Lys Met Lys Ala Glu Leu Met Leu
     50                  55                  60

Val Gly Phe Ile Ser Leu Leu Leu Ile Val Thr Gln Asp Pro Val Ser
 65                  70                  75                  80

Arg Ile Cys Ile Ser Lys Glu Ala Gly Glu Lys Met Leu Pro Cys Lys
                 85                  90                  95

Pro Tyr Asp Gly Ala Gly Gly Gly Lys Gly Lys Asp Asn His Arg Arg
            100                 105                 110

Leu Leu Trp Leu Gln Gly Glu Ser Glu Thr His Arg Arg Phe Leu Ala
        115                 120                 125

Ala Pro Ala Gly Val Asp Val Cys Ala Lys Gln Gly Lys Val Ala Leu
    130                 135                 140

Met Ser Ala Gly Ser Met His Gln Leu His Ile Phe Ile Phe Val Leu
145                 150                 155                 160

Ala Val Phe His Val Leu Tyr Ser Val Val Thr Met Thr Leu Ser Arg
                165                 170                 175

Leu Lys Met Lys Gln Trp Lys Lys Trp Glu Ser Glu Thr Ala Ser Leu
            180                 185                 190

Glu Tyr Gln Phe Ala Asn Asp Pro Ser Arg Cys Arg Phe Thr His Gln
        195                 200                 205

Thr Thr Leu Val Arg Arg His Leu Gly Leu Ser Ser Thr Pro Gly Val
    210                 215                 220
```

-continued

```
Arg Trp Val Val Ala Phe Phe Arg Gln Phe Phe Thr Ser Val Thr Lys
225                 230                 235                 240

Val Asp Tyr Leu Thr Leu Arg Gln Gly Phe Ile Asn Ala His Leu Ser
                245                 250                 255

Gln Gly Asn Arg Phe Asp Phe His Lys Tyr Ile Lys Arg Ser Leu Glu
            260                 265                 270

Asp Asp Phe Lys Val Val Val Arg Ile Ser Leu Lys Leu Trp Phe Val
        275                 280                 285

Ala Val Leu Ile Leu Phe Leu Asp Phe Asp Gly Ile Gly Thr Leu Leu
    290                 295                 300

Trp Met Ser Val Val Pro Leu Val Ile Leu Leu Trp Val Gly Thr Lys
305                 310                 315                 320

Leu Glu Met Val Ile Met Glu Met Ala Gln Glu Ile His Asp Arg Glu
                325                 330                 335

Ser Val Val Lys Gly Ala Pro Ala Val Glu Pro Ser Asn Lys Tyr Phe
            340                 345                 350

Trp Phe Asn Arg Pro Asp Trp Val Leu Phe Leu Met His Leu Thr Leu
        355                 360                 365

Phe Gln Asn Ala Phe Gln Met Ala His Phe Val Trp Thr Val Ala Thr
    370                 375                 380

Pro Gly Leu Lys Lys Cys Tyr His Glu Lys Met Ala Met Ser Ile Ala
385                 390                 395                 400

Lys Val Val Leu Gly Val Ala Ala Gln Ile Leu Cys Ser Tyr Ile Thr
                405                 410                 415

Phe Pro Leu Tyr Ala Leu Val Thr Gln Met Gly Ser His Met Lys Arg
            420                 425                 430

Ser Ile Phe Asp Glu Gln Thr Ala Lys Ala Leu Thr Asn Trp Arg Lys
        435                 440                 445

Met Ala Lys Glu Lys Lys Lys Ala Arg Asp Ala Ala Met Leu Met Ala
    450                 455                 460

Gln Met Gly Gly Gly Ala Thr Pro Ser Val Gly Ser Ser Pro Val His
465                 470                 475                 480

Leu Leu His Lys Ala Gly Ala Arg Ser Asp Asp Pro Gln Ser Val Pro
                485                 490                 495

Ala Ser Pro Arg Ala Glu Lys Glu Gly Gly Gly Val Gln His Pro Ala
            500                 505                 510

Arg Lys Val Pro Pro Cys Asp Gly Trp Arg Ser Ala Ser Ser Pro Ala
        515                 520                 525

Leu Asp Ala His Ile Pro Gly Ala Asp Phe Gly Phe Ser Thr Gln Arg
    530                 535                 540


<210> SEQ ID NO 18
<211> LENGTH: 536
<212> TYPE: PRT
<213> ORGANISM: Oryza sativa

<400> SEQUENCE: 18

Met Ala Gly Gly Arg Ser Gly Ser Arg Glu Leu Pro Glu Thr Pro Thr
  1               5                  10                  15

Trp Ala Val Ala Val Val Cys Ala Val Leu Val Leu Val Ser Ala Ala
            20                  25                  30

Met Glu His Gly Leu His Asn Leu Ser His Lys Thr Thr Ala Glu Val
        35                  40                  45

Leu Ile Phe Leu Val Leu Ser Ala Leu Ala Glu Leu Met Leu Leu Gly
```

-continued

```
     50                  55                  60

Phe Ile Ser Leu Leu Leu Thr Val Ala Gln Ala Pro Ile Ser Lys Ile
 65                  70                  75                  80

Cys Ile Pro Lys Ser Ala Ala Asn Ile Leu Leu Pro Cys Lys Ala Gly
                 85                  90                  95

Gln Asp Ala Ile Glu Glu Glu Ala Ala Ser Gly Arg Arg Ser Leu Ala
            100                 105                 110

Gly Ala Gly Gly Gly Asp Tyr Cys Ser Lys Phe Asp Gly Lys Val Ala
        115                 120                 125

Leu Met Ser Ala Lys Ser Met His Gln Leu His Ile Phe Ile Phe Val
    130                 135                 140

Leu Ala Val Phe His Val Thr Tyr Cys Ile Ile Thr Met Gly Leu Gly
145                 150                 155                 160

Arg Leu Lys Met Lys Lys Trp Lys Lys Trp Glu Ser Gln Thr Asn Ser
                165                 170                 175

Leu Glu Tyr Gln Phe Ala Ile Asp Pro Ser Arg Phe Arg Phe Thr His
            180                 185                 190

Gln Thr Ser Phe Val Lys Arg His Leu Gly Ser Phe Ser Ser Thr Pro
        195                 200                 205

Gly Leu Arg Trp Ile Val Ala Phe Phe Arg Gln Phe Phe Gly Ser Val
    210                 215                 220

Thr Lys Val Asp Tyr Leu Thr Met Arg Gln Gly Phe Ile Asn Ala His
225                 230                 235                 240

Leu Ser Gln Asn Ser Lys Phe Asp Phe His Lys Tyr Ile Lys Arg Ser
                245                 250                 255

Leu Glu Asp Asp Phe Lys Val Val Val Gly Ile Ser Leu Pro Leu Trp
            260                 265                 270

Phe Val Gly Ile Leu Val Leu Phe Leu Asp Ile His Gly Leu Gly Thr
        275                 280                 285

Leu Ile Trp Ile Ser Phe Val Pro Leu Ile Ile Val Leu Leu Val Gly
    290                 295                 300

Thr Lys Leu Glu Met Val Ile Met Glu Met Ala Gln Glu Ile Gln Asp
305                 310                 315                 320

Arg Ala Thr Val Ile Gln Gly Ala Pro Met Val Glu Pro Ser Asn Lys
                325                 330                 335

Tyr Phe Trp Phe Asn Arg Pro Asp Trp Val Leu Phe Phe Ile His Leu
            340                 345                 350

Thr Leu Phe His Asn Ala Phe Gln Met Ala His Phe Val Trp Thr Met
        355                 360                 365

Ala Thr Pro Gly Leu Lys Lys Cys Phe His Glu Asn Ile Trp Leu Ser
    370                 375                 380

Ile Val Glu Val Ile Val Gly Ile Ser Leu Gln Val Leu Cys Ser Tyr
385                 390                 395                 400

Ile Thr Phe Pro Leu Tyr Ala Leu Val Thr Gln Met Gly Ser Asn Met
                405                 410                 415

Lys Lys Thr Ile Phe Glu Glu Gln Thr Met Lys Ala Leu Met Asn Trp
            420                 425                 430

Arg Lys Lys Ala Met Glu Lys Lys Lys Val Arg Asp Ala Asp Ala Phe
        435                 440                 445

Leu Ala Gln Met Ser Val Asp Phe Ala Thr Pro Ala Ser Ser Arg Ser
    450                 455                 460

Ala Ser Pro Val His Leu Leu Gln Val Thr Gly Arg Val Gly Arg Pro
465                 470                 475                 480
```

-continued

```
Pro Ser Pro Ile Thr Val Ala Ser Pro Pro Ala Pro Glu Glu Asp Met
                485                 490                 495

Tyr Pro Val Pro Ala Ala Ala Ala Ser Arg Gln Leu Leu Asp Asp Pro
            500                 505                 510

Pro Asp Arg Arg Trp Met Ala Ser Ser Ser Ala Asp Ile Ala Asp Ser
        515                 520                 525

Asp Phe Ser Phe Ser Ala Gln Arg
    530                 535


<210> SEQ ID NO 19
<211> LENGTH: 526
<212> TYPE: PRT
<213> ORGANISM: Arabidopsis thaliana

<400> SEQUENCE: 19

Met Gly His Gly Gly Glu Gly Met Ser Leu Glu Phe Thr Pro Thr Trp
  1               5                  10                  15

Val Val Ala Gly Val Cys Thr Val Ile Val Ala Ile Ser Leu Ala Val
             20                  25                  30

Glu Arg Leu Leu His Tyr Phe Gly Thr Val Leu Lys Lys Lys Lys Gln
         35                  40                  45

Lys Pro Leu Tyr Glu Ala Leu Gln Lys Val Lys Glu Glu Leu Met Leu
     50                  55                  60

Leu Gly Phe Ile Ser Leu Leu Leu Thr Val Phe Gln Gly Leu Ile Ser
 65                  70                  75                  80

Lys Phe Cys Val Lys Glu Asn Val Leu Met His Met Leu Pro Cys Ser
                 85                  90                  95

Leu Asp Ser Arg Arg Glu Ala Gly Ala Ser Glu His Lys Asn Val Thr
            100                 105                 110

Ala Lys Glu His Phe Gln Thr Phe Leu Pro Ile Val Gly Thr Thr Arg
        115                 120                 125

Arg Leu Leu Ala Glu His Ala Ala Val Gln Val Gly Tyr Cys Ser Glu
    130                 135                 140

Lys Gly Lys Val Pro Leu Leu Ser Leu Glu Ala Leu His His Leu His
145                 150                 155                 160

Ile Phe Ile Phe Val Leu Ala Ile Ser His Val Thr Phe Cys Val Leu
                165                 170                 175

Thr Val Ile Phe Gly Ser Thr Arg Ile His Gln Trp Lys Lys Trp Glu
            180                 185                 190

Asp Ser Ile Ala Asp Glu Lys Phe Asp Pro Glu Thr Ala Leu Arg Lys
        195                 200                 205

Arg Arg Val Thr His Val His Asn His Ala Phe Ile Lys Glu His Phe
    210                 215                 220

Leu Gly Ile Gly Lys Asp Ser Val Ile Leu Gly Trp Thr Gln Ser Phe
225                 230                 235                 240

Leu Lys Gln Phe Tyr Asp Ser Val Thr Lys Ser Asp Tyr Val Thr Leu
                245                 250                 255

Arg Leu Gly Phe Ile Met Thr His Cys Lys Gly Asn Pro Lys Leu Asn
            260                 265                 270

Phe His Lys Tyr Met Met Arg Ala Leu Glu Asp Asp Phe Lys Gln Val
        275                 280                 285

Val Gly Ile Ser Trp Tyr Leu Trp Ile Phe Val Val Ile Phe Leu Leu
    290                 295                 300

Leu Asn Val Asn Gly Trp His Thr Tyr Phe Trp Ile Ala Phe Ile Pro
```

-continued

```
305                 310                 315                 320

Phe Ala Leu Leu Leu Ala Val Gly Thr Lys Leu Glu His Val Ile Ala
                325                 330                 335

Gln Leu Ala His Glu Val Ala Glu Lys His Val Ala Ile Glu Gly Asp
            340                 345                 350

Leu Val Val Lys Pro Ser Asp Glu His Phe Trp Phe Ser Lys Pro Gln
        355                 360                 365

Ile Val Leu Tyr Leu Ile His Phe Ile Leu Phe Gln Asn Ala Phe Glu
    370                 375                 380

Ile Ala Phe Phe Phe Trp Ile Trp Val Thr Tyr Gly Phe Asp Ser Cys
385                 390                 395                 400

Ile Met Gly Gln Val Arg Tyr Ile Val Pro Arg Leu Val Ile Gly Val
                405                 410                 415

Phe Ile Gln Val Leu Cys Ser Tyr Ser Thr Leu Pro Leu Tyr Ala Ile
            420                 425                 430

Val Ser Gln Met Gly Ser Ser Phe Lys Lys Ala Ile Phe Glu Glu Asn
        435                 440                 445

Val Gln Val Gly Leu Val Gly Trp Ala Gln Lys Val Lys Gln Lys Arg
    450                 455                 460

Asp Leu Lys Ala Ala Ala Ser Asn Gly Asp Glu Gly Ser Ser Gln Ala
465                 470                 475                 480

Gly Pro Gly Pro Asp Ser Gly Ser Gly Ser Ala Pro Ala Ala Gly Pro
                485                 490                 495

Gly Ala Gly Phe Ala Gly Ile Gln Leu Ser Arg Val Thr Arg Asn Asn
            500                 505                 510

Ala Gly Asp Thr Asn Asn Glu Ile Thr Pro Asp His Asn Asn
        515                 520                 525
```

<210> SEQ ID NO 20
<211> LENGTH: 100
<212> TYPE: PRT
<213> ORGANISM: Hordeum vulgare

<400> SEQUENCE: 20

```
Lys Tyr Ile Lys Arg Ser Met Glu Asp Asp Phe Lys Val Val Val Gly
  1               5                  10                  15

Ile Ser Leu Pro Leu Trp Gly Val Ala Ile Leu Thr Leu Phe Leu Asp
             20                  25                  30

Ile Asn Gly Val Gly Thr Leu Ile Trp Ile Ser Phe Ile Pro Leu Val
         35                  40                  45

Ile Leu Leu Cys Val Gly Thr Lys Leu Glu Met Ile Ile Met Glu Met
     50                  55                  60

Ala Leu Glu Ile Gln Asp Arg Ala Ser Val Ile Lys Gly Ala Pro Val
 65                  70                  75                  80

Val Glu Pro Ser Asn Lys Phe Phe Trp Phe His Arg Pro Asp Trp Val
                 85                  90                  95

Leu Phe Phe Ile
            100
```

<210> SEQ ID NO 21
<211> LENGTH: 100
<212> TYPE: PRT
<213> ORGANISM: Arabidopsis thaliana
<220> FEATURE:
<221> NAME/KEY: SITE
<222> LOCATION: (23, 29, 48, 84, 85)
<223> OTHER INFORMATION: Xaa is any amino acid

<400> SEQUENCE: 21

```
Lys Tyr Met Met Arg Ala Leu Glu Asp Asp Phe Lys Gln Val Val Gly
  1               5                  10                  15

Ile Ser Trp Tyr Leu Trp Xaa Phe Val Val Ile Phe Xaa Leu Leu Asn
             20                  25                  30

Val Asn Gly Trp His Thr Tyr Phe Trp Ile Ala Phe Ile Pro Phe Xaa
         35                  40                  45

Leu Leu Leu Ala Val Gly Thr Lys Leu Glu His Val Ile Ala Gln Leu
     50                  55                  60

Ala His Glu Val Ala Glu Lys His Val Ala Ile Glu Gly Asp Leu Val
 65                  70                  75                  80

Val Lys Pro Xaa Xaa Glu His Phe Trp Phe Ser Lys Pro Gln Ile Val
                 85                  90                  95

Leu Tyr Leu Ile
            100
```

<210> SEQ ID NO 22
<211> LENGTH: 83
<212> TYPE: PRT
<213> ORGANISM: Hordeum vulgare

<400> SEQUENCE: 22

```
Lys Tyr Ile Lys Arg Ser Met Glu Asp Asp Phe Lys Val Val Val Gly
  1               5                  10                  15

Ile Ser Leu Pro Leu Trp Gly Val Ala Ile Leu Thr Leu Phe Leu Asp
             20                  25                  30

Ile Asn Gly Val Gly Thr Leu Ile Trp Ile Ser Phe Ile Pro Leu Val
         35                  40                  45

Ile Leu Leu Cys Val Gly Thr Lys Leu Glu Met Ile Ile Met Glu Met
     50                  55                  60

Ala Leu Glu Ile Gln Asp Arg Ala Ser Val Ile Lys Gly Ala Pro Val
 65                  70                  75                  80

Val Glu Pro
```

<210> SEQ ID NO 23
<211> LENGTH: 83
<212> TYPE: PRT
<213> ORGANISM: Arabidopsis thaliana
<220> FEATURE:
<221> NAME/KEY: SITE
<222> LOCATION: (23)
<223> OTHER INFORMATION: Xaa is any amino acid

<400> SEQUENCE: 23

```
Lys Tyr Met Met Arg Ala Leu Glu Asp Asp Phe Lys Gln Val Val Gly
  1               5                  10                  15

Ile Ser Trp Tyr Leu Trp Xaa Phe Val Val Ile Phe Leu Leu Leu Asn
             20                  25                  30

Val Asn Gly Trp His Thr Tyr Phe Trp Ile Ala Phe Ile Pro Phe Ala
         35                  40                  45

Leu Leu Leu Ala Val Gly Thr Lys Leu Glu His Val Ile Ala Gln Leu
     50                  55                  60

Ala His Glu Val Ala Glu Lys His Val Ala Ile Glu Gly Asp Leu Val
 65                  70                  75                  80

Val Lys Pro
```

-continued

<210> SEQ ID NO 24
<211> LENGTH: 32
<212> TYPE: PRT
<213> ORGANISM: Hordeum vulgare

<400> SEQUENCE: 24

Trp Ala Val Ala Val Val Phe Ala Ala Met Val Leu Val Ser Val Leu
1 5 10 15

Met Glu His Gly Leu His Lys Leu Gly His Trp Phe Gln His Arg His
20 25 30

<210> SEQ ID NO 25
<211> LENGTH: 32
<212> TYPE: PRT
<213> ORGANISM: Arabidopsis thaliana

<400> SEQUENCE: 25

Trp Ile Ala Phe Ile Pro Phe Ala Leu Leu Leu Ala Val Gly Thr Lys
1 5 10 15

Leu Glu His Val Ile Ala Gln Leu Ala His Glu Val Ala Glu Lys His
20 25 30

<210> SEQ ID NO 26
<211> LENGTH: 17
<212> TYPE: PRT
<213> ORGANISM: Hordeum vulgare

<400> SEQUENCE: 26

Glu Pro Ser Asn Lys Phe Phe Trp Phe His Arg Pro Asp Trp Val Leu
1 5 10 15

Phe

<210> SEQ ID NO 27
<211> LENGTH: 17
<212> TYPE: PRT
<213> ORGANISM: Arabidopsis thaliana
<220> FEATURE:
<221> NAME/KEY: SITE
<222> LOCATION: (14)
<223> OTHER INFORMATION: Xaa is any amino acid

<400> SEQUENCE: 27

Glu Thr Ser Asp Glu His Phe Trp Phe Ser Lys Pro Gln Xaa Val Leu
1 5 10 15

Tyr

<210> SEQ ID NO 28
<211> LENGTH: 96
<212> TYPE: PRT
<213> ORGANISM: Hordeum vulgare

<400> SEQUENCE: 28

Ser Lys Phe Asp Phe His Lys Tyr Ile Lys Arg Ser Met Glu Asp Asp
1 5 10 15

Phe Lys Val Val Val Gly Ile Ser Leu Pro Leu Trp Gly Val Ala Ile
20 25 30

Leu Thr Leu Phe Leu Asp Ile Asn Gly Val Gly Thr Leu Ile Trp Ile
35 40 45

Ser Phe Ile Pro Leu Val Ile Leu Leu Cys Val Gly Thr Lys Leu Glu
50 55 60

Met Ile Ile Met Glu Met Ala Leu Glu Ile Gln Asp Arg Ala Ser Val
65 70 75 80

-continued

```
Ile Lys Gly Ala Pro Val Val Glu Pro Ser Asn Lys Phe Phe Trp Phe
                 85                  90                  95


<210> SEQ ID NO 29
<211> LENGTH: 96
<212> TYPE: PRT
<213> ORGANISM: Arabidopsis thaliana
<220> FEATURE:
<221> NAME/KEY: SITE
<222> LOCATION: (93)
<223> OTHER INFORMATION: Xaa is any amino acid

<400> SEQUENCE: 29

Ser Arg Phe Asp Phe Arg Lys Tyr Ile Gln Arg Ser Leu Glu Lys Asp
  1               5                  10                  15

Phe Lys Thr Val Val Glu Ile Ser Pro Val Ile Trp Phe Val Ala Val
             20                  25                  30

Leu Phe Leu Leu Thr Asn Ser Tyr Gly Leu Arg Ser Tyr Leu Trp Leu
         35                  40                  45

Pro Phe Ile Pro Leu Val Val Ile Leu Ile Val Gly Thr Lys Leu Glu
     50                  55                  60

Val Ile Ile Thr Lys Leu Gly Leu Arg Ile Gln Glu Glu Gly Asp Val
 65                  70                  75                  80

Val Arg Gly Ala Pro Val Val Gln Pro Gly Asp Asp Xaa Phe Trp Phe
                 85                  90                  95


<210> SEQ ID NO 30
<211> LENGTH: 45
<212> TYPE: PRT
<213> ORGANISM: Hordeum vulgare

<400> SEQUENCE: 30

Ser Ser Thr Pro Gly Ile Arg Trp Val Val Ala Phe Phe Arg Gln Phe
  1               5                  10                  15

Phe Arg Ser Val Thr Lys Val Asp Tyr Leu Thr Leu Arg Ala Gly Phe
             20                  25                  30

Ile Asn Ala His Leu Ser Gln Asn Ser Lys Phe Asp Phe
         35                  40                  45


<210> SEQ ID NO 31
<211> LENGTH: 45
<212> TYPE: PRT
<213> ORGANISM: Arabidopsis thaliana
<220> FEATURE:
<221> NAME/KEY: SITE
<222> LOCATION: (29)
<223> OTHER INFORMATION: Xaa is any amino acid

<400> SEQUENCE: 31

Ser Lys Thr Arg Val Thr Leu Trp Ile Val Cys Phe Phe Arg Gln Phe
  1               5                  10                  15

Phe Gly Ser Val Thr Lys Val Asp Tyr Leu Ala Leu Xaa His Gly Phe
             20                  25                  30

Ile Met Ala His Phe Ala Pro Gly Asn Glu Ser Arg Phe
         35                  40                  45


<210> SEQ ID NO 32
<211> LENGTH: 86
<212> TYPE: PRT
<213> ORGANISM: Hordeum vulgare

<400> SEQUENCE: 32
```

-continued

```
Ser Ser Thr Pro Gly Ile Arg Trp Val Val Ala Phe Phe Arg Gln Phe
  1               5                  10                  15

Phe Arg Ser Val Thr Lys Val Asp Tyr Leu Thr Leu Arg Ala Gly Phe
             20                  25                  30

Ile Asn Ala His Leu Ser Gln Asn Ser Lys Phe Asp Phe His Lys Tyr
         35                  40                  45

Ile Lys Arg Ser Met Glu Asp Asp Phe Lys Val Val Val Gly Ile Ser
     50                  55                  60

Leu Pro Leu Trp Gly Val Ala Ile Leu Thr Leu Phe Leu Asp Ile Asn
 65                  70                  75                  80

Gly Val Gly Thr Leu Ile
                 85


<210> SEQ ID NO 33
<211> LENGTH: 85
<212> TYPE: PRT
<213> ORGANISM: Arabidopsis thaliana
<220> FEATURE:
<221> NAME/KEY: SITE
<222> LOCATION: (6, 33, 51, 64, 79)
<223> OTHER INFORMATION: Xaa is any amino acid

<400> SEQUENCE: 33

Thr Thr Thr Pro Phe Xaa Phe Asn Val Gly Cys Phe Phe Arg Gln Phe
  1               5                  10                  15

Phe Val Ser Val Glu Arg Thr Asp Tyr Leu Thr Leu Arg His Gly Phe
             20                  25                  30

Xaa Ser Ala His Leu Ala Pro Gly Arg Lys Phe Asn Phe Gln Arg Tyr
         35                  40                  45

Ile Lys Xaa Ser Leu Glu Asp Asp Phe Lys Leu Val Val Gly Ile Xaa
     50                  55                  60

Pro Val Leu Trp Ala Ser Phe Val Ile Phe Leu Ala Val Gln Xaa Trp
 65                  70                  75                  80

Leu Gly Thr Ile Val
                 85


<210> SEQ ID NO 34
<211> LENGTH: 57
<212> TYPE: PRT
<213> ORGANISM: Hordeum vulgare

<400> SEQUENCE: 34

Met Arg Thr Trp Lys Lys Trp Glu Thr Glu Thr Thr Ser Leu Glu Tyr
  1               5                  10                  15

Gln Phe Ala Asn Asp Pro Ala Arg Phe Arg Phe Thr His Gln Thr Ser
             20                  25                  30

Phe Val Lys Arg His Leu Gly Leu Ser Ser Thr Pro Gly Ile Arg Trp
         35                  40                  45

Val Val Ala Phe Phe Arg Gln Phe Phe
     50                  55


<210> SEQ ID NO 35
<211> LENGTH: 57
<212> TYPE: PRT
<213> ORGANISM: Arabidopsis thaliana
<220> FEATURE:
<221> NAME/KEY: SITE
<222> LOCATION: (10, 17, 19, 47)
<223> OTHER INFORMATION: Xaa is any amino acid
```

-continued

<400> SEQUENCE: 35

```
Ile Arg Gly Trp Lys Lys Trp Glu Gln Xaa Thr Leu Ser Asn Asp Tyr
  1               5                  10                  15

Xaa Phe Xaa Ile Asp His Ser Arg Leu Arg Leu Thr His Glu Thr Ser
             20                  25                  30

Phe Val Arg Glu His Thr Ser Phe Trp Thr Thr Thr Pro Phe Xaa Phe
         35                  40                  45

Asn Val Gly Cys Phe Phe Arg Gln Phe
     50                  55
```

<210> SEQ ID NO 36
<211> LENGTH: 19
<212> TYPE: PRT
<213> ORGANISM: Hordeum vulgare

<400> SEQUENCE: 36

```
Thr Leu Phe Leu Asp Ile Asn Gly Val Gly Thr Leu Ile Trp Ile Ser
  1               5                  10                  15

Phe Ile Pro
```

<210> SEQ ID NO 37
<211> LENGTH: 19
<212> TYPE: PRT
<213> ORGANISM: Arabidopsis thaliana
<220> FEATURE:
<221> NAME/KEY: SITE
<222> LOCATION: (6)
<223> OTHER INFORMATION: Xaa is any amino acid

<400> SEQUENCE: 37

```
Ser Leu Leu Phe Asn Xaa Asn Gly Trp Gly Pro Leu Phe Trp Ala Ser
  1               5                  10                  15

Val Pro Pro
```

<210> SEQ ID NO 38
<211> LENGTH: 60
<212> TYPE: PRT
<213> ORGANISM: Hordeum vulgare

<400> SEQUENCE: 38

```
Val Ile Thr Ile Ala Leu Ser Arg Leu Lys Met Arg Thr Trp Lys Lys
  1               5                  10                  15

Trp Glu Thr Glu Thr Thr Ser Leu Glu Tyr Gln Phe Ala Asn Asp Pro
             20                  25                  30

Ala Arg Phe Arg Phe Thr His Gln Thr Ser Phe Val Lys Arg His Leu
         35                  40                  45

Gly Leu Ser Ser Thr Pro Gly Ile Arg Trp Val Val
     50                  55                  60
```

<210> SEQ ID NO 39
<211> LENGTH: 60
<212> TYPE: PRT
<213> ORGANISM: Arabidopsis thaliana

<400> SEQUENCE: 39

```
Ile Val Thr Tyr Ala Phe Gly Lys Ile Lys Met Arg Thr Trp Lys Ser
  1               5                  10                  15

Trp Glu Glu Glu Thr Lys Thr Ile Glu Tyr Gln Tyr Ser Asn Asp Pro
             20                  25                  30

Glu Arg Phe Arg Phe Ala Arg Asp Thr Ser Phe Gly Arg Arg His Leu
```

-continued

```
        35                  40                  45

Asn Phe Trp Ser Lys Thr Arg Val Thr Leu Trp Ile
     50                  55                  60


<210> SEQ ID NO 40
<211> LENGTH: 45
<212> TYPE: PRT
<213> ORGANISM: Hordeum vulgare

<400> SEQUENCE: 40

Ser Ser Thr Pro Gly Ile Arg Trp Val Val Ala Phe Phe Arg Gln Phe
  1               5                  10                  15

Phe Arg Ser Val Thr Lys Val Asp Tyr Leu Thr Leu Arg Ala Gly Phe
             20                  25                  30

Ile Asn Ala His Leu Ser Gln Asn Ser Lys Phe Asp Phe
        35                  40                  45


<210> SEQ ID NO 41
<211> LENGTH: 45
<212> TYPE: PRT
<213> ORGANISM: Arabidopsis thaliana
<220> FEATURE:
<221> NAME/KEY: SITE
<222> LOCATION: (29)
<223> OTHER INFORMATION: Xaa is any amino acid

<400> SEQUENCE: 41

Ser Lys Thr Arg Val Thr Leu Trp Ile Val Cys Phe Phe Arg Gln Phe
  1               5                  10                  15

Phe Gly Ser Val Thr Lys Val Asp Tyr Leu Ala Leu Xaa His Gly Phe
             20                  25                  30

Ile Met Ala His Phe Ala Pro Gly Asn Glu Ser Arg Phe
        35                  40                  45


<210> SEQ ID NO 42
<211> LENGTH: 21
<212> TYPE: PRT
<213> ORGANISM: Hordeum vulgare

<400> SEQUENCE: 42

Ser Lys Phe Asp Phe His Lys Tyr Ile Lys Arg Ser Met Glu Asp Asp
  1               5                  10                  15

Phe Lys Val Val Val
             20


<210> SEQ ID NO 43
<211> LENGTH: 21
<212> TYPE: PRT
<213> ORGANISM: Arabidopsis thaliana
<220> FEATURE:
<221> NAME/KEY: SITE
<222> LOCATION: (14, 15)
<223> OTHER INFORMATION: Xaa is any amino acid

<400> SEQUENCE: 43

Ser Arg Phe Asp Phe Arg Lys Tyr Ile Gln Arg Ser Leu Xaa Xaa Asp
  1               5                  10                  15

Phe Lys Thr Val Val
             20


<210> SEQ ID NO 44
<211> LENGTH: 53
<212> TYPE: PRT
```

-continued

<213> ORGANISM: Hordeum vulgare

<400> SEQUENCE: 44

```
Ser Lys Phe Asp Phe His Lys Tyr Ile Lys Arg Ser Met Glu Asp Asp
  1               5                  10                  15

Phe Lys Val Val Val Gly Ile Ser Leu Pro Leu Trp Gly Val Ala Ile
             20                  25                  30

Leu Thr Leu Phe Leu Asp Ile Asn Gly Val Gly Thr Leu Ile Trp Ile
         35                  40                  45

Ser Phe Ile Pro Leu
     50
```

<210> SEQ ID NO 45
<211> LENGTH: 53
<212> TYPE: PRT
<213> ORGANISM: Oryza sativa
<220> FEATURE:
<221> NAME/KEY: SITE
<222> LOCATION: (12, 27, 51)
<223> OTHER INFORMATION: Xaa is any amino acid

<400> SEQUENCE: 45

```
Thr Arg Phe Asn Phe Arg Lys Tyr Ile Lys Arg Xaa Leu Glu Asp Asp
  1               5                  10                  15

Phe Lys Thr Val Val Gly Ile Ser Ala Pro Xaa Trp Ala Ser Ala Leu
             20                  25                  30

Ala Ile Met Leu Phe Asn Val His Gly Trp His Asn Leu Phe Trp Phe
         35                  40                  45

Ser Thr Xaa Pro Leu
     50
```

<210> SEQ ID NO 46
<211> LENGTH: 15
<212> TYPE: PRT
<213> ORGANISM: Hordeum vulgare

<400> SEQUENCE: 46

```
Pro Leu Val Ile Leu Leu Cys Val Gly Thr Lys Leu Glu Met Ile
  1               5                  10                  15
```

<210> SEQ ID NO 47
<211> LENGTH: 15
<212> TYPE: PRT
<213> ORGANISM: Oryza sativa
<220> FEATURE:
<221> NAME/KEY: SITE
<222> LOCATION: (3)
<223> OTHER INFORMATION: Xaa is any amino acid

<400> SEQUENCE: 47

```
Pro Leu Xaa Val Thr Leu Ala Val Gly Thr Lys Leu Gln Ala Ile
  1               5                  10                  15
```

<210> SEQ ID NO 48
<211> LENGTH: 58
<212> TYPE: PRT
<213> ORGANISM: Hordeum vulgare

<400> SEQUENCE: 48

```
His Trp Phe Gln His Arg His Lys Lys Ala Leu Trp Glu Ala Leu Glu
  1               5                  10                  15

Lys Met Lys Ala Glu Leu Met Leu Val Gly Phe Ile Ser Leu Leu Leu
             20                  25                  30
```

-continued

```
Ile Val Thr Gln Asp Pro Ile Ile Ala Lys Ile Cys Ile Ser Glu Asp
        35                  40                  45

Ala Ala Asp Val Met Trp Pro Cys Lys Arg
    50                  55
```

<210> SEQ ID NO 49
<211> LENGTH: 58
<212> TYPE: PRT
<213> ORGANISM: Oryza sativa
<220> FEATURE:
<221> NAME/KEY: SITE
<222> LOCATION: (2)
<223> OTHER INFORMATION: Xaa is any amino acid

<400> SEQUENCE: 49

```
His Xaa Ser Glu Lys Thr His Arg Asn Pro Leu His Lys Ala Met Glu
  1               5                  10                  15

Lys Met Lys Glu Glu Met Met Leu Leu Gly Phe Ile Ser Leu Leu Leu
            20                  25                  30

Ala Ala Thr Ser Arg Ile Ile Ser Gly Ile Cys Ile Asp Ser Lys Tyr
        35                  40                  45

Tyr Asn Ser Asn Phe Ser Pro Cys Thr Arg
    50                  55
```

<210> SEQ ID NO 50
<211> LENGTH: 382
<212> TYPE: DNA
<213> ORGANISM: Arabidopsis thaliana
<220> FEATURE:
<221> NAME/KEY: misc_feature
<222> LOCATION: (68, 88, 143, 181, 251, 254, 328, 333, 337, 341)
<223> OTHER INFORMATION: n is a or g or c or t
<220> FEATURE:
<221> NAME/KEY: misc_feature
<222> LOCATION: (348, 349, 356, 357, 368, 370, 372, 373, 381)
<223> OTHER INFORMATION: n is a or g or c or t

<400> SEQUENCE: 50

```
caagtatatg atgcgcgctc tagaggatga tttcaaacaa gttgttggta ttagttggta     60

tctttggntc tttgtcgtca tctttttnct gctaaatgtt aacggatggc acacatattt    120

ctggatagca tttattccct ttnctttgct tcttgctgtg ggaacaaagt tggagcatgt    180

nattgcacag ttagctcatg aagttgcaga gaaacatgta gccattgaag gagacttagt    240

ggtgaaaccc ncanatgagc atttctggtt cagcaaacct caaattgttc tctacttgat    300

cccattttat cctctttccc agaatgcntt ttnagantgc nttttttnnt tttggnnttt    360

ggggtaanan annggtttcg nc                                              382
```

<210> SEQ ID NO 51
<211> LENGTH: 390
<212> TYPE: DNA
<213> ORGANISM: Arabidopsis thaliana
<220> FEATURE:
<221> NAME/KEY: misc_feature
<222> LOCATION: (68, 181, 284, 296, 302, 331, 333, 339..341, 351, 357)
<223> OTHER INFORMATION: n is a or g or c or t
<220> FEATURE:
<221> NAME/KEY: misc_feature
<222> LOCATION: (358, 366..369, 378, 380)
<223> OTHER INFORMATION: n is a or g or c or t

<400> SEQUENCE: 51

```
caagtatatg atgcgcgctc tagaggatga tttcaaacaa gttgttggta ttagttggta     60
```

-continued

```
tctttggntc tttgtcgtca tctttttgct gctaaatgtt aacggatggc acacatattt    120

ctggatagca tttattccct ttgctttgct tcttgctgtg ggaacaaagt tggagcatgt    180

nattgcacag ttagctcatg aagttgcaga gaaacatgta gccattgaag gagacttagt    240

ggtgaaacct cagatgagca tttctggttc agcaaacctc aaantgttct ctactngatc    300

cnctttatcc cccttccaga atgccttttt nangattcnn ntttttcctt nttggannttt   360

ttgggnnnnc aaacgggntt nggacctccg                                     390
```

<210> SEQ ID NO 52
<211> LENGTH: 585
<212> TYPE: DNA
<213> ORGANISM: Arabidopsis thaliana
<220> FEATURE:
<221> NAME/KEY: misc_feature
<222> LOCATION: (87, 404, 415, 417, 420, 425, 432, 439, 442)
<223> OTHER INFORMATION: n is a or g or c or t
<220> FEATURE:
<221> NAME/KEY: misc_feature
<222> LOCATION: (449, 460, 480, 485, 493, 511, 515, 527, 530, 551)
<223> OTHER INFORMATION: n is a or g or c or t
<220> FEATURE:
<221> NAME/KEY: misc_feature
<222> LOCATION: (558, 567, 571, 582)
<223> OTHER INFORMATION: n is a or g or c or t

<400> SEQUENCE: 52

```
agcaagacga gagtcacact atggattgtt tgttttttta gacagttctt tggatctgtc     60

accaaagttg attacttagc actaagncat ggtttcatca tggcgcattt tgctcccggt    120

aacgaatcaa gattcgattt ccgcaagtat attcagagat cattagagaa agacttcaaa    180

accgttgttg aaatcagtcc ggttatctgg tttgtcgctg tgctattcct cttgaccaat    240

tcatatggat tacgttctta cctctggtta ccattcattc cactagtcgt aattctaata    300

gttggaacaa agcttgaagt cataataaca aaattgggtc taaggatcca agaggaaggt    360

gatgtggtga gaggcgcccc agtggttcag cctggtgatg accncttctg gtttngnaan    420

cacgnttcaa tnttttccnt antcacttng gcctttttan gggtgaattt caacttcatn    480

ctttncctgg ggncggatga ttcaatccaa naatnttccc ctgaagnctn caagtttggg    540

cataggcttt nggtgggntt ttcaganttt nagtttggct tnccc                    585
```

<210> SEQ ID NO 53
<211> LENGTH: 460
<212> TYPE: DNA
<213> ORGANISM: Arabidopsis thaliana
<220> FEATURE:
<221> NAME/KEY: misc_feature
<222> LOCATION: (117, 243, 323, 325, 388, 407, 409, 414, 417, 419)
<223> OTHER INFORMATION: n is a or g or c or t
<220> FEATURE:
<221> NAME/KEY: misc_feature
<222> LOCATION: (435, 446, 458)
<223> OTHER INFORMATION: n is a or g or c or t

<400> SEQUENCE: 53

```
tgcattgtta cttatgcttt cggaaagatc aagatgagga cgtggaagtc gtgggaggaa     60

gagacaaaga caatagagta tcagtattcc aacgatcctg agaggttcag gtttgcnagg    120

gacacatctt ttgggagaag acatctcaat ttctggagca agacgagagt cacactatgg    180

attgtttgtt tttttagaca gttctttgga tctgtcacca aagttgatta cttagcacta    240

agncatggtt tcatcatggc gcattttgct cccggtaacg aatcaagatt cgatttccgc    300

aagtatattc agagatcatt agngnaagac ttcaaaaccg ttgtttgaaa tcagtccggt    360
```

-continued

```
tatctggttt gtcggctgtg ctattccnct tgaccaattc atatggntnc ggtnttncnc    420

tggtaccatt attcnctagc ggaatntaaa agttggcnga                          460


<210> SEQ ID NO 54
<211> LENGTH: 476
<212> TYPE: DNA
<213> ORGANISM: Arabidopsis thaliana
<220> FEATURE:
<221> NAME/KEY: misc_feature
<222> LOCATION: (30, 49, 55, 102, 132, 140, 183, 221, 274, 315)
<223> OTHER INFORMATION: n is a or g or c or t
<220> FEATURE:
<221> NAME/KEY: misc_feature
<222> LOCATION: (360, 388, 401, 408, 411, 443, 469, 473, 474)
<223> OTHER INFORMATION: n is a or g or c or t

<400> SEQUENCE: 54

attcgtggat ggaaaaagtg ggagcaagan acattatcta atgactatna gtttnctatt     60

gatcattcaa gacttaggct cactcatgag acttcttttg tnagagaaca tacaagtttc    120

tggacaacaa cncctttctn ctttaacgtc ggatgcttct ttaggcagtt ctttgtatct    180

gtngaaagaa ccgactactt gactctgcgc catggattca nctctgccca tttagctcca    240

ggaagaaagt tcaacttcca gagatatatc aaangatctc tcgaggatga tttcaagttg    300

gtagttggaa taagnccagt tctttgggca tcatttgtaa tcttccttgc tgttcaatgn    360

taatggctgg ggaccattgt tttgggcntc ggtaccgcct ntactcanaa ncccaggctt    420

ttggccaagg ttcaaggaat ttngggacaa tggggtagaa tcgtgggcnc atnngg        476


<210> SEQ ID NO 55
<211> LENGTH: 400
<212> TYPE: DNA
<213> ORGANISM: Oryza sativa
<220> FEATURE:
<221> NAME/KEY: misc_feature
<222> LOCATION: (3, 5, 9, 10, 17, 18, 20, 22, 32..35, 37, 41)
<223> OTHER INFORMATION: n is a or g or c or t
<220> FEATURE:
<221> NAME/KEY: misc_feature
<222> LOCATION: (43, 45, 47, 50..53, 62, 65, 68, 71, 73, 75, 80, 81)
<223> OTHER INFORMATION: n is a or g or c or t
<220> FEATURE:
<221> NAME/KEY: misc_feature
<222> LOCATION: (89..91, 100, 107, 108, 113..115, 134, 153, 167, 176)
<223> OTHER INFORMATION: n is a or g or c or t
<220> FEATURE:
<221> NAME/KEY: misc_feature
<222> LOCATION: (235, 280, 354, 362)
<223> OTHER INFORMATION: n is a or g or c or t

<400> SEQUENCE: 55

tcntntttnn ttttcgnntn cntccacccc tnnnntnctc nancncnttn nnnttatctc     60

tnttnttntc ncntntcccn ncaccaccnn ncgacgggcn tggactnngc ccnnngttcg    120

aggctgccca ctgncgtctg agacctacct tgncatttga cggcacngga cttcanttgc    180

tgctcacttt atctctacgg gactaggttc aattttcgga aatacatcaa aaggncactg    240

gaggacgatt ttaagacagt tgttggcatt agtgcacccn tatgggcttc tgcgttggcc    300

attatgctct tcaatgttca tggatggcat aacttgttct ggttctctac aatnccccttt    360

gntagtaact ttagcagttg gaacaaagct gcaggctata                          400


<210> SEQ ID NO 56
<211> LENGTH: 325
<212> TYPE: DNA
```

-continued

<213> ORGANISM: Oryza sativa
<220> FEATURE:
<221> NAME/KEY: misc_feature
<222> LOCATION: (164)
<223> OTHER INFORMATION: n is a or g or c or t

<400> SEQUENCE: 56
cagactacct gactttgagg cacggattca ttgctgctca tttatctcta gggactaggt 60
tcaattttcg gaaatacatc aaaaggtcac tggaggacga ttttaagaca gttgttggca 120
ttagtgcacc cttatgggct tctgcgttgg ccattatgct cttnaatgtt catggatggc 180
ataacttgtt ctggttctct acaatccccc ttgtagtaac tttagcagtt ggaacaaagc 240
tgcaggctat aattgcaatg atggctgttg aaattaaaga gaggcataca gtaattcaag 300
gaatgccggt ggtgaactca gtgat 325

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 57
gtgcatctgc gtgtgcgta 19

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 58
gtgtgcgtac ctggtagag 19

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 59
aacgacgtct ggtgcgtg 18

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 60
tgcagctata tgaccttccc cctc 24

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 61
ggacatgctg atggctcaga 20

-continued

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 62
cagaacttgt ctcatccctg 20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 63
ggctatacat tgggactaac a 21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 64
cgaatcatca catcctatgt t 21

<210> SEQ ID NO 65
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 65
gcaagttcga cttccac 17

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 66
tcgacttcca caagtacatc a 21

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 67
agcgtacctg cgtacgtag 19

<210> SEQ ID NO 68
<211> LENGTH: 19
<212> TYPE: DNA
<213> ORGANISM: Artificial Sequence
<220> FEATURE:

-continued

<223> OTHER INFORMATION: Description of Artificial Sequence: Primer

<400> SEQUENCE: 68
gttgccacac tttgccacg 19

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 69
aagccaagac gacaatcaga 20

<210> SEQ ID NO 70
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 70
grrgccacac tttgccacg 19

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
aagccaagac gacaatcaga 20

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 72
gtgcatctgc gtgtgcgta 19

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 73
cagaaacttg tctcatccct g 21

<210> SEQ ID NO 74
<211> LENGTH: 17
<212> TYPE: DNA
<213> ORGANISM: Artificial Sequence
<220> FEATURE:
<223> OTHER INFORMATION: Description of Artificial Sequence: Primer

<400> SEQUENCE: 74
agggtcagga tcgccac 17

-continued

```
<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 75

ttgtggaggc cgtgttcc                                                18


<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 76

tgcagctata tgaccttccc cctc                                         24


<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 77

ggacatgctg atggctcaga                                              20


<210> SEQ ID NO 78
<211> LENGTH: 5
<212> TYPE: PRT
<213> ORGANISM: Hordeum vulgare

<400> SEQUENCE: 78

Lys Lys Lys Val Arg
  1               5


<210> SEQ ID NO 79
<211> LENGTH: 4
<212> TYPE: PRT
<213> ORGANISM: Hordeum vulgare

<400> SEQUENCE: 79

Ser Ile Phe Asp
  1
```